United States Patent
Dellacasagrande

(10) Patent No.: US 8,734,794 B2
(45) Date of Patent: May 27, 2014

(54) HUMANISED ANTIBODIES TO TOLL-LIKE RECEPTOR 2 AND USES THEREOF

(75) Inventor: Jerome Dellacasagrande, Toulouse (FR)

(73) Assignee: Opsona Therapeutics Limited, Dublin (IE)

( * ) Notice: Subject to any disclaimer, the term of this patent is extended or adjusted under 35 U.S.C. 154(b) by 83 days.

(21) Appl. No.: 13/382,044

(22) PCT Filed: Jul. 6, 2010

(86) PCT No.: PCT/EP2010/059677
§ 371 (c)(1),
(2), (4) Date: Mar. 15, 2012

(87) PCT Pub. No.: WO2011/003925
PCT Pub. Date: Jan. 13, 2011

(65) Prior Publication Data
US 2012/0164159 A1    Jun. 28, 2012

Related U.S. Application Data

(60) Provisional application No. 61/270,239, filed on Jul. 6, 2009.

(30) Foreign Application Priority Data

Jul. 6, 2009 (IE) .................................. 2009/0514

(51) Int. Cl.
| | |
|---|---|
| A61K 39/395 | (2006.01) |
| C07K 16/28 | (2006.01) |
| C12P 21/00 | (2006.01) |
| C12N 15/09 | (2006.01) |
| C12N 15/13 | (2006.01) |
| C12N 15/63 | (2006.01) |
| C12N 5/10 | (2006.01) |
| C12N 5/12 | (2006.01) |

(52) U.S. Cl.
USPC .................. 424/133.1; 424/143.1; 435/69.1; 435/70.1; 435/70.2; 435/235.1; 435/320.1; 435/326; 435/334; 530/387.1; 530/388.22

(58) Field of Classification Search
CPC .... C07K 16/00; C07K 16/28; C07K 16/2863; C07K 16/2896; C12P 21/005; C12N 5/12; C12N 15/02; C12N 15/09; C12N 15/63; C12N 15/86; A61K 39/39533
See application file for complete search history.

(56) References Cited

U.S. PATENT DOCUMENTS

| | | | |
|---|---|---|---|
| 4,376,110 | A | 3/1983 | David et al. |
| 5,831,012 | A | 11/1998 | Nilsson et al. |
| 6,291,158 | B1 | 9/2001 | Winter et al. |
| 6,582,915 | B1 | 6/2003 | Griffiths et al. |
| 6,593,081 | B1 | 7/2003 | Griffiths et al. |
| 7,071,310 | B1 * | 7/2006 | Espevik et al. ............ 530/388.1 |
| 7,250,297 | B1 | 7/2007 | Beste et al. |
| 2005/0053973 | A1 | 3/2005 | Kolkman et al. |
| 2005/0089932 | A1 | 4/2005 | Kolkman et al. |
| 2005/0164301 | A1 | 7/2005 | Kolkman et al. |
| 2007/0191272 | A1 | 8/2007 | Stemmer et al. |

FOREIGN PATENT DOCUMENTS

| | | |
|---|---|---|
| EP | 0368684 A1 | 5/1990 |
| WO | WO-92/22324 A1 | 12/1992 |
| WO | WO-99/16873 A1 | 4/1999 |
| WO | WO-01/36488 A1 | 5/2001 |
| WO | WO-02/20565 A2 | 3/2002 |
| WO | WO-2004/044011 A2 | 5/2004 |
| WO | WO-2005/019431 A2 | 3/2005 |
| WO | WO-2005/028509 A1 | 3/2005 |
| WO | WO-2006/082406 | 8/2006 |
| WO | WO-2007/099341 A1 | 9/2007 |

OTHER PUBLICATIONS

Arslan et al. Circulation 121: 80-90, 2010.*
Arslan et al. Treatment with OPN-305, a humanized anti-toll-like receptor 2 antibody, reduces myocardial ischemia/reperfusion injury in pigs. Circ Cardiovascul Interv 5: 279-287, 2012.*
Begon et al. Expression, subcellular localization and cytokinic modulation of toll-like receptors (TLRS) in normal human keratinocytes: TLR2 upregulation in psoriatic skin. Eur J Dermatol 17(6): 497-506, 2007.*
Brorson et al. Mutational analysis of avidity and fine specificity of anti-levan antibodies. J Immunol 163: 6694-6701, 1999.*
Brummell et al. Biochemistry 32(4): 1180-1187, 1993 (abstract only).*
Burks et al. In vitro scanning saturation mutagenesis of an antibody binding pocket. Proc Natl Acad Sci USA 94: 412-417, 1997.*
Casset et al (2003. Biochemical and Biophysical Research Communications. 307: 198-205).*
Chen et al (1999. J Mol Biol. 293: 865-881).*
Colman (Research in Immunol. 145:33-36 (1994)).*
Curtiss et al. Emerging role of Toll-like receptors in atherosclerosis. J Lipid Res 50: S340-S345, 2009.*
De Pascalis et al (2002. The Journal of Immunology. 169: 3076-3084).*
Farrar et al. Inhibition of TLR2 promotes graft function in a murine model of renal transplant ischemia-reperfusion injury. FASEB J 26: 799-807, 2012.*

(Continued)

Primary Examiner — Bridget E Bunner
(74) Attorney, Agent, or Firm — Marshall, Gerstein & Borun LLP

(57) ABSTRACT

A fully humanized antibody having binding specificity to Toll-like Receptor 2 comprises a light chain and a heavy chain entirely comprised of amino acid sequence of human origin. The variable region of the light chain comprises an amino acid sequence which is substantially homologous with the sequence of SEQ ID NO:1, while the variable region of the heavy domain comprises an amino acid sequence which is substantially homologous with the sequence of SEQ ID NO:4. Also provided are nucleic acids encoding such antibodies, as well as the use of the antibodies in medicine, in particular for the treatment of inflammatory and autoimmune diseases which are mediated by Toll-like Receptor 2 activation and signalling.

24 Claims, 37 Drawing Sheets
(6 of 37 Drawing Sheet(s) Filed in Color)

(56) References Cited

OTHER PUBLICATIONS

Holm et al (2007. Mol Immunology. 44: 1075-1084).*
Jang et al. Molecular Immunol 35: 1207-1217, 1998.*
Kobayashi et al. Protein Engineer 12(10): 879-884, 1999.*
MacCaallum et al. J Mol Biol 262: 732-745, 1996.*
Meng et al. Antagonistic antibody prevents toll-like receptor 2-drived lethal shock-like syndromes. J Clin Invest 113(10): 1473-1481, 2004.*
O'Neill et al. Therapeutic targeting of toll-like receptors for infectious and inflammatory diseases and cancer. Pharmacol Rev 61: 177-197, 2009.*
Paul, William E., Fundamental Immunology, 3rd Edition, Raven Press, New York, Chapt. 8, pp. 242, 292-295 (1993).*
Rudikoff et al, 1982 (Proc Natl Acad Sci USA. vol. 79: 1979-1983).*
Senn et al. Toll-like receptor 2 is essential for the development of palmitate-induced insulin resistance in myotubes. J Biol Chem 281: 26865-26875, 2006.*
Nic An Ultaigh et al. Blockade of toll-like receptor 2 prevents spontaneous cytokine release from rheumatoid arthritis ex vivo synovial explant cultures. Arthritis Res & Therapy 13: R33, 2011 (9 pages).*
Vajdos et al (2002. J Mol Biol. 320: 415-428).*
Wu et al (1999. J Mol Biol. 294: 151-162).*
Angal et al., A single amino acid substitution abolishes the heterogeneity of chimeric mouse/human (IgG4) antibody, Mol. Immunol., 30(1):105-8 (1993).
Better et al., *Escherichia coli* secretion of an active chimeric antibody fragment, Science, 240(4855):1041-3 (1988).
Carter et al., High level *Escherichia coli* expression and production of a bivalent humanized antibody fragment, Biotechnology (NY), 10(2):163-7 (1992).
Clackson et al., Making antibody fragments using phage display libraries, Nature, 352(6336):624-8 (1991).
Damewood, Peptide mimetic design with the aid of computational chemistry, Rev. Computational Biol., 9:1-80 (2007).
Dougall et al., Antibody-structure-based design of pharmacological agents, Trends Biotechnol., 12(9):372-9 (1994).
Huston et al., Protein engineering of single-chain Fv analogs and fusion proteins, Methods Enzymol., 203:46-88 (1991).
International Preliminary Report on Patentability for corresponding International application No. PCT/EP2010/059677, dated Jan. 10, 2012.
International Search Report and Written Opinion from corresponding International application No. PCT/EP2010/059677, mailing date Sep. 7, 2010.
Morimoto et al., Single-step purification of F(ab')2 fragments of mouse monoclonal antibodies (immunoglobulins G1) by hydrophobic interaction high performance liquid chromatography using TSKgel Phenyl-5PW, J. Biochem. Biophys. Methods, 24(1-2):107-17 (1992).
Portolano et al., Lack of promiscuity in autoantigen-specific H and L chain combinations as revealed by human H and L chain "roulette", J. Immunol., 150(3):880-7 (1993).
Saragovi et al., Design and synthesis of a mimetic from an antibody complementarity-determining region, Science, 253(5021):792-5 (1991).
Saragovi et al., Loops and secondary structure mimetics: development and applications in basic science and rational drug design, Biotechnology (NY), 10(7): 773-8 (1992).
Sawai et al., Direct production of the Fab fragment derived from the sperm immobilizing antibody using polymerase chain reaction and cDNA expression vectors, Am. J. Reprod. Immunol., 34(1):26-34 (1995).
Williams et al., Design of bioactive peptides based on antibody hypervariable region structures. Development of conformationally constrained and dimeric peptides with enhanced affinity, J. Biol. Chem., 266(8):5182-90 (1991).

* cited by examiner

DIVLTQSPATLSLSPGERATLSC<u>RASESVEYYGTSLMQ</u>WYQ
QKPGQPPKLLIF<u>GASNVES</u>GVPDRFSGSGSGTDFTLKISRVE
AEDVGMYFC<u>QQSRKLPWT</u>FGGGTKVEIK

Figure 1A - SEQ ID NO:1

GACATTGTGCTCACCCAATCTCCAGCTACTTTGTCTCTGTCTCCAGGGGAGAGAGCCACCCTCTCCTGCAGAGCCAGTGAAAGTGTTGAATACTATGGCA
 D  I  V  L  T  Q  S  P  A  T  L  S  L  S  P  G  E  R  A  T  L  S  C  R  A  S  E  S  V  E  Y  Y  G
                                                                              27 a  b  c  d

CAAGTTTAATGCAGTGGTACCAACAGAAACCAGGACAGGCCACCTAAACTCCTCATCTTTGGTGCATCCAACGTAGAATCTGGGGTCCCTGACAGGTTCAG
 S  L  M  Q  W  Y  Q  Q  K  P  G  Q  P  P  K  L  L  I  F  G  A  S  N  V  E  S  G  V  P  D  R  F  S

TGGCAGTGGGTCTGGGACAGACTTCACCCTCAAGATCAGCCGGGTGGAGGCCGAGGATGTTGGAATGTATTTCTGTCAGCAAAGTAGGAAACTTCCGTGG
 G  S  G  S  G  T  D  F  T  L  K  I  S  R  V  E  A  E  D  V  G  M  Y  F  C  Q  Q  S  R  K  L  P  W

ACGTTCGGTGGAGGCACCAAGGTGGAAATCAAA
 T  F  G  G  G  T  K  V  E  I  K

Figure 1B

QVQLVQSGSELKKPGASVKLSCKASGFTFT<u>TYGIN</u>WVRQAP
GQGLEWIG<u>WIYPRDGSTNFNENFKD</u>RATITVDTSASTAYMEL
SSLRSEDTAVYFCAR<u>LTGGTFLDY</u>WGQGTTVTVSS

Figure 2A – SEQ ID NO:4

```
        10                  20                  30                  40                  50                  60                  70                  80                  90                 100
CAGGTTCAGCTGGTGCAGTCTGGAGATCTGAGCTGAAGAAGCCTGGGGCGTCAGTGAAGGTTGTCCTGCAAGGCTTCTGGCTTCACCAACCTACGGTA
 Q  V  Q  L  V  Q  S  G  S  E  L  K  K  P  G  A  S  V  K  L  S  C  K  A  S  G  F  T  F  T  Y  G
                                   10                                  20                                  30
       110                 120                 130                 140                 150                 160                 170                 180                 190                 200
TAAACTGGGTGAAGCAGGCCCCTGGACAGGGACTTGAGTGGATTGGATGGATTTATCCTAGAGATGGTAGTACTAACTTCAATGAGAATTTCAAGGACAG
 I  N  W  V  R  Q  A  P  G  Q  G  L  E  W  I  G  W  I  Y  P  R  D  G  S  T  N  F  N  E  N  F  K  D  R
                  40                                  50  52                                   60
                                                          a
       210                 220                 230                 240                 250                 260                 270                 280                 290                 300
GGCCACAATCACTGTAGACACATCCGCCAGCACAGCGTACATGGAACTCTCCAGCCTGAGATCTGAAGACACTGCGGTCTATTTCTGTGCAAGACTGACT
 A  T  I  T  V  D  T  S  A  S  T  A  Y  M  E  L  S  S  L  R  S  E  D  T  A  V  Y  F  C  A  R  L  T
     70                                  80  82                                   90
                                             a  b  c
       310                 320                 330                 340
GGTGGGACATTCCTTGACTATTGGGGCCAAGGGCACCACTGTCACAGTCTCCTCA
 G  G  T  F  L  D  Y  W  G  Q  G  T  T  V  T  V  S  S
             100                                  110
                 a
```

Figure 2B

DIVLTQSPATLSLSPGERATLSC<u>RASESVEYYGTSLMQ</u>WYQ
QKPGQPPKLLIF<u>GASNVES</u>GVPDRFSGSGSGTDFTLKISRVE
AEDVGMYFC<u>QQSRKLPWT</u>FGGGTKVEIKRTVAAPSVFIFPPS
DEQLKSGTASVVCLLNNFYPREAKVQWKVDNALQSGNSQE
SVTEQDSKDSTYSLSSTLTLSKADYEKHKVYACEVTHQGLSS
PVTKSFNRGEC

Figure 3 – SEQ ID NO:2

```
GACATTGTGCTCACCCAATCTCCAGCTACTTTGTCTCTGTCTCCAG
GGGAGAGAGCCACCCTCTCCTGCAGAGCCAGTGAAAGTGTTGAATA
CTATGGCACAAGTTTAATGCAGTGGTACCAACAGAAACCAGGACAG
CCACCCAAACTCCTCATCTTTGGTGCATCCAACGTAGAATCTGGGG
TCCCTGACAGGTTCAGTGGCAGTGGGTCTGGGACAGACTTCACCCT
CAAGATCAGCCGGGTGGAGGCCGAGGATGTTGGAATGTATTTCTGT
CAGCAAAGTAGGAAACTTCCGTGGACGTTCGGTGGAGGCACCAAGG
TGGAAATCAAACGTGAGTAGAATTTAAACTTTGCTTCCTCAGTTGG
ATCCCGCAATTCTAAACTCTGAGGGGGTCGGATGACGTGGCCATTC
TTTGCCTAAAGCATTGAGTTTACTGCAAGGTCAGAAAGCATGCAA
AGCCCTCAGAATGGCTGCAAAGAGCTCCAACAAAACAATTTAGAAC
TTTATTAAGGAATAGGGGGAAGCTAGGAAGAAACTCAAAACATCAA
GATTTTAAATACGCTTCTTGGTCTCCTTGCTATAATTATCTGGGAT
AAGCATGCTGTTTCTGTCTGTCCCTAACATGCCCTGTGATTATCC
GCAAACAACACACCCAAGGGCAGAACTTTGTTACTTAAACACCATC
CTGTTTGCTTCTTTCCTCAGGAACTGTGGCTGCACCATCTGTCTTC
ATCTTCCCGCCATCTGATGAGCAGTTGAAATCTGGAACTGCCTCTG
TTGTGTGCCTGCTGAATAACTTCTATCCCAGAGAGGCCAAAGTACA
GTGGAAGGTGGATAACGCCCTCCAATCGGGTAACTCCCAGGAGAGT
GTCACAGAGCAGGACAGCAAGGACAGCACCTACAGCCTCAGCAGCA
CCCTGACGCTGAGCAAAGCAGACTACGAGAAACACAAAGTCTACGC
CTGCGAAGTCACCCATCAGGGCCTGAGCTCGCCCGTCACAAAGAGC
TTCAACAGGGGAGAGTGTTAG
```

Figure 4 – SEQ ID NO:3

QVQLVQSGSELKKPGASVKLSCKASGFTFT<u>TYGIN</u>WVRQAPGQGLEWIG<u>WIYPRD
GSTNFNENFKD</u>RATITVDTSASTAYMELSSLRSEDTAVYFCAR<u>LTGGTFLDY</u>WGQ
GTTVTVS*SASTKGPSVFPLAPCSRSTSESTAALGCLVKDYFPEPVTVSWNSGALT
SGVHTFPAVLQSSGLYSLSSVVTVPSSSLGTKTYTCNVDHKPSNTKVDKRV***ESKY
GPPCPPCP**A<u>PEFLGGPSVFLFPPKPKDTLMI</u>SRT<u>PEVTCVVVDVSQEDPEVQFNW
YVDGVEVHNAKTKPREEQFNSTYRVVSVLTVLHQDWLNGKEYKCKVSNKGLPSSI
EKTISKAK</u>GQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNHYTQKSLS
LSLGK

Figure 5 – SEQ ID NO:5

```
CAGGTTCAGCTGGTGCAGTCTGGATCTGAGCTGAAGAAGCCTGGGGCGTCAGTGAAGTTG
TCCTGCAAGGCTTCTGGCTTCACCTTCACAACCTACGGTATAAACTGGGTGAGGCAGGCC
CCTGGACAGGGACTTGAGTGGATTGGATGGATTTATCCTAGAGATGGTAGTACTAACTTC
AATGAGAATTTCAAGGACAGGGCCACAATCACTGTAGACACATCCGCCAGCACAGCGTAC
ATGGAACTCTCCAGCCTGAGATCTGAAGACACTGCGGTCTATTTCTGTGCAAGACTGACT
GGTGGGACATTCCTTGACTATTGGGGCCAGGGCACCACTGTCACAGTCTCCTCAGGTAAG
CTTTCTGGGGCAGGCCGGGCCTGACTTTGGCTGGGGGCAGGGAGGGGGCTAAGGTGACGC
AGGTGGCGCCAGCCAGGTGCACACCCAATGCCCATGAGCCCAGACACTGGACCCTGCATG
GACCATCGCGGATAGACAAGAACCGAGGGGCCTCTGCGCCCTGGGCCCAGCTCTGTCCCA
CACCGCGGTCACATGGCACCACCTCTCTTGCAGCTTCCACCAAGGGCCCATCCGTCTTCC
CCCTGGCGCCCTGCTCCAGGAGCACCTCCGAGAGCACAGCCGCCCTGGGCTGCCTGGTCA
AGGACTACTTCCCCGAACCGGTGACGGTGTCGTGGAACTCAGGCGCCCTGACCAGCGGCG
TGCACACCTTCCCGGCTGTCCTACAGTCCTCAGGACTCTACTCCCTCAGCAGCGTGGTGA
CCGTGCCCTCCAGCAGCTTGGGCACGAAGACCTACACCTGCAATGTAGATCACAAGCCCA
GCAACACCAAGGTGGACAAGAGAGTTGGTGAGAGGCCAGCACAGGGAGGGAGGGTGTCTG
CTGGAAGCCAGGCTCAGCCCTCCTGCCTGGACGCACCCCGGCTGTGCAGCCCCAGCCCAG
GGCAGCAAGGCAGGCCCCATCTGTCTCCTCACCTGGAGGCCTCTGACCACCCCACTCATG
CTCAGGGAGAGGGTCTTCTGGATTTTTCCACCAGGCTCCGGGCAGCCACAGGCTGGATGC
CCCTACCCCAGGCCCTGCGCATACAGGGGCAGGTGCTGCGCTCAGACCTGCCAAGAGCCA
TATCCGGGAGGACCCTGCCCCTGACCTAAGCCCACCCCAAAGGCCAAACTCTCCACTCCC
TCAGCTCAGACACCTTCTCTCCTCCCAGATCTGAGTAACTCCCAATCTTCTCTCTGCAGA
GTCCAAATATGGTCCCCCATGCCCACCATGCCCAGGTAAGCCAACCCAGGCCTCGCCCTC
CAGCTCAAGGCGGGACAGGTGCCCTAGAGTAGCCTGCATCCAGGGACAGGCCCCAGCCGG
GTGCTGACGCATCCACCTCCATCTCTTCCTCAGCACCTGAGTTCCTGGGGGGACCATCAG
TCTTCCTGTTCCCCCCAAAACCCAAGGACACTCTCATGATCTCCCGGACCCCTGAGGTCA
CGTGCGTGGTGGTGGACGTGAGCCAGGAAGACCCCGAGGTCCAGTTCAACTGGTACGTGG
ATGGCGTGGAGGTGCATAATGCCAAGACAAAGCCGCGGGAGGAGCAGTTCAACAGCACGT
ACCGTGTGGTCAGCGTCCTCACCGTCCTGCACCAGGACTGGCTGAACGGCAAGGAGTACA
AGTGCAAGGTCTCCAACAAAGGCCTCCCGTCCTCCATCGAGAAAACCATCTCCAAAGCCA
AAGGTGGGACCCACGGGGTGCGAGGGCCACATGGACAGAGGTCAGCTCGGCCCACCCTCT
GCCCTGGGAGTGACCGCTGTGCCAACCTCTGTCCCTACAGGGCAGCCCCGAGAGCCACAG
GTGTACACCCTGCCCCCATCCCAGGAGGAGATGACCAAGAACCAGGTCAGCCTGACCTGC
CTGGTCAAAGGCTTCTACCCCAGCGACATCGCCGTGGAGTGGGAGAGCAATGGGCAGCCG
GAGAACAACTACAAGACCACGCCTCCCGTGCTGGACTCCGACGGCTCCTTCTTCCTCTAC
AGCAGGCTAACCGTGGACAAGAGCAGGTGGCAGGAGGGGAATGTCTTCTCATGCTCCGTG
ATGCATGAGGCTCTGCACAACCACTACACACAGAAGAGCCTCTCCCTGTCTCTGGGTAAA
TGA
```

Figure 6 – SEQ ID NO:6

```
  1 mphtlwmvwv lgviiislske essnqaslsc drngickgss gslnsipsgl teavksldls
 61 nnrityisns dlqrcvnlqa lvltsngint ieedsfsslg slehldlsyn ylsnlssswf
121 kplssltfln llgnpyktlg etslfshltk lqilrvgnmd tftkiqrkdf agltfleele
181 idasdlqsye pkslksiqnv shlilhmkqh illleifvdv tssveclelr dtdldtfhfs
241 elstgetnsl ikkftfrnvk itdeslfqvm kllnqisgll elefddctln gvgnfrasdn
301 drvidpgkve tltirrlhip rfylfydlst lysltervkr itvenskvfl vpcllsqhlk
361 sleyldlsen lmveeylkns acedawpslq tlilrqnhla slektgetll tlknltnidi
421 sknsfhsmpe tcqwpekmky lnlsstrihs vtgcipktle ildvsnnnln lfslnlpqlk
481 elyisrnklm tlpdasllpm llvlkisrna ittfskeqld sfhtlktlea ggnnficsce
541 flsftqeqqa lakvlidwpa nylcdspshv rgqqvqdvrl svsechrtal vsgmccalfl
601 lilltgvlch rfhglwymkm mwawlqakrk prkapsrnic ydafvsyser daywvenlmv
661 qelenfnppf klclhkrdfi pgkwiidnii dsiekshktv fvlsenfvks ewckyeldfs
721 hfrlfeennd aailillepi ekkaipqrfc klrkimntkt ylewpmdeaq regfwvnlra
781 aiks
```

Figure 7 – Amino acid sequence of human TLR2

```
  1 mlralwlfwi lvaitvlfsk rcsaqeslsc dasgvcdgrs rsftsipsgl taamksldls
 61 fnkityighg dlracanlqv lmlkssrint iegdafyslg slehldlsdn hlsslssswf
121 gplsslkyln lmgnpyqtlg vtslfpnltn lqtlrignve tfseirridf agltslnele
181 ikalslrnyq sqslksirdi hhltlhlses aflleifadi lssvrylelr dtnlarfqfs
241 plpvdevssp mkklafrgsv ltdesfnell kllryilels evefddctln glgdfnpses
301 dvvselgkve tvtirrlhip qfylfydlst vysllekvkr itvenskvfl vpcsfsqhlk
361 slefldlsen lmveeylkns ackgawpslq tlvlsqnhlr smqktgeill tlknltsldi
421 srntfhpmpd scqwpekmrf lnlsstgirv vktcipqtle vldvsnnnld sfslflprlq
481 elyisrnklk tlpdaslfpv llvmkirena vstfskdqlg sfpkletlea gdnhfvcsce
541 llsftmetpa laqilvdwpd sylcdspprl hghrlqdarp svlechqaal vsgvccalll
601 lillvgalch hfhglwylrm mwawlqakrk pkkapcrdvc ydafvsyseq dshwvenlmv
661 qqlensdppf klclhkrdfv pgkwiidnii dsiekshktv fvlsenfvrs ewckyeldfs
721 hfrlfdennd aailvllepi erkaipqrfc klrkimntkt ylewpldegq qevfwvnlrt
781 aiks
```

Figure 8 – Amino acid sequence of murine TLR2

```
T2.5      1 DIVLTQSPASLAVSLGQRATISCRASESVEYYGTSLMQWYQQKPGQPPKLLIFGASNVES
OPN-305   1 DIVLTQSPASLALSLGERATLSCRASESVEYYGTSLMQWYQQKPGQPPKLLIFGASNVES
            ************ *** *** ***************************************

T2.5     61 GVPVRFSGSGSGTDFSLNIHPVEEDDIVMYFCQQSRKLPWTFGGGTKLEIK
OPN-305  61 GVPDRFSGSGSGTDFTLKISRVEEEDVGMYFCQQSRKLPWTFGGGTKVEIK
            *** ***********  *  *** *  ******************* ***

89.2% identity in 111 residues overlap; Score: 523.0; Gap frequency: 0.0%
```

Figure 19

```
T2.5     1 QVQLQQSGPELVNPGASVKLSCKASGFTFTTYGINWVKQGPGQGLEWIGWIYPRDGSTNF
OPN-305  1 QVQLVQSGSELKKPGASVKLSCKASGFTFTTYGINWVRQAPGQGLEWIGWIYPRDGSTNF
           **** *** **  ******************** * ************************

T2.5    61 NENFKDKAALTVDTSSSTAYMELHSLTSEDSAVYFCARLTGGTFLDYWGQGTTLTVSS
OPN-305 61 NENFKDRATITVDTSASTAYMELSSLRSEDTAVYFCARLTGGTFLDYWGQGTTVTVSS
           ****** * ***** ******* ** *** ********************** ****

88.1% identity in 118 residues overlap; Score: 563.0; Gap frequency: 0.0%
```

Figure 20

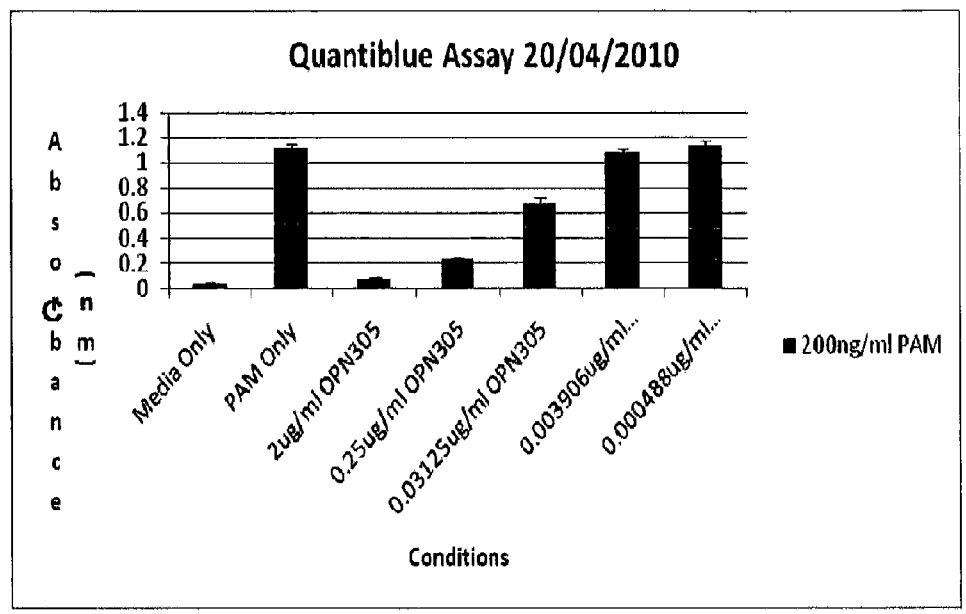
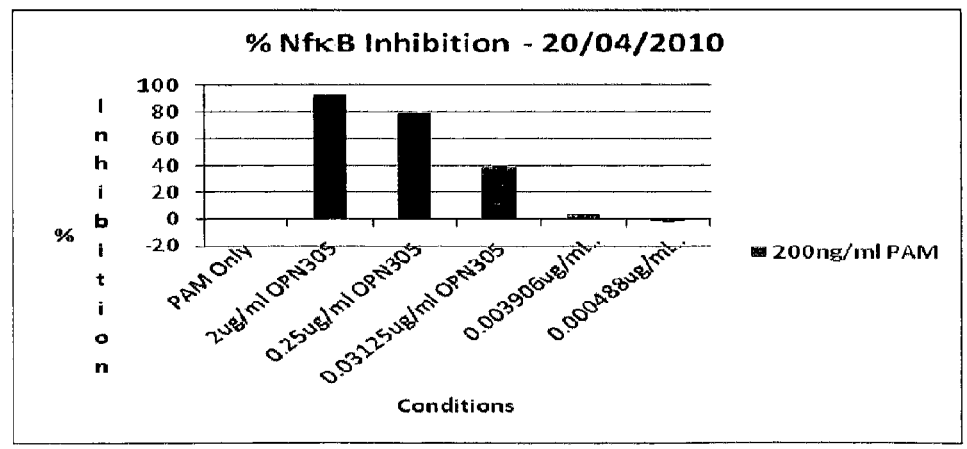
Figure 21A, B

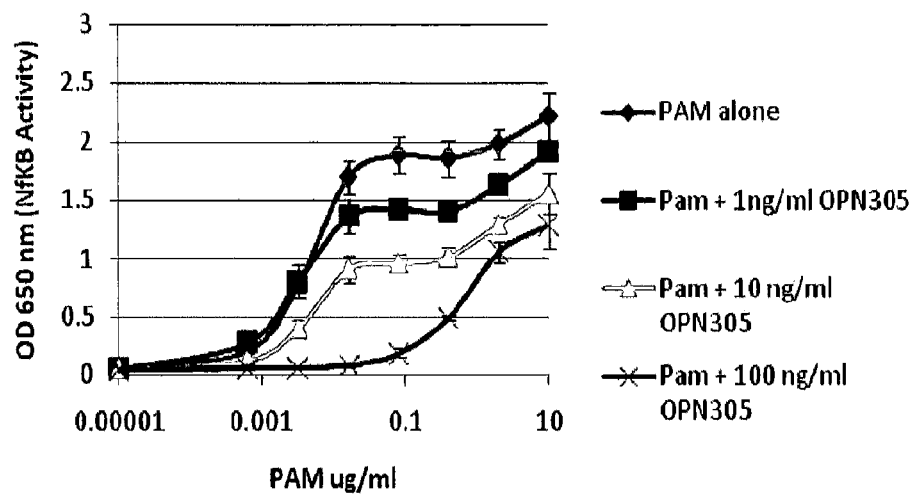
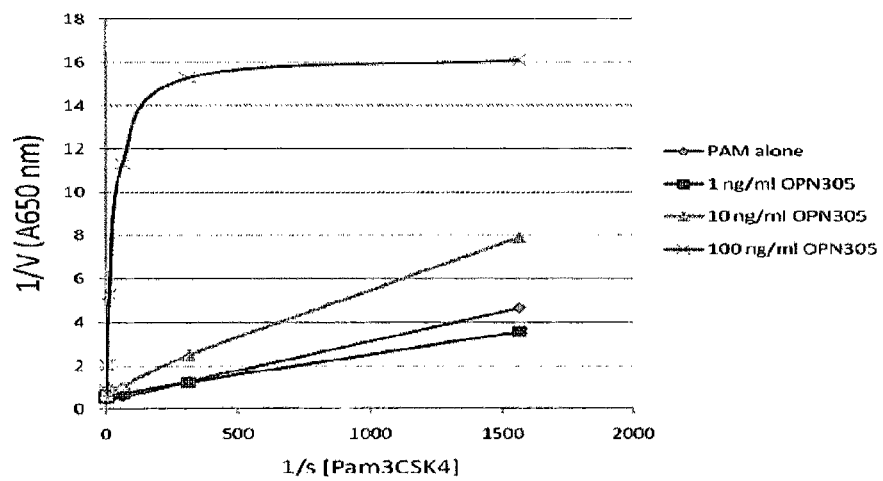
Figure 22

HUMANISED ANTIBODIES TO TOLL-LIKE RECEPTOR 2 AND USES THEREOF

This application is a U.S. National Phase of International Application No. PCT/EP2010/059677, filed Jul. 6, 2010; which claims priority to Irish Patent Application No. 2009/0514, filed Jul. 6, 2009 and U.S. Patent Application No. 61/270,239, filed Jul. 6, 2009, the entire disclosures of which are incorporated herein by reference.

FIELD OF THE INVENTION

The present invention relates to fully humanised antibodies and fragments thereof, and in particular, to fully humanised antibodies which have binding specificity for Toll-like Receptor 2 (TLR2, TLR-2). The invention further extends to the use of said fully humanised antibodies for the treatment and prevention of inflammatory and autoimmune diseases mediated by Toll-like Receptor 2 activation and signalling.

BACKGROUND TO THE INVENTION

Toll-like Receptors (TLRs) form a family of pattern recognition receptors which have a key role in modulating the innate immune response, they are also involved in tissue repair, maintenance of tissue integrity and tumorigenesis. Eleven Toll-like Receptors have been identified in humans to date. The members of the Toll-like Receptor family are highly conserved, with most mammalian species having between 10 to 15 Toll-like Receptors. Each Toll-like Receptor recognises specific pathogen-associated molecular signatures. Toll-like Receptor 2 (TLR2, CD282, TLR-2) can be activated by peptidoglycan, lipoproteins, lipoteichoic acid and endogenous ligands.

A number of monoclonal antibodies which have binding specificity for Toll-like Receptor 2 are known. WO 01/36488 discloses an antibody, designated as TL2.1, which is derived from a hybridoma cell line deposited in accordance with the Budapest Treaty at the European Collection of Cell Cultures (ECACC) under the accession number 99102832. This antibody antagonises the activation of Toll-like Receptor 2 expressed on human cells.

WO 2005/028509 discloses a murine monoclonal antibody, designated T2.5, which specifically inhibits the activation of mammalian TLR2. The T2.5 monoclonal antibody is shown to be cross-reactive to both human and murine forms of TLR2. This document further contains experimental data which suggests that the murine TL2.1 anti-TLR2 monoclonal antibody, as disclosed in WO 01/36488, is not cross-reactive to both human and murine forms of TLR2, as was stated in the description of that patent application. Rather, the TL2.1 antibody is shown in WO 2005/028509 as only binding to human Toll-like Receptor 2 and not murine Toll-like Receptor 2. The T2.5 monoclonal antibody of WO 2005/028509 was raised against the extracellular domain of TLR2, and therefore has binding specificity to an epitope in that area of Toll-like Receptor 2.

WO 2005/019431 discloses an antibody which has binding specificity to TLR2, which is designated 11G7. This murine antibody can be derived from hybridoma cell line 11G7 as deposited with the American Type Culture Centre (ATCC) under the designation PTA-5014. The 11G7 monoclonal antibody selectively binds to the extracellular domain of TLR2 and can block the induction of cytokine production by human peripheral blood mononuclear cells (PBMCs) stimulated with an agonist which activates a heterodimer formed between Toll-like Receptor 1 (TLR1) and TLR2. The 11G7 antibody does not inhibit cytokine production by PBMCs stimulated with an agonist which induces signalling through a heterodimer formed between Toll-like Receptor 6 (TLR6) and TLR2.

The use of rodent monoclonal antibodies, such as murine monoclonal antibodies, for in-vivo therapeutic applications has been shown to be associated with the generation of undesirable immune responses which are generated by the subject to whom the antibody is administered. Such immune responses can result in the production of antibodies which effectively neutralise the effectiveness of the therapeutic antibody. Such immune responses are typically referred to as human anti-mouse antibody (HAMA) responses. HAMA responses compromise the therapeutic effectiveness of the administered antibody in a number of ways, including impairing the ability of the therapeutic antibody to reach its binding target, this compromising the therapeutic effect of the antibody.

A number of approaches have been developed to address the issue of unwanted HAMA responses being raised against therapeutic antibodies which are administered to individuals. Typically, these approaches involve techniques which result in the replacement of certain components of the mouse antibody with equivalent portions derived from a human antibody. Such approaches can, for example, result in the production of chimeric antibodies which comprise murine variable regions joined to human-derived constant regions. Alternatively, a technique known as "CDR grafting" can be employed, wherein the complementarity determining regions (CDRs) from a murine antibody are grafted into a framework provided by regions of human antibody light and heavy chain variable domains. This results in the production of an antibody which retains the binding specificity of the murine antibody, but where the only non-human components are the grafted murine CDRs regions.

However, in both of these approaches, the therapeutic effectiveness of the resulting humanised antibody can be impaired. For example, the murine variable region component of a chimeric antibody can still provide the basis for a HAMA response to be mounted there against. Further, where CDR grafted humanised antibodies are produced, it has been observed that simple transplantation of the CDR regions often results in a reduced therapeutic efficacy of the antibody due to the binding affinity of the antibody being diminished.

The inventor has therefore identified the need to generate fully humanised monoclonal antibodies which have binding specificity for Toll-like Receptor 2, and which antagonise TLR2 function, but which are essentially non-immunogenic in humans. Following extensive experimentation, the inventor has produced a fully humanised monoclonal antibody which have binding specificity to human Toll-like Receptor 2, and which antagonises TLR2 function irrespective of whether Toll-like Receptor 2 forms a heterodimer with Toll-like Receptor 1 or Toll-like Receptor 6. This TLR2 antagonistic antibody is not produced from previously known chimeric or CDR-grafting techniques and therefore does not contain any murine amino acid residues. Furthermore, the antibody is shown to mediate TLR2 neutralisation without the need to bind to the CD32 cell surface antigen, this being a functional requirement of other known Toll-like Receptor 2 antagonistic antibodies. Furthermore, the fully humanised antibody of the invention is the first fully human TLR2 neutralising antibody to be known in the art. The antibody does not exhibit any T cell epitopes and therefore neutralising antibodies are not raised there against when administered to a subject. The anti-TLR2 antagonistic antibodies further exhibit a broad level of cross-reactivity to Toll-like Receptor 2 as expressed by a wide range of mammalian cells, with binding of the fully humanised antibody being surprisingly observed to bind to Toll-like Receptor 2 expressed on human, mouse and monkey cells.

SUMMARY OF THE INVENTION

According to a first aspect of the invention there is provided a neutralising antibody, or an antigen binding portion thereof, which is capable of specifically binding to Toll-like Receptor 2 (TLR2, CD282, TLR-2), and wherein the antibody or antigen binding portion comprises, consists or consists essentially of a light chain and a heavy chain wherein the variable region of the light chain (VL) comprises an amino acid sequence which is identical or substantially homologous to the amino acid sequence of SEQ ID NO:1, and wherein the variable region of the heavy chain (VH) comprises, consists or consists essentially of an amino acid sequence which is identical or substantially homologous to the amino acid sequence of SEQ ID NO:4.

As defined herein, the term neutralising antibody describes an antibody that is capable of neutralising the biological activation and signalling of Toll-like Receptor 2. The neutralising antibody, which may also be referred to as an antagonistic antibody, or a blocking antibody, specifically and preferably selectively, binds to Toll-like Receptor 2 and inhibits one or more biological activities of Toll-like Receptor 2. For example, the neutralising antibody may inhibit the binding of a ligand or substrate, such as a Toll-like Receptor 2 ligand, to the Toll-like Receptor 2 ligand binding site. Alternatively, the neutralising antibody may prevent the activation of Toll-like Receptor 2 once bound by a ligand agonist, for example by impairing ligand agonist binding. Typically the neutralising antibody selectively binds Toll-like Receptor 2 and, therefore, does not substantially bind other Toll-like Receptor family members (e.g., Toll-like Receptor 4) under physiological or therapeutic conditions.

In certain embodiments, the Toll-like Receptor 2 neutralising antibody mediates antagonism of Toll-like Receptor 2 functional activity independently of the requirement of the anti-Toll-like Receptor 2 antibody, or binding fragment, to bind to CD32 (Fc gamma receptor II (FcγRII, FcgRII), in particular CD32a and/or CD32b. Accordingly, the neutralisation of Toll-like Receptor 2 does not require binding of the antibody, and in particular the Fc portion of the antibody, or antibody fragment, to CD32.

Typically the anti-Toll-like Receptor 2 antibodies of the invention are characterised in that they do not contain any binding epitopes against which an immune response can be mediated when the antibody is administered to a subject, in particular a human. Such a characteristic is important in preventing the generation of neutralising antibodies against the antibodies of the invention in the subject to whom the antibodies are administered, as the therapeutic efficacy of the antibodies can be severely impaired should such an immune response occur.

Typically, the neutralising anti-Toll-like Receptor 2 antibody is a fully humanised antibody. That is, all the combinations of amino acid residues which comprise the antibody are entirely of human origin, and do not therefore contain, for example, human and non-human regions. In particular, the antibody of the invention comprises human variable region sequences only. The antibody of the invention therefore differs from, for example, a chimeric monoclonal antibody which consists of amino acid residues derived from both mice and humans at the variable regions of the heavy and light chains, or from a CDR-grafted "humanised" antibody, where the complementarity determining regions (CDRs) of the heavy and light chain variable regions comprise amino acid residues derived from a murine antibody, while the associated framework regions (FR) of the antibody and the constant regions (CR) are derived from a human antibody. Hence, the fully humanised antibody of the invention has variable and constant regions, of both the heavy and light chains, which are all of human origin, or which are substantially identical to sequences of human origin, albeit not necessarily from the same antibody. The fully humanised antibodies of the invention may be further referred to as "humanised" antibodies, or as an antibody derived fully from human sequences.

The amino acid sequence of the variable region of the light chain (VL) of the antibody of the invention is shown below as SEQ ID NO:1:

DIVLTQSPATLSLSPGERATLSCRASESVEYYGTSLMQWYQQKPGQPPKL

LIFGASNVESGVPDRFSGSGSGTDFTLKISRVEAEDVGMYFCQQSRKLPW

TFGGGTKVEIK

In SEQ ID NO:1, as shown in FIG. 1, the underlined residues relate to the location of complementarity determining regions, wherein residues 24 to 34 relate to CDR1, residues 50 to 56 relate to CDR2 and residues 89 to 97 relate to CDR3. FIG. 1B shows the variable light chain nucleotide sequence and the deduced amino acid sequence. In this figure, the residues of the light chain domain are conventionally numbered according to the Kabat numbering system (Kabat E A et al. (1991) Sequences of proteins of immunological interest, 5$^{th}$ edition. Bethesda: US Department of Health and Human Services).

It should be noted that the identification of these CDR residues is consistent with the residues assigned to the CDR regions using the Kabat numbering system, wherein VLCDR1 (i.e. complementarity determining region 1 of the light chain variable domain) comprises residues 24 to 34, VLCDR2 (complementarity determining region 1 of the light chain variable domain) comprises residues 50 to 56 and VLCDR3 (complementarity determining region 1 of the light chain variable domain) comprises residues 89 to 97.

As herein defined, an amino acid sequence which is substantially homologous to the amino acid sequence of SEQ ID NO:1 means an amino acid sequence which has at least 90% amino acid sequence identity, more preferably 95% sequence identity, and most preferably at least 98% amino acid identity over a length of at least 20, 50 or 100 amino acids, or of the entire sequence length, to the amino acid sequence of SEQ ID NO:1. Typically such homologous amino acid sequences will have binding specificity for Toll-like Receptor 2 and, when bound to Toll-like Receptor 2, will antagonise Toll-like Receptor 2 functional activity.

Typically, the variable region of the light chain (VL) is joined to a human immunoglobulin Kappa constant domain (CL) to provide a light chain, said light chain being the light chain of the humanised antibody.

Accordingly, in certain embodiments, where the antibody or binding member of the invention comprises a complete light chain, the light chain has the amino acid sequence of SEQ ID NO:2:

DIVLTQSPATLSLSPGERATLSCRASESVEYYGTSLMQWYQQKPGQPPKL

LIFGASNVESGVPDRFSGSGSGTDFTLKISRVEAEDVGMYFCQQSRKLPW

TFGGGTKVEIKRTVAAPSVFIFPPSDEQLKSGTASVVCLLNNFYPREAKVQ

-continued

WKVDNALQSGNSQESVTEQDSKDSTYSLSSTLTLSKADYEKHKVYACEVT

HQGLSSPVTKSFNRGEC

In certain further embodiments, the invention extends to an antibody or binding member comprising a light chain which comprises, consists or consists essentially of an amino acid sequence having an identity of at least 80%, more preferably at least 90%, more preferably at least 95% and most preferably 98% identity to the amino acid sequence of SEQ ID NO:2. Typically the antibody which comprises the amino acid sequence which has at least 80% or greater amino acid identity with SEQ ID NO:2 will specifically bind to Toll-like Receptor 2 and when bound thereto, will serve to antagonise Toll-like Receptor 2 functional activity.

In certain embodiments, the amino acid sequence of the light chain, as defined in SEQ ID NO:2 and as depicted in FIG. 3, is encoded from the nucleotide sequence of SEQ ID NO:3 as shown in FIG. 4. In the sequence of SEQ ID NO:3 shown in FIG. 4, the underlined nucleic acids encode the amino acids of the light chain variable region.

In one embodiment, the amino acid sequence of the variable region of the heavy chain (VH) is shown below as SEQ ID NO:4:

QVQLVQSGSELKKPGASVKLSCKASGFTFTTYGINWVRQAPGQGLEWIGW

IYPRDGSTNFNENFKDRATITVDTSASTAYMELSSLRSEDTAVYFCARLT

GGTFLDYWGQGTTVTVSS

In SEQ ID NO:4 as shown in FIG. 2, the underlined residues relate to the amino acid residues of the 3 complementarity determining regions, wherein residues 31 to 35 relate to CDR1 (VHCDR1 (complementarity determining region 1 of the heavy chain variable domain)), residues 50 to 65 relate to CDR2 (VHCDR2) and residues 95 to 103 relate to CDR3 (VHCDR3). It should be noted that the positioning of these CDR residues differs slightly to the positioning typically ascribed to the CDR regions using the Kabat numbering system, wherein CDR1 is present at residues 31 to 35, CDR2 is present at residues 50 to 66, and CDR3 is present at residues 95 to 103.

As herein defined, an amino acid sequence which is substantially homologous to the amino acid sequence of SEQ ID NO:4 means an amino acid sequence which has at least 90% amino acid sequence identity, more preferably 95% sequence identity, and most preferably at least 98% amino acid identity over a length of at least 20, 50 or 100 amino acids of the amino acid sequence of SEQ ID NO:4. In certain further embodiments, the invention extends to an antibody or binding member comprising a heavy chain variable (VH) domain which comprises, consists or consists essentially of an amino acid sequence homology of at least 80%, more preferably at least 90%, more preferably at least 95% and most preferably 98% sequence identity to the amino acid sequence of SEQ ID NO:4.

Typically, the variable region of the heavy chain (VH) is conjoined to a further amino acid sequence which comprises at least one immunoglobulin constant domain. In certain embodiments, the immunoglobulin constant domain is derived from an antibody of the subclass IgG (immunoglobulin G) to form the complete heavy chain of the humanised antibody of the invention. Accordingly, said constant domain may comprise CH1, CH2 and CH3 along with a suitable linker located between said CH1 and CH2 domains.

In certain embodiments the immunoglobulin constant domains are derived from an immunoglobulin of the IgG isotype, typically immunoglobulin G, isotype 4 (IgG4). IgG4 antibodies are dynamic molecules which exchange Fab arms by swapping a heavy chain and attached light chain (half-molecule) with a heavy-light chain pair from another molecule, this exchange resulting in the production of bi-specific antibodies. Accordingly, in certain embodiments, at least one mutation is made to the amino acid sequence of at least one of the constant domains of the IgG4 immunoglobulin in order to prevent Fab arm exchange occurring. Accordingly, in certain embodiments of the invention, where an antibody or antibody fragment comprises constant domains derived from IgG4, a mutation of amino acid residue 241 of the heavy chain, located at the hinge region, would be performed such that the serine residue is substituted to a proline residue (S241P) (as taught in Angal S. et al. Molecular Immunology. 1993. Vol. 30. No. 1. p 105-108).

Accordingly, in certain embodiments, the amino acid residues used to provide the heavy and light chain constant domain residues are derived from an immunoglobulin of the isotype IgG4. In certain further embodiments, the immunoglobulin is derived from an immunoglobulin of the subclass IgG and of the isotype IgG1, IgG2 or IgG3. In certain further embodiments, the amino acid residues used to provide the heavy and light chain constant domain residues are derived from an immunoglobulin of the subtype IgA.

In various further embodiments, one or more mutations, substitutions, deletions or insertions may be made to the amino acid sequence of the constant domain of the antibody in order to modify the functional properties of the antibody. For example, at least one amino acid mutation, insertion, deletion and/or substitution may be made to the amino acid residues of a constant domain to modify at least one property selected from, but not limited to: the effector function, potency or half life properties of the antibody.

In certain embodiments, the amino acid sequence of the heavy chain of an antibody according to the present invention, which comprises the domains VH-CH1-CH2-CH3 and which further includes a hinge region, is provided below as SEQ ID NO:5:

QVQLVQSGSELKKPGASVKLSCKASGFTFTTYGINWVRQAPGQGLEWIGW

IYPRDGSTNFNENFKDRATITVDTSASTAYMELSSLRSEDTAVYFCARLT

GGTFLDYWGQGTTVTVSSASTKGPSVFPLAPCSRSTSESTAALGCLVKDY

FPEPVTVSWNSGALTSGVHTFPAVLQSSGLYSLSSVVTVPSSSLGTKTYTC

NVDHKPSNTKVDKRVESKYGPPCPPCPAPEFLGGPSVFLFPPKPKDTLMI

SRTPEVTCVVVDVSQEDPEVQFNWYVDGVEVHNAKTKPREEQFNSTYRVV

SVLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSFF

LYSRLTVDKSRWQEGNVFSCSVMHEALHNHYTQKSLSLSLGK

In certain further embodiments, the invention extends to an antibody or binding member comprising a heavy chain which comprises a homologous amino acid sequence having an amino acid sequence identity of at least 80%, more preferably at least 90%, more preferably at least 95% and most preferably 98% to the amino acid sequence of SEQ ID NO:5.

In certain embodiments, the amino acid sequence of the heavy chain, as defined in SEQ ID NO:5 and as depicted in FIG. 5, is encoded from the nucleotide sequence of SEQ ID NO:6 as shown in FIG. 6. In the sequence of SEQ ID NO:5 as shown in FIG. 5, the residues in bold are the hinge region, the residues in italics are the residues of the CH1 constant domain, the underlined residues are the residues of the CH2 constant domain and the residues listed after the underlined residues are the residues of the CH3 constant domain. In certain embodiments, the CH1, CH2 and/or CH3 constant domains may be substituted, in whole, or in part with a CH1, CH2 or CH3 domain derived from any suitable immunoglobulin subtype, such as, but not limited to IgG1, IgG2, IgA, or IgM. In certain embodiments, the deletion, addition or substitution of at least one amino acid residue present in any of the constant domains, may also be provided. Typically said deletions, additions or substitutions cause a resulting functional change in the binding properties of the Fc portion of the antibody, or antibody fragment, and in particular a modulation of the ability of the Fc region of the antibody to bind to Fc receptor and mediate effector functions.

In certain further embodiments, the present invention extends to an isolated antibody comprising a light chain variable domain of SEQ ID NO:1, or a variant which has at least 90% amino acid sequence identity thereto, and a heavy chain variable domain of SEQ ID NO:4, or a variant which has at least 90% amino acid sequence homology identity thereto.

In certain further embodiments, there is provided an antibody formed of a light chain comprising the amino sequence of SEQ ID NO:2, or a variant having at least 90% sequence identity thereto, and a heavy chain having the amino acid sequence on SEQ ID NO:5, or a variant which has at least 90% amino acid sequence identity thereto.

It will be appreciated that the variable and constant domains of both the light and heavy chains for use in producing the antibodies and antibody fragments of the present invention, may include variants of these domains, for example, said variable and constant domains may comprise one or more amino acid variations compared to the sequence of these domains as described herein. It will be appreciated that the variant constant domains may be longer or shorter than the constant domains described herein. In certain embodiments, the variant variable or constant domains may have a sequence homology of at least 90% identity or similarity to a wild type antibody constant domain.

As herein defined "sequence homology" may also be referred to as sequence identity or sequence similarity. The term "identity" or "sequence identity" as used herein, means that at any particular position in the aligned sequence, the amino acid residue is identical between the aligned sequences. The term "similarity" or "sequence similarity" as used herein, indicates that, at any particular position in the aligned sequences, the amino acid residue is of a similar type between the sequences. For example, leucine may be substituted for an isoleucine or valine residue. This may be referred to as conservative substitution. Preferably when the amino acid sequences of the invention are modified by way of conservative substitution of any of the amino acid residues contained therein, these changes have no effect on the binding specificity or functional activity of the resulting antibody when compared to the unmodified antibody.

Sequence homology, or sequence identity with respect to a (native) polypeptide of the invention and its functional derivative relates to the percentage of amino acid residues in the candidate sequence which are identical with the residues of the corresponding native polypeptide, after aligning the sequences and introducing gaps, if necessary, to achieve the maximum percentage homology, and not considering any conservative substitutions as part of the sequence identity. Neither N- or C-terminal extensions, nor insertions shall be construed as reducing sequence identity or homology. Methods and computer programs for performing an alignment of two or more amino acid sequences and determining their sequence identity or homology are well known to the person skilled in the art. For example, the percentage of identity or similarity of 2 amino acid sequences can be readily calculated using algorithms e.g. BLAST (Altschul et al. 1990), FASTA (Pearson & Lipman 1988), or the Smith-Waterman algorithm (Smith & Waterman 1981).

In a further aspect, the present invention provides a fully humanised antibody which has binding specificity for the epitope present on Toll-like Receptor 2 which is recognised by the murine monoclonal antibody T2.5, wherein said human antibody comprises:
  a light chain variable wherein the variable region comprises, consists or consists essentially of the amino acid sequence of SEQ ID NO:1,
  a heavy chain wherein the variable domain comprises, consists or consists essentially of the amino acid sequence of SEQ ID NO:4.

In certain embodiments, the antibody may be conjugated to at least one effector or reporter molecule.

In certain further aspects, the present invention extends to a fully humanised monoclonal antibody, designated OPN-305, which comprises a light chain variable region having the amino acid sequence of SEQ ID NO:1 and a heavy chain variable domain having the amino acid sequence of SEQ ID NO:4. The OPN-305 antibody may be further defined as having a light chain consisting of, or consisting essentially of the amino acid sequence of SEQ ID NO:2 and a heavy chain consisting of, or consisting essentially of the amino acid sequence of SEQ ID NO:5.

The term "consists essentially of" or "consisting essentially of" as used herein means that a polypeptide may have additional features or elements beyond those described provided that such additional features or elements do not materially affect the ability of the antibody or antibody fragment to have binding specificity to Toll-like Receptor 2. That is, the antibody or antibody fragments comprising the polypeptides may have additional features or elements that do not interfere with the ability of the antibody or antibody fragments to bind to Toll-like Receptor 2 and antagonise Toll-like Receptor 2 functional activity, such as modifications introduced into the amino acid sequence in order to reduce the immunogenicity of the antibody. For example, a polypeptide consisting essentially of a specified sequence may contain one, two, three, four, five or more additional amino acids, at either end or at both ends of the sequence provided that the additional amino acids do not interfere with, inhibit, block or interrupt the role of the polypeptide in an antibody or antibody fragment. Similarly, a polypeptide molecule which contributes to the Toll-like Receptor 2 antagonistic antibodies of the invention may be chemically modified with one or more functional groups provided that such functional groups do not interfere with the ability of the antibody or antibody fragment to bind to Toll-like Receptor 2 and antagonise its function.

In certain further aspects, the present invention extends to an isolated, fully humanised, monoclonal antibody, which comprises a light chain variable region comprising, consisting or consisting essentially of the amino acid sequence of SEQ ID NO:1 and/or a heavy chain variable domain having the amino acid sequence of SEQ ID NO:4.

As defined herein a "fully humanised" antibody refers to an antibody having variable regions in which framework regions (FR), constant regions (CR) and the complementarity determining regions (CDR) are derived from human germline immunoglobulin sequences. Furthermore, if the antibody contains constant regions, then these constant regions are also derived from human germline immunoglobulin sequences. The fully humanised antibodies of the invention may include amino acid residues not encoded by human immunoglobulin sequences, such as mutations introduced by random, or site-specific mutagenesis in-vitro. However, a fully humanised antibody is not intended to include antibodies in which CDR sequences derived from the germline of other mammalian species, such as mice, have been grafted onto human framework sequences. A fully humanised monoclonal antibody is an antibody which displays a single binding specificity and which has variable regions in which both framework and CDR regions are derived from human germline immunoglobulin sequences. This differs from, for example, a humanised monoclonal antibody, where CDR sequences derived from the germline of another mammalian species, such as a mouse, have been grafted onto human framework sequences.

In embodiments where only the amino acid sequence of the variable heavy (VH) or variable light (VL) sequence are provided, then the invention extends to methods for producing antibodies which bind to the extracellular domain of Toll-like Receptor 2, in particular, mammalian Toll-like Receptor 2, typically human Toll-like Receptor 2, wherein said antibodies function to antagonise Toll-like Receptor 2 function, by screening said variable domain sequences against a library of complimentary variable domain sequences according to the teachings of Portolano et al. (Portolano et al. The Journal of Immunology (1993). 150:880-887) and Clarkson et al. (Clarkson et al. Nature (1991) 352: 624-628).

In certain further embodiments, the present invention provides an isolated antibody that specifically binds to human Toll-like Receptor 2, said antibody comprising a heavy chain variable domain comprising, consisting, or consisting essentially of the amino acid sequence of SEQ ID NO:4 and a light chain variable domain comprising, consisting or consisting essentially of the amino acid of SEQ ID NO:1. In certain embodiments, the isolated antibody is a substantially pure, isolated antibody that is substantially free of other antibodies having different antigenic specificities. In certain further embodiments, the antibody is a recombinant antibody, that is, that the antibody has been made by recombinant methods.

In certain further aspects, there is provided an antibody which specifically binds to Toll-like Receptor 2, wherein the antibody consists, or consists essentially of a light chain having the amino acid sequence of SEQ ID NO:2 and a heavy chain having the amino acid sequence of SEQ ID NO:5, wherein the antibody is cross-reactive (that is, that it has binding specificity) to Toll-like Receptor 2 expressed on human, murine and monkey cells. Typically the antibody binds to Toll-like Receptor 2 at a ligand binding site which, when bound by the antibody, prevents the activation of Toll-like Receptor 2 by a ligand agonist binding to the ligand binding site of Toll-like Receptor 2.

In various further aspects, the present invention extends to a multivalent monospecific antigen binding protein comprising two, three, four or more of the antibodies as defined in the foregoing aspects of the invention, or to fragments thereof, wherein said antibodies are bound to each other by a connecting structure.

In various further aspects, the present invention extends to binding members or antigen binding fragments derived from the fully humanised antibodies of the foregoing aspects of the invention. Such antigen binding fragments refer to one or more fragments of an antibody that retain the ability to specifically bind to an antigen, typically Toll-like Receptor 2. It has been shown that the antigen binding function of an antibody can be performed by fragments of a full length antibody. In certain embodiments, the binding members or antigen binding fragments may be isolated binding members. A binding member or antigen binding fragment of the invention may comprise a fragment of the antibodies of the present invention, e.g. a fragment of a fully humanised antibody molecule, such as the heavy or light chain only, or, for example, the variable domain of the heavy and/or light chain. In certain embodiments, a binding member may typically comprise, consist, or consist essentially of an antibody VH and/or VL domain. VH domains of binding members are also provided as part of the invention. Within each of the VH and VL domains are 3 complementarity determining regions ("CDRs"), along with 4 associated framework regions ("FRs"). A VH domain typically comprises 3 HCDRs (heavy chain complementarity determining regions), and a VL domain typically comprises 3 LCDRs (light chain complementarity regions). Accordingly, a binding member may comprise a VH domain comprising, in sequence, VH CDR1 (or HCDR1), CDR2 (HCDR2) and CDR3 (HCDR3) regions along with a plurality of associated framework regions. A binding member may additionally or alternatively comprise a VL domain comprising VL CDR1, CDR2 and CDR3 domains along with associated framework regions. The VH or VL domains typically comprise four framework regions, FR1, FR2, FR3 and FR4, interspersed between the 3 complementarity determining regions in the following arrangement: FR1-CDR1-FR2-CDR2-FR3-CDR3-FR4.

The variable region of the light chain (VL) comprises 3 complementarity determining regions (CDRs) which have a role in conferring the binding specificity of the antibody, or binding fragment. The complementarity determining regions may also be known as hypervariable regions. The 3 complementarity determining regions are shown below as SEQ ID NO:7, SEQ ID NO:8, and SEQ ID NO:9, these relating to the VLCDR1, VLCDR2 and VLCDR3.

```
VLCDR1:
                    (RASESVEYYGTSLMQ (SEQ ID NO: 7))
Arg-Ala-Ser-Glu-Ser-Val-Glu-Tyr-Tyr-Gly-Thr-

Ser-Leu-Met-Gln

VLCDR2:
                           (GASNVES (SEQ ID NO: 8))
Gly-Ala-Ser-Asn-Val-Glu-Ser

VLCDR3:
                         (QQSRKLPWT (SEQ ID NO: 9))
Gln-Gln-Ser-Arg-Lys-Leu-Pro-Trp-Thr
```

FIG. 1A shows the amino acid sequence of the VL domain of an antibody of the present invention as depicted in SEQ ID NO:1. FIG. 1B shows the variable light chain nucleotide sequence and the deduced amino acid sequence. The location of the VLCDR1, VLCDR2, and VLCDR3 regions is shown by the underlining of the appropriate amino acid residues which comprise each complementarity determining region (CDR) region in FIG. 1A.

In FIG. 1B, the residues of the light chain variable domain are conventionally numbered according to the numbering system devised by Kabat et al. (Kabat, E. A., Wu, T. T., Perry, H., Gottesman, K. and Foeller, C. (1991) Sequences of Proteins of Immunological Interest, Fifth Edition. NIH Publication No. 91-3242). The Kabat numbering system is generally used when referring to a residue in the variable domain (approximately residues 1-107 of the light chain and residues 1-113 of the heavy chain). This numbering system is used in the present specification except where otherwise stated. The Kabat residue designations do not always correspond directly with the linear numbering of the amino acid residues of the heavy and light chain variable regions of the present invention. The actual linear amino acid sequence may contain fewer or additional amino acids than in the strict Kabat numbering corresponding to a shortening of, or insertion into, a structural component, whether a framework region or complementarity determining region (CDR), of the basic variable domain structure of the heavy or light chain. The correct Kabat numbering of residues may be determined for any given antibody by alignment of residues in the sequence of the antibody with a standard sequence to which the Kabat numbering has been applied.

VLCDR1 (also known as VL-CRD1, light chain variable domain complementarity determining region 1, or CDR-L1) consists of 15 amino acid residues present at residues 24 to 38 of the light chain variable domain sequence as shown in FIG. 1A. These residues are shown as residues 24 to 34 in FIG. 1B, where due account is taken of resides 27, 27a, 27b, 27c and 27d. Hence, in the case of VLCDR1, 15 residues are taken to equate to CDRL1 region defined according to Kabat.

VLCDR2 (also known as VL-CRD2, light chain variable domain complementarity determining region 2, or CDR-L2) as shown in FIG. 1A consists of 7 amino acid residues and is positioned from residues 50 to 56 of the variable domain sequence as shown in FIG. 1B. These residues correlate exactly with residues 50 to 56 as taken to equate to CDRL2 region defined according to Kabat.

VLCDR3 (also known as VL-CRD3, light chain variable domain complementarity determining region 3, or CDR-L3) as shown in FIG. 1A consists of 9 amino acid residues and is positioned from residues 89 to 97 if the light chain variable domain sequence as shown in FIG. 1B. These residues correlate exactly with residues 89 to 97 as taken to equate to CDRL3 region defined according to Kabat.

The variable region of the heavy chain (VH) also comprises 3 complementarity determining regions (CDRs) which have a role in conferring the binding specificity of the antibody or antibody fragment. The 3 complementarity determining regions are shown below as SEQ ID NO:10, SEQ ID NO:11, and SEQ ID NO:12, these relating to the VHCDR1, VHCDR2 and VHCDR3.

```
VHCDR1:
                              (TYGIN (SEQ ID NO: 10))
Thr-Tyr-Gly-Ile-Asn.

VHCDR2:
                 (WIYPRDGSTNFNENFKD (SEQ ID NO: 11))
Trp-Ile-Tyr-Pro-Arg-Asp-Gly-Ser-Thr-Asn-Phe-

Asn-Glu-Asn-Phe-Leu-Asp.

VHCDR3:
                          (LTGGTFLDY (SEQ ID NO: 12))
Leu-Thr-Gly-Gly-Thr-Phe-Leu-Asp-Tyr.
```

FIG. 2A shows the amino acid sequence of the VH domain as depicted in SEQ ID NO:2. FIG. 2B shows the variable heavy chain nucleotide sequence and the deduced amino acid sequence.

In FIG. 2B, the residues of the heavy chain variable domain are conventionally numbered according to a system devised by Kabat (supra). The location of the VHCDR1, VHCDR2, and VHCDR3 regions are shown by the underlining of the appropriate amino acid residues in FIG. 2A.

VHCDR1 (also known as VH-CRD1, heavy chain variable domain complementarity determining region 1, or CDR-H1) consists of 5 amino acid residues present at residues 31 to 35 of the variable domain sequence. These residues correlate exactly with residues 31 to 35 as taken to equate to CDRH1 region defined according to Kabat.

VHCDR2 (also known as VH-CRD2, heavy chain variable domain complementarity determining region 2, or CDRH2) consists of 17 amino acid residues and is positioned from residues 50 to 65 of the variable domain sequence. These residues correlate exactly with residues 50 to 65 as taken to equate to CDRH2 region defined according to Kabat.

VHCDR3 (also known as VH-CRD3, heavy chain variable domain complementarity determining region 3, or CDRH3) consists of 9 amino acid residues and is positioned from residues 95 to 103 if the light chain variable domain sequence. Due to the presence of 2 residues at position 100 and 100a, which are considered to align with residue 100 of the CDRH3 region of the Kabat derived CDRH3 region, as illustrated in FIG. 2B, these 9 residues correlate exactly with the 8 residues (residues 95 to 102) of the CDHR2 region defined according to Kabat.

The CDRs of the light chain associate with the CDRs of the heavy chain to confer the binding specificity of an antibody, or antibody binding fragment, in instances where both sets of CDRs are present. It is known that the contribution made by the light chain variable region to the energetics of binding is small relative to the associated heavy chain variable region. Accordingly, isolated heavy chain regions, which comprise, in sequence, the 3 complementarity determining regions (VHCDR1, VHCDR2, and VHCDR3), are known to have an antigen binding capability and are commonly referred to as single domain antibodies. Such antibody fragments are provided by the present invention, based on the provision of the heavy chain variable domain of the present invention, such as that defined in SEQ ID NO:1.

In various further aspects, the invention extends to a fully humanised antibody or related binding member which has binding specificity for Toll-like Receptor 2 (TLR2, TLR-2, CD282) and which comprises, consists or consists essentially of at least one amino acid sequence selected from the group comprising SEQ ID NO:7 to SEQ ID NO:12. In certain embodiments, the binding member comprises the amino acid sequences of SEQ ID NO:10, 11 and 12. In certain further embodiments, there is provided a binding member comprising, consisting or consisting essentially of, in sequence, the amino acid sequence of SEQ ID NO:10, SEQ ID NO:11 and SEQ ID NO:12. In certain embodiments, each of SEQ ID NO:10, SEQ ID NO:11 and SEQ ID NO:12 may be provided in sequence, with framework regions being interspersed there between.

In certain embodiments, the amino acid sequences of the VH or VL domains may comprise at least one back mutation, said back mutation being the replacement of an amino acid residue at a specific position of the sequence so as to improve the binding specificity of the humanised antibody or fragment thereof, to TLR2 and/or to enhance the therapeutic efficacy of the humanised antibody as a TLR2 antagonist. Typically such modification can be made to the framework residues within the light and heavy chain variable regions so as to decrease the immunogenicity of the antibody. In certain embodiments, further engineering techniques can be used to modify the antibodies of the present invention, for example by including modifications of the Fc region which can alter serum half life, complement fixation, Fc receptor binding and/or antigen dependent cellular cytotoxicity. Further, in certain embodiments, the antibodies or antibody fragments can be produced which have altered glycosylation patterns. In certain embodiments, an antibody of the invention is altered to increase or decrease the extent to which the antibody is glycosylated.

Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

In certain further embodiments, the antibodies can be PEGylated by reacting the antibody with a plyethylene glycol (PEG) derivative. In certain embodiments, the antibody is defucosylated and therefore lacks fucose residues.

In certain embodiments, modifications in the biological properties of an antibody may be accomplished by selecting substitutions that affect (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues may be divided into groups based on common side-chain properties: (1) hydrophobic: Norleucine, Met, Ala, Val, Leu, He; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Such substituted residues also may be introduced into the conservative substitution sites or, into the remaining (e.g., non-conserved) sites.

In certain further aspects, the present invention extends to the use of the VL domain of SEQ ID NO:1, and/or the VH domain of SEQ ID NO:4 in the formation of a humanised antibody or a fragment thereof, where said antibody or fragment has binding specificity for Toll-like Receptor 2 and wherein said antibody or fragment functions to antagonise Toll-like Receptor 2 functional activity.

In certain further embodiments, the present invention extends to a binding member which has binding specificity to Toll-like Receptor 2 and which functions as a TLR2 antagonist, said binding member comprising, consisting or consisting essentially of an amino acid sequence of SEQ ID NO:1 or SEQ ID NO:4 or to sequences which have an amino acid sequence homology of at least 80%, more preferably at least 90%, more preferably at least 95% and most preferably at least 98% thereto.

In certain further aspects, the invention extends to a fully humanised monoclonal antibody, designated OPN-305 which is characterised in the examples below. The light chains variable domain (VL) amino acid sequence of OPN-305 is shown in SEQ ID NO:1, while the heavy chain variable domain (VH) amino acid sequence of OPN-305 is shown in SEQ ID NO:4. Further, the heavy chain amino acid sequence of OPN-305 is shown in SEQ ID NO:5, while the light chain amino acid sequence of OPN-305 is shown in SEQ ID NO:2.

The antibody may be produced by recombinant means, such as cell culture, or alternatively the antibody may be an isolated antibody. In certain embodiments, further modifications may be made to the Fc portion of the heavy chain, and in particular to the CH2 and CH3 constant domains of the antibody. In such embodiments, the antibody will comprise a light chain having the amino acid sequence of SEQ ID NO:2 and the heavy chain variable domain comprising the amino acid sequence of SEQ ID NO:4. In certain embodiments, a binding fragment may be derived from the OPN-305 fully humanised antibody, such as a Fab fragment, a F'ab fragment or an sc-Fv.

In various further aspects, the present invention extends to an immunoconjugate comprising an antibody of this disclosure, or an antigen binding portion thereof linked to a partner molecule. In certain embodiments, such an antibody-partner molecule conjugate is conjugated by means of a chemical linker, such as a peptidyl linker, a hydrazine linker or a disulphide linker. In certain embodiments, the coupling partner is an effector molecule, label, drug, or carrier molecule. Suitable techniques for coupling the antibodies of the invention to both peptidyl and non-peptidyl coupling partners will be will known to persons skilled in the art. Examples of suitable labels included detectable labels, such as a radiolabel, or an enzymatic label, such as horse radish peroxidase, or chemical moieties, such as biotin. Alternatively, the label may be a functional label, for example, ricin, or pro-drugs which are capable of converting prodrugs into active drugs at the site of antibody binding.

In various further aspects, the invention extends to a bispecific molecule comprising an antibody or antigen binding portion thereof linked to a second functional moiety having a different binding specificity than said antibody or an antigen binding portion thereof.

In certain further aspects, the present invention extends to a monoclonal antibody, binding fragment derived from an antibody, a peptide, an oligonucleotide, a peptidomimetic or an organic compound which specifically binds to the same epitope present on the extracellular domain of Toll-like Receptor 2 as that bound by the monoclonal antibody OPN-305, wherein the monoclonal antibody is not the commercially available antibody designated T2.5. Typically the epitope which is specifically bound by the compound comprises the amino acid sequence of SEQ ID NO:13 and/or SEQ ID NO:14. Such compounds have the ability to cross-compete with the antibodies disclosed herein to bind to Toll-like Receptor 2 at the same epitope. Such compounds can be identified by means of cross-competition binding studies, which can be conducted against an antibody of the present invention, such as OPN-305.

In various further aspects, the present invention extends to the use of a fully humanised antibody, fully humanised monoclonal antibody or binding member derived therefrom according to the present invention in the prevention and/or treatment of a disease or condition which is mediated in totality or in part by Toll-like Receptor 2 activation and/or intracellular signalling.

In certain embodiments the TLR2-mediated disease or condition is an inflammatory condition.

In certain embodiments, the binding member may be selected from the group comprising, but not limited to; a Fab fragment, a Fab' fragment, a scFv (single chain variable fragment), a peptidomimetic, a diabody, or a related multivalent derivative.

Techniques used for the recombinant production of Fab, Fab' and F(ab')2 fragments are well known to the person skilled in the art and include those disclosed in International PCT Patent Publication WO 92/22324, Sawai et al., "Direct Production of the Fab Fragment Derived From the Sperm Immobilizing Antibody Using Polymerase Chain Reaction and CDNa Expression Vectors", 1995, AJRI 34:26-34, and Mullinax et al., "Expression of a Heterodimeric Fab Antibody Protein in One Cloning Step", 1992, BioTechniques 12(6): 864-869 and Better et al., "*Escherichia coli* Secretion of an Active Chimeric Antibody Fragment" 1988, Science 240: 1041-1043, the contents of which are hereby incorporated by reference.

Examples of techniques which can be used to produce scFv (single chain Fv fragments) are disclosed in Huston et al., "Protein Engineering of Single-Chain Fv Analogs and Fusion Proteins", *Methods in Enzymology*, vol. 203:46-88 (1991), the contents of which are incorporated by reference.

In certain embodiments, antibody fragments can be derived from full length antibodies by proteolytic digestion according to the method of Morimoto (Morimoto et al., "Single-step purification of F(ab').sub.2 fragments of mouse monoclonal antibodies (immunoglobulins G1) by hydrophobic interaction high performance liquid chromatography using TSKgel Phenyl-5PW" Journal of Biochemical and Biophysical Methods 24:107-117 (1992)). Antibody fragments can also now be produced directly by host cells (see Carter et al., "High level *Escherichia coli* expression and production of a bivalent humanized antibody fragment" Bio/Technology 10:163-167 (1992)).

In various further aspects, the present invention provides a method for the treatment and/or prevention of an inflammatory condition which is mediated in totality or in part by Toll-like Receptor 2, said method comprising the steps of:
  providing a therapeutically effective amount of a humanised antibody or binding fragment thereof in accordance with the present invention, and
  administering the same to a subject in need of such treatment.

In certain embodiments, the method involves the administration of a multivalent monospecific antigen-binding protein comprising two three, four or more antibodies according to the invention.

A yet further aspect of the present invention provides a pharmaceutical composition comprising a humanised antibody, a humanised monoclonal antibody, an antigen binding portion thereof, immunoconjugate or bispecific molecule according to the present invention along with at least one pharmaceutically acceptable carrier, diluent or excipient.

In certain embodiments the formulation is a liquid formulation, a lyophilized formulation, a lyophilized formulation that is reconstituted as a liquid, or an aerosol formulation. In certain embodiments, the antibody in the formulation is at a concentration of: about 0.5 mg/ml to about 250 mg/ml, about 0.5 mg/ml to about 45 mg/ml, about 0.5 mg/ml to about 100 mg/ml, about 100 mg/ml to about 200 mg/ml, or about 50 mg/ml to about 250 mg/ml.

In certain embodiments, the formulation further comprises a buffer. Typically the pH of the formulation is from about pH 5.5 to about pH 6.5.

In certain embodiments, the buffer may comprise from about 4 mM to about 60 mM histidine buffer, about 5 mM to about 25 mM succinate buffer, or about 5 mM to 25 mM acetate buffer. In certain embodiments, the buffer comprises sodium chloride at a concentration of from about 10 mM to 300 mM, typically at around 125 mM concentration and sodium citrate at a concentration of from about 5 mM to 50 mM, typically 25 mM. In certain embodiments the formulation can further comprise a surfactant at a concentration of about 0% to about 0.2%. In certain embodiments the surfactant is selected from the group consisting of, but not limited to: polysorbate-20, polysorbate-40, polysorbate-60, polysorbate-65, polysorbate-80, polysorbate-85, and combinations thereof. In a preferred embodiment, the surfactant is polysorbate-20. In certain embodiments, the formulation further comprises about 0.001% to about 0.05% Tween and may further comprise sodium chloride at a concentration of about 125 mM and sodium citrate at a concentration of about 25 mM.

In certain embodiments, the pharmaceutical composition may further comprise, or be administered to a subject along with at least one immunomodulatory compound, such as an immune suppressant compound, a secondary antibody or fragment thereof, or a recombinant protein.

The antibody and binding members of the present invention may also be used in diagnosis, for example in the in vivo diagnosis and imaging of disease states involving Toll-like Receptor 2, where the antibody of the invention can be used to target and bind to cells expressing Toll-like Receptor 2. Furthermore, in certain embodiments, a secondary molecule or compound may be conjoined to the antibody of the invention for use in targeting that secondary molecule or compound to cells which express Toll-like Receptor 2.

In certain further aspects, the present invention provides a kit for the treatment or prevent of a Toll-like Receptor 2 mediated inflammatory conditions or disease. In certain embodiments, the kits comprise an antibody according to the present invention or an antigen binding fragment thereof that is capable of binding to Toll-like Receptor 2 and antagonising its functional activity, and instructions for the administration of the same to a patient.

According to a yet further aspect there is provided a humanised neutralising antibody or an antigen binding portion thereof, wherein the antibody specifically binds to mammalian Toll-like Receptor 2 with a $K_D$ of $1 \times 10^{-8}$ or less, but does not bind to CD32 (Fc gamma receptor II), wherein the antibody specifically binds to the same epitope present on the extracellular domain of Toll-like Receptor 2 as that bound by the commercially available antibody designated T2.5.

According to a yet further aspect there is provided an isolated monoclonal antibody, or antigen binding portion thereof, which binds an epitope on mammalian Toll-like Receptor 2 with a $K_D$ of $1 \times 10^{-8}$ or less and which does not bind to CD32 (Fc gamma receptor II), wherein the epitope is recognised by a reference antibody, wherein the reference antibody comprises a heavy chain variable region comprising the amino acid sequence of SEQ ID NO:4 and a light chain variable region comprising the amino acid sequence of SEQ ID NO:1.

According to a yet further aspect there is provided an isolated human monoclonal antibody, or an antigen binding portion thereof, which specifically binds mammalian Toll-like Receptor 2 and exhibits the following properties:
  binds to mammalian Toll-like Receptor 2 with a $K_D$ of $1 \times 10^{-8}$ or less,
  does not bind to CD32 (Fc gamma receptor II)
  is cross-reactive to human Toll-like Receptor 2, murine Toll-like Receptor 2 and monkey Toll-like Receptor 2.

Fab Binding Members

In certain embodiments of the foregoing aspects of the invention, an antibody fragment or an antigen binding portion of an antibody is provided by the invention. Examples of binding fragments include a Fab, F'ab, or F(ab')2 fragment, which is a monovalent fragment consisting of, or consisting essentially of, the VL, VH, CL and CH1 domains of a heterotetrameric antibody. In certain embodiments, the VL domain has an amino acid sequence of SEQ ID NO:1, and the VH domain has an amino acid sequence of SEQ ID NO:4. In certain embodiments, the CL and CH1 domains are based on the amino acid sequence of a CL and CH1 domain of an immunoglobulin of the subclass IgG and isotype IgG4, or of CL and CH1 domains as shown in SEQ ID NO:5 of FIG. 5. In certain embodiments, the Fab fragment of this embodiment of the invention can be used for the treatment or prophylaxis of conditions including, but not limited to psoriasis, dermatitis, and ocular disease including uveitis and AMD (age-related macular degeneration).

Single Domain Binding Members

In addition to providing a humanised monoclonal antibody which has binding specificity to TLR2 and which antagonises TLR2 function, the present invention further extends to binding members other than antibodies comprising a pair of binding domains based on the amino acid sequence of a VL (light chain variable) region as defined in SEQ ID NO:1 and an amino acid sequence of a VH (heavy chain variable) region as defined in SEQ ID NO:4. In particular, the invention extends to single binding domains which are based on either the VL or VH region of the humanised antibodies of the antibodies of the invention.

Accordingly, in certain further embodiments of the present invention, there is provided a binding member comprising, consisting or consisting essentially of a single binding domain derived from the humanised antibody of the invention. In certain embodiments, the single binding domain is derived from the amino acid sequence of the VH (heavy chain variable domain) as defined in SEQ ID NO:4. Such a binding domain may be used as a targeting agent to TLR2, as it is known that immunoglobulin VH domains are capable of binding to target antigens in a specific manner.

Modification of CDR Residues

It will be appreciated by those skilled in the art that the sequences of the complementarity regions (as defined in SEQ ID NO:7, 8, 9, 10, 11 and 12), as well as sequences of the hypervariable and variable regions can be modified without losing the ability to bind specifically to TLR2. For example, CDR regions of binding members derived from the humanised antibodies of the present invention can be either identical or highly homologous (e.g. 95% sequence identity or higher) to the amino acid sequences defined herein in SEQ ID NO: 7, 8, 9, 10, 11 and 12. As herein defined, by the term "highly homologous" it is meant that from 1 to 5 amino acid substitutions may be made to the sequences of the CDRs. In certain embodiments, the degree of homology which exists between respective CDRs, hypervariable regions or variable regions and their non-modified counterparts will be at least 80%, preferably 90%, more preferably at least 95% and most preferably greater than 98%. Such modified sequences fall within the scope of the present invention in instances where the modified or homologous binding member retains the ability to specifically bind to TLR2 and antagonise its functional activity.

Polynucleotides

In various further aspects, the present invention extends to polynucleotides, and in particular isolated polynucleotides, which encode the humanised antibodies, antibody fragments and binding members of the present invention.

Accordingly in a further aspect of the present invention there is provided a polynucleotide which encodes the amino acid sequence of SEQ ID NO:1 and/or SEQ ID NO:4. In certain embodiments, the polynucleotide is an isolated polynucleotide.

As defined herein, a "polynucleotide" includes any polyribonucleotide or polydeoxyribonucleotide, which may be unmodified RNA or DNA, or modified RNA or DNA, including without limitation, single and double stranded RNA, and RNA which is a mixture of single and double stranded regions.

A polynucleotide of the invention, e.g. a polynucleotide which encodes a polypeptide or polypeptides comprising the amino acid sequence of SEQ ID NO:1 or SEQ ID NO:4, includes allelic variants thereof and/or their complements including a polynucleotide that hybridises to such nucleotide sequences under conditions of moderate or high stringency.

In various further aspects, the invention extends to an expression vector comprising a polynucleotide which encodes a polypeptide comprising SEQ ID NO:1 and/or SEQ ID NO:4. Furthermore, the invention extends to a host cell transformed with such a vector.

Hybridoma Cell Lines

A yet further aspect of the present invention provides a hybrid cell line (hybridoma), which expresses an antibody having a heavy chain variable domain amino acid sequence of SEQ ID NO:1 and a light chain variable amino acid sequence of SEQ ID NO:4.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A shows SEQ ID NO:1 which is the amino acid sequence of the variable domain of a light chain of an antibody according to the invention, FIG. 1B shows the variable light chain nucleotide sequence (SEQ ID NO:17) and the deduced amino acid sequence (SEQ ID NO:18) which has been numbered according to Kabat, FIG. 2A shows SEQ ID NO:4 which is the amino acid sequence of the variable domain of a heavy chain of an antibody according to the invention. FIG. 2B shows the variable heavy chain nucleotide sequence (SEQ ID NO:19) and the deduced amino acid sequence (SEQ ID NO:20) which has been numbered according to Kabat, FIG. 3 shows SEQ ID NO:2 which depicts the amino acid sequence of the light chain of an antibody according to the invention, FIG. 4 shows SEQ ID NO:3 which shows a nucleic acid sequence which can be translated to encode the amino acid sequence of SEQ ID NO:2, FIG. 5 shows SEQ ID NO:5 which is the amino acid sequence of the heavy chain of an antibody according to the invention, FIG. 6 shows SEQ ID NO:6 which is a nucleic acid sequence which can be translated to encode the amino acid sequence of SEQ ID NO:5, FIG. 7 shows SEQ ID NO:15 which provides the amino acid sequence of human Toll-like Receptor 2, FIG. 8 shows SEQ ID NO:16 which provides the amino acid sequence of murine Toll-like Receptor 2, FIG. 10 shows that Toll-like Receptor 2 antagonism mediated by the OPN301 monoclonal antibody is dependent upon the antibody binding to CD32 (FIG. 10A), whereas OPN-305 mediated Toll-like Receptor 2 antagonism is not dependent upon the antibody binding to CD32 (FIG. 10B).

Column B relates to cells exposed to the OPN-301 antibody. Column C relates to OPN301 antibody along with 0.4 µg/ml anti-CD32a/b or a control goat IgG antibody. Column D relates to OPN301 antibody along with 2 µg/ml anti-CD32a/b antibody or a control goat IgG antibody. Column E relates to OPN301 antibody, plus 10 µg/ml anti-CD32a/b antibody or a control goat IgG antibody.

FIG. 14 shows 2 FACS analysis traces that show that OPN-305 competes with the anti-TLR2 murine monoclonal antibody OPN-301 for binding to monkey TLR2, wherein

FIG. 19 shows an alignment of the light chain variable region amino acid sequence of the OPN-305 anti-TLR2 monoclonal antibody (SEQ ID NO:22) and the T2.5 murine anti-TLR2 monoclonal antibody (SEQ ID NO:21), wherein the determined sequence identity is shown to be 89.2%.

FIG. 20 shows an alignment of the heavy chain variable region amino acid sequence of the OPN-305 anti-TLR2 monoclonal antibody (SEQ ID NO:24) and the T2.5 murine anti-TLR2 monoclonal antibody (SEQ ID NO:23), wherein the determined sequence identity is shown to be 88.1%.

FIG. 22A depicts NF-kB dependent SEAP activity versus [Pam3CSK4], while FIG. 22B depicts a Lineweaver Burk Plot of 1/V versus 1/S.

DETAILED DESCRIPTION OF THE INVENTION

Figure 9:
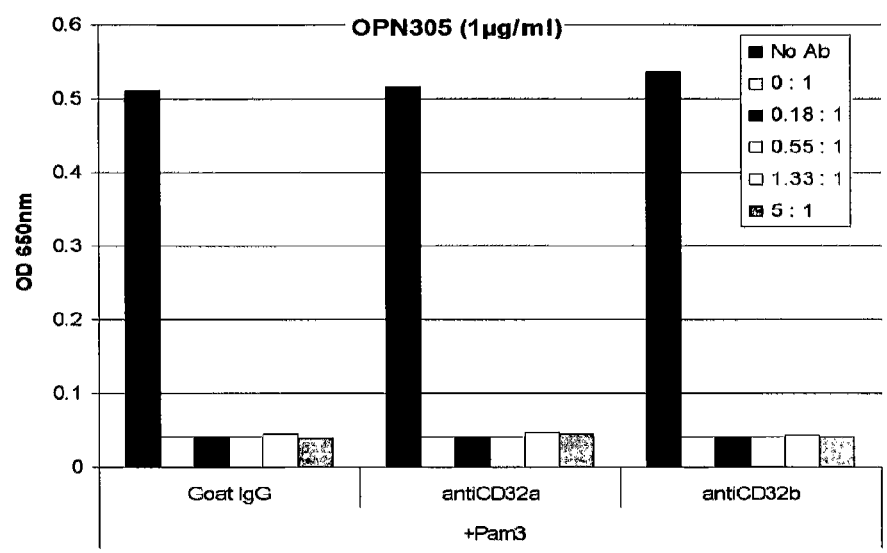
FIG. 9 shows that OPN-305 mediated Toll-like Receptor 2 antagonism is not dependent on the antibody binding to CD32, with group 1 showing the addition of a control goat antibody, group 2 showing the addition of a goat anti-hCD32a blocking antibody, and group 3 showing the addition of a goat anti-hCD32b blocking antibody.

The present invention provides a fully human monoclonal antibody which has binding specificity for Toll-like Receptor 2 and which, when bound to Toll-like Receptor 2, antagonises Toll-like Receptor 2 functional activity. The invention further provides binding fragments derived from the fully human antibody and further to binding members which comprise, consist or consist essentially of the variable light chain domain amino acid sequence of SEQ ID NO:1 and/or the variable heavy chain domain amino acid sequence of SEQ ID NO:4.

By the term "antagonising Toll-like Receptor 2 function", or similar terms, such as "Toll-like Receptor 2 antagonist" or "agonist of Toll-like Receptor 2" it is meant that the antibody, fragment or binding member binds specifically to Toll-like Receptor 2 and inhibits or blocks the binding of a ligand or binding compound to Toll-like Receptor 2, which would in turn cause activation of Toll-like Receptor 2, e.g. a Toll-like Receptor 2 ligand. The antibody, fragment or binding member may further inhibit Toll-like Receptor 2 activation and function by inhibiting or suppressing intracellular signalling mediated by Toll-like Receptor 2 following the binding of a Toll-like Receptor 2 ligand. By "Toll-like Receptor 2 activation and downstream mediated signaling" it is meant any intracellular signaling pathway which is induced by activation of TLR2. The signaling pathway may be a TLR2 specific pathway, or may be a "shared" signalling pathway, for example where the signalling pathway may be activated by other sources, for example, by means of the activation of receptors other than TLR2 which contribute to the activation of mediators of the immune response such as the transcription factor NF-kappaB.

TLR2 is known to dimerise into 2 functional heterodimers. In particular, TLR2 is known to form a heterodimer with either Toll-like Receptor 1 or Toll-like Receptor 6. It is possible that further heterodimers are formed with Toll-like Receptor 4 (TLR4, TLR-4) and Toll-like Receptor 10 (TLR10, TLR-10). It is thought that this dimerisation is associated with a discrimination that results in the binding of TLR2 by different microbial-derived ligands. The inventor has identified that the humanised antibodies of the invention function to antagonise TLR2 function irrespective of whether Toll-like Receptor 2 forms a heterodimer with Toll-like Receptor 1 or Toll-like Receptor 6.

Antibody Binding Epitope

The humanised antibodies of the invention, or the fragments thereof, or binding members based thereon selectively bind to Toll-like Receptor 2 and antagonise its function. Monoclonal antibodies can block the activation of a receptor by its ligand by binding near to the ligand binding site of the receptor, this resulting in steric hindrance which precludes access of the ligand to the ligand binding site.

Without wishing to be bound by theory, the inventor has identified the binding site which is bound by the humanised antibodies according to the present invention. The antibody binds to an epitope which comprises residues derived from both the N-terminal and C-terminal domains of the mature extracellular domain of Toll-like receptor 2 (TLR2). In certain embodiments, the epitope comprises amino acid residues 19 to 39 of the N-terminal of Toll-like Receptor 2 as determined from the 586 amino acid sequence of Toll-like Receptor 2, said amino acids being KEESSNQASLSCDRN-GICKGS (SEQ ID NO:13). The binding epitope further comprises amino acids residues 538 to 549 of Toll-like Receptor 2 as present at the C-terminal region of the amino acid sequence of SEQ ID NO:1, this sequence comprising the amino acids CSCEFLSFTQEQQ (SEQ ID NO:14).

Cross-Reactivity

Typically, the TLR2 which is antagonized by the antibodies, antibody fragments or binding members of the invention is a mammalian TLR2 (or a functional variant thereof), e.g., human TLR2 or murine TLR2. In certain embodiments, the TLR2 antagonized is the human form of TLR2 having the amino acid sequence as defined in FIG. 7 as SEQ ID NO:15, this comprising the 784 amino acid full length human Toll-like Receptor sequence as defined as Genbank Accession Number AAC 34133 (URL www.ncbi.nlm.nih.gov).

In certain further embodiments, the Toll-like Receptor 2 is murine TLR2, this comprising the amino acid sequence defined FIG. 8 as SEQ ID NO:16, as derived from Genbank Accession Number NP_036035 (*Mus musculus*).

In certain further embodiments, the antibodies, antibody fragments or binding members of the invention serve to antagonise the functional activity or signalling of Toll-like Receptor 2 expressed on monkey cells.

In certain further embodiments, the antibody may have a dissociation constant (Kd) selected from the group consisting of: (i) a dissociation constant between $10^{-7}$M and $10^{-11}$M, (ii) a dissociation constant of between $10^{-8}$M and $10^{-9}$M, (iii) a dissociation constant of between $10^{-9}$M and $10^{-19}$M, (iv) a dissociation constant of between $10^{-11}$M and $10^{-12}$M. In certain embodiments, the antibodies of the invention, or fragments thereof may bind to human or murine Toll-like Receptor 2 with a Kd of $3\times10^{-8}$ or less, or $4\times10^{-8}$ or less.

Binding of an antibody of the invention to Toll-like Receptor 2 can therefore result in the blocking of intracellular signalling which is associated with the ligand/receptor interaction of TLR2 and its ligand.

Antibody Structure

The antibody and antibody fragments of the invention are fully human. That is, the amino acid residues which comprise the antibody are derived from the human species as opposed to, for example, a mouse. The antibody of the invention is therefore less immunogenic than a murine antibody or a chimeric antibody, such as a mouse/human antibody.

The immunogenicity which results from the administration of a murine or chimeric antibody has proved to be the most significant barrier to the therapeutic use of monoclonal antibodies. Accordingly, the provision of a fully human antibody overcomes the problems associated with the provision of murine, or human/mouse chimeric antibodies, which, when administered to a subject more than once, can result in an immunogenic reaction, such as a HAMA response, being directed against the antibody. This response clears the murine or chimeric antibody from the subject's serum, thereby preventing the antibodies reaching their target and producing their intended therapeutic effect. Accordingly, the fully human antibody of the present invention confers a significant advantage over such murine and chimeric antibodies.

One intrinsic cause of immunogenicity against an antibody are CD4+ T cells epitopes present on the antibody. Accordingly, the antibody and binding fragments of the present invention have been analysed to identify and modify any CD4+ T cell epitopes present on the antibody or antibody fragment. This process further reduces the immunogenicity of the antibody and antibody fragments of the invention.

Moreover, the antibody or antibody fragments of the invention may be subject to one or more techniques which may further be used to ensure that an immunogenic response is not mounted against the antibody when administered to a subject.

Examples of such techniques will be well known to the person skilled in the art and include, but are not limited to, de-immunisation, gene shuffling and PEGylation.

Furthermore, in order to enhance the biologic function or therapeutic activity of an antibody or antibody fragment of the invention, further optimisation techniques may be employed. Such techniques include, but are not limited to modifying the following attributes of the antibody: potency, affinity, binding specificity, K on (association rate constant), K off (dissociation rate constant), thermodynamic stability, solubility, serum half-life, expression, folding kinetics, protease susceptibility, Fc region effector function and drug recycling. The biological function or therapeutic activity which may be modulated includes, but is not limited to: enhancement of efficacy, improved pharmacokinetic profile, enhanced patient convenience, decreased cost of goods, improved safety profile, reduced immunogenicity and extended shelf-life.

Treatment of TLR2-Mediated Disease

The humanised antibodies, antibody fragments and binding members of the invention may induce immunosuppression (suppression of an immune response, most particularly a pro-inflammatory immune response), in particular by suppressing Toll-like Receptor 2 mediated activation and signalling. This suppression of Toll-like Receptor 2 function has been identified by the inventor as having utility in the treatment or prevention of disease conditions in which Toll-like Receptor 2 activation and signalling contributes to the onset or progression of disease.

An antibody of the invention may be used in, for example, in vitro, ex vivo, and in vivo therapeutic methods.

In certain further aspects, the invention extends to the use of the antibodies, antibody fragments or binding members of the invention for the treatment of disease conditions mediated by Toll-like Receptor 2 activation and signalling.

Treatment of Ischemia

Accordingly, in a further aspect, the present invention provides a method for the treatment and/or prophylaxis of ischemia reperfusion injury or a condition caused thereby or associated therewith, the method comprising the steps of:

providing a therapeutically effective amount of a humanised antibody, or binding fragment thereof as defined herein, and administering said compound to a subject in need of such treatment.

A yet further aspect of the invention provides a fully humanised antibody according to the present invention, or a binding member derived therefrom for use in treating ischemia reperfusion injury or a cardiac inflammatory condition which is mediated in totality or in part by Toll-like Receptor 2 activation by a Toll-like Receptor 2 ligand.

A yet further aspect provides the use of a humanised antibody according to the present invention, or a fragment thereof or a binding member derived therefrom in the preparation of a medicament for the treatment or prevention of ischemia reperfusion injury or a cardiac inflammatory condition which is mediated in totality or in part by Toll-like Receptor 2 activation by a Toll-like Receptor 2 ligand.

In certain embodiments, the cardiac inflammatory condition results from the occurrence of reperfusion injury and can be selected from the group comprising, but not limited to: myocardial ischemia, ischemic heart disease, hypertension myocardial ischemia, congestive heart failure, tissue ischemia, organ ischemia, acute coronary syndrome, hypertrophy, cerebral infarction, myocardial infarction, arrhythmia, ischemia reperfusion injury (I/R injury).

Ischemia is caused when an organ or part of the body fails to receive a sufficient blood supply. An organ that is deprived of an adequate blood supply is said to be hypoxic. Reperfusion occurs when blood flow recommences to an organ following temporary deprivation. Reperfusion injury relates to damage which occurs to a tissue or an organ upon the return of the blood supply to a tissue following a period of ischemia. The absence of oxygen and nutrients during the period of ischemia results in a period of inflammation and oxidative damage when circulation returns. Examples of ischemia reperfusion injury include hypoxia, stroke, heart attack, chronic kidney failure or organ transplantation.

In certain embodiments, the methods of this aspect of the invention may be used for the treatment or prevention of ischemia reperfusion injury which may result from organ transplantation in a subject. In certain embodiments, the antibody of the invention can be used for the treatment and/or prevention of ischemia which may result from solid organ transplantation.

A yet further aspect of the present invention provides a method of reducing one or more biological activities of Toll-like receptor 2 (TLR2) in a TLR2 expressing cell or tissue implicated in ischemia reperfusion injury associated with solid organ transplantation in a subject, comprising:

contacting the cell or tissue with a Toll-like Receptor 2 antagonistic antibody according to the present invention, in an amount sufficient to reduce one or more biological activities of TLR2 in the cell or tissue.

In certain embodiments the TLR2 expressing cell or tissue is a cell or tissue of the myocardium. In certain embodiments the TLR2 expressing cell or tissue is a cell or tissue involved with a reperfusion induced cardiac inflammatory condition selected from the group comprising, but not limited to: myocardial ischemia, ischemic heart disease, hypertension myocardial ischemia, congestive heart failure, tissue ischemia, organ ischemia, acute coronary syndrome, hypertrophy, cerebral infarction, myocardial infarction, arrhythmia, ischemia reperfusion injury (I/R injury).

In certain embodiments the method is performed on a human subject having, or at risk of having ischemia reperfusion injury.

A yet further aspect of the present invention extends to the use of an antibody according to the present invention, or a binding fragment thereof, for use in treating or preventing ischemia and reperfusion associated with solid organ transplantation.

Treatment of Autoimmune Disease

In a yet further aspect, the present invention provides a method for the treatment and/or prophylaxis of an autoimmune disease or condition associated therewith, the method comprising the steps of:

providing a therapeutically effective amount of a humanised antibody, or binding fragment thereof as defined herein, and administering said compound to a subject in need of such treatment.

A yet further aspect of the invention provides a humanised antibody according to the present invention, or a binding member derived there from for use in treating an autoimmune disease which is mediated in totality or in part by Toll-like Receptor 2 activation by a Toll-like Receptor 2 ligand.

A yet further aspect provides the use of a humanised antibody according to the present invention, or a binding member derived there from in the preparation of a medicament for the treatment or prevention of an autoimmune disease which is mediated in totality or in part by Toll-like Receptor 2 activation by a Toll-like Receptor 2 ligand.

In certain embodiments, the autoimmune disease is autoimmune arthritis, in particular rheumatoid arthritis. In certain embodiments, the autoimmune disease is selected from the group comprising psoriasis, dermatitis. In certain further embodiments, the autoimmune disease is diabetes. Typically the diabetes is diabetes mellitus. In certain embodiments, the diabetes is Type 1 diabetes mellitus. In certain further embodiments, the diabetes is Type 2 diabetes mellitus.

In certain embodiments, the condition which results from the subject having diabetes may be termed a diabetic complication. Such diabetic complications may be acute complications, chronic complications or a combination of both.

Where the diabetic complication is an acute complication, the complication may be selected from the group comprising, but not limited to, retinopathy, neuropathy, peripheral circulation disorders, skin ulcerations, polyuria, polydipsia, polyphagia, diabetic ketoacidosis (DKA) and hyperosmolar non-ketotic state. In certain further embodiments the condition may be a condition which results from any one of the preceding acute or chronic conditions and may include, but is not limited to, blindness, proteinurea, pain, numbness, psychroesthesia, intermittent claudication and gangrene.

In certain further embodiments the diabetic complication may be a chronic complication such as vascular disease resulting from the chronic elevation of blood glucose levels leading to damage of the blood vessels (angiopathy). In such embodiments, where vascular damage occurs to small blood vessels, this can lead to micro-angiopathy, which can lead to one or more of diabetic retinopathy, diabetic neuropathy and diabetic nephropathy.

According to a still further aspect of the invention there is provided a method for treating or preventing an obesity associated disorder in a subject which is mediated in totality or in part by the activation of Toll-like Receptor 2 by a Toll-like Receptor 2 ligand, the method comprising administering to the subject a therapeutically effective amount of an antibody according to any of the foregoing aspects of the present invention, or a binding derived there from.

A yet further aspect of the invention provides a humanised antibody according to the present invention, or a binding member derived there from for use in treating and/or preventing obesity which is mediated in totality or in part by Toll-like Receptor 2 activation by a Toll-like Receptor 2 ligand.

A yet further aspect provides the use of a humanised antibody according to the present invention, or a binding member derived therefrom in the preparation of a medicament for the treatment or prevention of disease condition which is associated with obesity, where the condition is caused in totality or in part by Toll-like Receptor 2 activation by a Toll-like Receptor 2 ligand.

In certain embodiments the obesity associated disorder is at least one condition selected from the group comprising, but not limited to, diabetes, in particular Type 2 diabetes mellitus, insulin resistance, hyperinsulinemia, decreased glucose clearance, dyslipidemia, non-alcoholic fatty liver disease, hypertension, inflammation, hepatomegaly, hepatic steatosis, myocardial infarction, asthma or stroke.

A yet further aspect of the present invention provides a method for treating insulin resistance in a subject, the method comprising administering to the subject a therapeutically effective amount of an antibody according to the present invention, or a binding member provided by the present invention.

A yet further aspect of the invention provides a humanised antibody, fragment thereof or a binding member derived there from for use in treating insulin resistance in a subject which is mediated in totality or in part by Toll-like Receptor 2 activation by a Toll-like Receptor 2 ligand.

A yet further aspect provides the use of a humanised antibody according to the present invention, or a binding member derived there from in the preparation of a medicament for the treatment or prevention of insulin resistance in a subject which is mediated in totality or in part by Toll-like Receptor 2 activation by a Toll-like Receptor 2 ligand.

Treatment of Ocular Disease

In certain further aspects, the present invention extends to methods for the treatment and/or prophylaxis of ocular disease, wherein said methods comprise the steps of:
  providing a therapeutically effective amount of a humanised antibody, binding fragment or binding member provided by the present invention, and
  administering said compound to a subject in need of such treatment.

A yet further aspect of the present invention provides for the use of an antibody according to the present invention, or a binding member derived there from for treating or preventing ocular disease.

In certain embodiments, the ocular disease is uveitis or age-related macular degeneration (AMD).

Treatment of Renal Inflammation

A yet further aspect of the present invention provides a method for the treatment and/or prophylaxis of renal inflammation and disease or a condition caused thereby or associated therewith, the method comprising the steps of:
  providing a therapeutically effective amount of a humanised antibody, binding fragment or binding member provided by the present invention, and
  administering said compound to a subject in need of such treatment.

A yet further aspect of the invention provides a humanised antibody according to the present invention, or a binding member derived therefrom for use in treating renal inflammation or renal disease which is mediated in totality or in part by Toll-like Receptor 2 activation by a Toll-like Receptor 2 ligand.

A yet further aspect provides the use of a humanised antibody according to the present invention, or a binding member derived therefrom in the preparation of a medicament for the treatment or prevention of renal inflammation or renal disease which is mediated in totality or in part by Toll-like Receptor 2 activation by a Toll-like Receptor 2 ligand.

As herein defined, the terms "renal inflammation" and "renal disease" extend to conditions which are substantially characterised by the occurrence of inflammation within the kidney, or cells of the kidney, or where the occurrence of inflammation in the kidney is caused by a disease or an inflammatory condition which primarily affects a site in the body other than the kidney. In particular, inflammation may occur at a site including, but not limited to; the glomerulus, Bowman's capsule or Bowman's space. Typically, the inflammation results in at least partial impairment of kidney function and/or kidney failure.

In certain embodiments, the renal inflammation and disease includes "kidney disease", wherein the term kidney disease generally refers to a disorder of at least one kidney in a human, wherein the disorder compromises or impairs the function of the kidney(s), this being characterised physiologically by, for example, the leakage of protein into the urine, or by the excretion of nitrogenous waste. The Kidney disease may also result from a primary pathology of the kidney, such as injury to the glomerulus or tubule, or from damage to another organ, such as the pancreas, which adversely affects the ability of the kidney to perform biological functions, such as the retention of protein. Thus, Kidney disease in the human can be the direct or indirect effect of a disease condition which may affect other organs. Examples of diseases which affect the kidneys, but which do not specifically target the kidneys are diabetes and systemic lupus. The terms renal disease and kidney disease are used interchangeably herein with the phrase "diseases of the kidney". The kidney disease can, for example, result from, or be a consequence of any change, damage, or trauma to the glomerulus, tubules or interstitial tissue in either the kidney cortex or kidney medulla.

In certain embodiments, the kidney disease may also be a progressive kidney disease. The term "progressive kidney disease" as used herein refers to any disease of the kidney that over time (e.g., days, weeks, months, years) leads to a loss of kidney function. As herein defined, the term "kidney function" generally refers to a physiological property of the kidney, such as the ability to retain protein thereby preventing proteinuria (e.g. albuminuria). Kidney function can be assessed, for example, by glomerular filtration rate (e.g. creatinine clearance), excretion of protein in urine e.g. albuminuria, blood urea nitrogen, serum or plasma creatinine, or any combination thereof.

Examples of specific conditions which fall within the meaning of the term "renal inflammation and disease" include, but are not limited to: renal disorders which include, but are not limited to: chronic renal failure, acute renal failure, heterologous nephrotoxic nephritis, glomerulonephritis, sclerosis of the glomerulus, systemic lupus erythematosus (SLE), diabetic nephropathy, diabetic nephropathy wherein the diabetic nephropathy accompanies sclerosis of the liver, and glomerulonephritis wherein the glomerulonephritis is accompanied by sclerosis of the liver.

In certain further embodiments, renal inflammation and disease may relate to an immune-mediated disease which affects the cells of the kidney and/or kidney function. Such conditions may include, but are not limited to: Immunoglobulin A nephropathy, membranoproliferative glomerulonephritis, mesangial proliferative glomerulonephritis, nonproliferative glomerulonephritis, membranous glomerulonephritis, minimal-change disease, primary focal segmental glomerulosclerosis (FSGS), fibrillary glomerulonephritis, immunotactoid glomerulonephritis, proliferative glomerulonephritis, progressive glomerulonephritis, anti-GBM disease, kidney ischemia, kidney vasculitis, including disease associated with anti-neutrophil cytoplasmic antibodies (ANCA) (e.g., Wegener granulomatosis), lupus nephritis cryoglobulinemia-associated glomerulonephritis, bacterial endocarditis, Henoch-Schönlein purpura, postinfectious glomerulonephritis, Hepatitis C, diabetic nephropathy, myloidosis, hypertensive nephrosclerosis, light-chain disease from multiple myeloma, secondary focal glomerulosclerosis, and hypertensive nephrosclerosis.

The term "renal inflammation and disease" also encompasses acute renal failure. Acute renal failure ("ARF") refers to the clinical conditions associated with rapid, steadily increasing azotemia, with or without oliguria (<500 mL/day). The cause of ARF can be grouped into three diagnostic categories: prerenal (inadequate renal perfusion); postrenal (obstruction); and renal. The pathophysiology of ARF is complex and multifactorial. Current concepts suggest that ARF may result from direct renal tubular injury, renal ischemia or intra-tubular obstruction. Clinically, ARF results in diminished glomerular filtration and reduced secretion of metabolic waste products, water, and electrolytes. Fluid overload, electrolyte imbalances and the uremic syndrome result in organ dysfunction. Organ dysfunction may ultimately result in death.

In various further aspects, the present invention extends to methods of modulating a function (e.g., altering one or more biological activities of TLR2) in a TLR2-responsive cell and/or tissue (e.g., a tissue which has undergone ischemia, which may undergo ischemia, or which may undergo reperfusion, a beta cell of the islets of Langerhans of the pancreas, or any further cell type which expresses TLR2 and which is implicated in a TLR2 mediated disease condition, or the development thereof). The method includes contacting the TLR2-responsive cell and/or TLR2-responsive tissue with a humanised antibody or binding fragment thereof as provided by the invention in an amount sufficient to antagonise the function of the TLR2-responsive cell or tissue, or the biological activity of TLR2 in the cell or tissue. In one embodiment, the contacting step can be effected in vitro, for example in a cell lysate or in a reconstituted system. Alternatively, the subject method can be performed on cells in culture, e.g., in-vitro or ex-vivo. For example, cells, such as purified or recombinant cells, can be cultured in-vitro and the contacting step can be effected by adding the TLR2 modulator to the culture medium. Typically, the TLR2-responsive cell is a mammalian cell, such as a human cell. In some embodiments, the TLR2-responsive tissue is a tissue which has undergone ischemia and which may undergo reperfusion, or is a cellular population associated therewith. In other embodiments, the method can be performed on cells present in a subject, e.g., as part of an in-vivo protocol, or in an animal subject (including, e.g., a human subject, or an in-vivo animal model). The in-vivo protocol can be therapeutic or prophylactic, and the inflammatory model can be, for example, a genetically modified model, such as an animal model having over expressed TLR2, or a mutation or deletion in a TLR receptor. For in vivo methods, the humanised antibody or fragment thereof can be provided alone or in combination with another agent, such as a secondary therapeutic, such as an anti-inflammatory drug, or a pharmaceutically acceptable carrier, excipient or diluent. Typically the antibody is administered to a subject suffering, or at risk of suffering from the TLR2-mediated condition, such as rheumatoid arthritis, ischemia reperfusion injury, diabetes or renal inflammation, in an amount sufficient to antagonise one or more TLR2 mediated activities or functions in the subject. In certain embodiments, the amount or dosage of the humanised anti-TLR2 antibody of the invention that is administered can be determined prior to administration by testing in-vitro or ex-vivo, the amount of antibody required to alter, e.g., decrease or inhibit, one or more functional activity of TLR2, said functional activity typically being one or more TLR2 biological activities described herein.

It is understood that any of the above therapeutic methods may be carried out using an immunoconjugate of the invention in place of or in addition to the anti-TLR2 antibodies, or antibody binding fragment of the invention.

In certain further aspects, the invention extends to the use of the antibodies of the present invention in diagnostic applications. As such, a further aspect of the invention provides a method of diagnosing a disorder associated with increased expression of Toll-like Receptor 2. In certain embodiments, the method comprises contacting a test cell with an anti-TLR2 antibody of the invention; determining the level of expression (either quantitatively or qualitatively) of TLR2 by the test cell by detecting binding of the anti-TLR2 antibody to TLR2; and comparing the level of expression of TLR2 by the test cell with the level of expression of TLR2 by a control cell {e.g., a normal cell of the same tissue origin as the test cell or a cell that expresses TLR2 at levels comparable to such a normal cell), wherein a higher level of expression of TLR2 by the test cell as compared to the control cell indicates the presence of a disorder associated with increased expression of TLR2. In certain embodiments, the test cell is obtained from an individual suspected of having a disorder associated with increased expression of TLR2. In certain embodiments, the disorder is an inflammatory disorder or immune mediated disorder, as described hereinbefore.

Therapeutic Efficacy

The inventor has identified that the humanised anti-TLR2 antibody which is provided herein is therapeutically more desirable than the anti-TLR2 murine monoclonal antibodies which are known in the art.

In addition to the structural differences which exist between the light and heavy chain variable domains of the humanised antibodies of the invention and the murine anti-TLR2 antibodies of the prior art, the inventor has also surprisingly identified a number of functional advantages conferred by the humanised antibody of the present invention which would make the use of such an antibody more preferable in a clinical setting.

Without wishing to be bound by the inventor has identified that, when compared to the 11G7 anti-TLR2 murine monoclonal antibody, the fully humanised antibody according to the present invention exhibits superior functional and clinical utility as the antibody antagonises TLR2 function irrespective of whether TLR2 forms a heterodimer with either TLR1 or TLR6.

In relation to the murine TL2.1 antibody, the inventor has identified that the humanised antibody of the present invention is cross reactive to different mammalian forms of TLR2, such as human, murine, rat, pig and monkey, whereas the murine TL2.1 antibody only exhibits binding specificity to human TLR2. Furthermore, the humanised antibody of the present invention includes no murine amino acid residues and accordingly, the likelihood of neutralising antibodies being generated against them when administered to a subject is minimal, when compared to the murine derived TL2.1 antibody.

With regard to the T2.5 antibody, the inventor has surprisingly identified that the T2.5 antibody (a mouse Toll-like Receptor 2 (TLR2) antibody, derived from hybridoma clone T2.5, HyCult Biotechnology b.v., Cell Sciences, Canton, USA: catalogue number 1054) mediates antagonism of TLR2 activation and signalling, with this occurring in a CD32-dependent manner. The inventor has identified that the fully humanised antibodies of the present invention do not require CD32 in order to mediate the suppression of TLR2 signalling, that is, binding to CD32, for example, by the Fc region of the antibody does not have to occur, in order to mediate antagonism of the TLR2 receptor when bound by the Fab portion of the antibody. Accordingly, the antagonism of Toll-like Receptor 2 function which is mediated by the OPN-305 fully humanised monoclonal antibody of the present invention is mediated in a CD32 independent manner. This includes binding to both CD32a and CD32b. This surprising observation, which has been made by the inventor is clinically significant, as the fully humanised antibody of the present invention has potentially greater patient access.

Furthermore, the fully humanised antibodies of the present invention is predicted to bind to an epitope defined by residues present at both the N and C terminals of the TLR2 amino acid sequence. This is in contrast to WO 2005/028509 which states that the epitope bound by the T2.5 monoclonal antibody is located at the N-terminal (only) of the TLR2 sequence.

Furthermore, as exemplified in the comparative examples provided herein, the inventor has confirmed that the fully humanised antibody of the present invention exhibits a reduced immunogenicity profile, that is, that the antibodies are less immunogenic due to a lack of T cell epitopes. Accordingly, antibodies according to the invention will be very unlikely to have a neutralising antibody response raised against them when administered to a human subject. This functional characteristic means that the fully humanised antibody of the present invention is far more desirable for use in a clinical setting that the murine antibodies TL2.1, T2.5 and 11G7 which are known in the art, or to chimeric antibodies or to humanised antibodies which may be developed based on traditional CDR grafting techniques.

Antibodies

An "antibody" is an immunoglobulin, whether natural or partly or wholly synthetically produced. The term also covers any polypeptide, protein or peptides having a binding domain that is, or is homologous to, the binding domain of the humanised antibodies of the invention.

Immunoglobulins typically have a heterotetrameric structure comprising two identical heavy chains and two identical light chains, linked together by disulphide bonds. Each heavy and light chain comprises a variable domain which confers the binding specificity of the antigen, with these domains being known as VH and VL domains for the heavy and light chains respectively. Each chain also comprises at least one constant domain, with the light chain having at a single constant domain, designated the CL domain, while the heavy domain comprises three constant domains, CH1, CH2 and CH3. Some antibody isotypes additionally include a further constant domain referred to as the CH4 domain. In humans, there are 5 different classes of antibodies, namely; IgG, IgA, IgD IgE and IgM.

The Fc domain of an antibody typically comprises the last 2 heavy chain constant region domains of each chain. These dimerise to form the Fc domain which is responsible for mediating the effector functions of the antibody, such as ADCC and complement fixation. The Fc region of the antibody also has a role in the circulatory half-life of the antibody. Modifications can be made to the Fc domain to modulate antibody function.

As antibodies can be modified in a number of ways, the term "antibody" should be construed as extending to any specific binding member, which has the same binding specificity as the humanised antibodies of the present invention. Accordingly, the term "antibody" extends to antibody fragments and homologues as well as to any polypeptide comprising an immunoglobulin binding domain which have binding specificity to Toll-like Receptor 2 and which serve to antagonise TLR2 function.

Furthermore, it is known that fragments of a whole antibody can perform the function of binding antigens. Examples of such binding fragments include, but are not limited to: (i) Fab fragments consisting of the VL, VH, CL and CH1 domains of a heterotetrameric antibody, (ii) F(ab')2 fragments, a bivalent fragment comprising two Fab fragments linked by a disulphide bridge at the hinge region, (iii) Fab' fragment, a Fab fragment with part of the hinge region, (iv) Fd fragments consisting of the VH and CH1 domains of a heterotetrameric antibody, (v) Fv fragments consisting of the VH and VL domains of a heterotetrameric antibody, (vi) scFv (single chain Fv molecules), wherein a VH domain and a VL domain are linked by a peptide linker, (vii) an isolated CDR, such as VHCDR3, and (viii) diabodies, these being multimers of polypeptides which may be multivalent or multispecific fragments produced by gene fusion techniques.

In certain further aspects, the invention also extends to bispecific antibodies. These may include conventional bispecific antibodies which may be prepared by chemical conjugation means, or by hybrid hybridoma cell lines. Alternatively, the bispecific antibodies may be derived from bispecific antibody fragments, such as scFv dimers or diabodies. In certain embodiments, scFv dimers may be used, rather than whole antibodies. Such diabodies can be constructed using only variable domains and therefore are provided without an Fc region, such a structure reducing the possible occurrence of a HAMA or anti-idiotypic immune response.

The amino acid residues in antibody domains are conventionally numbered according to a system devised by Kabat et al. (URL—www.kabatdatabase.com). This numbering is used in the present specification, except where otherwise indicated.

Peptidomimetics

The present invention further extends to peptidomimetics which are based on the antibodies of the present invention or binding fragments thereof. As used herein, the term "peptidomimetic" or "peptide mimetic", refers to molecules which are not polypeptides, but which mimic aspects of their structures and which, in the context of the present invention, bind specifically to Toll-like Receptor 2, in a manner which results in the functional activity of Toll-like Receptor 2 being agonised. Hence, the invention extends to peptidomimetics based on the antibodies of the invention which act as Toll-like Receptor 2 antagonists.

Peptidomimetic antagonists can be prepared by conventional chemical methods (see e.g., Damewood J. R. "Peptide Mimetic Design with the Aid of Computational Chemistry" in Reviews in Computational Biology, 2007, Vol. 9, pp. 1-80, John Wiley and Sons, Inc., New York, 1996; Kazmierski W. K., "Methods of Molecular Medicine: Peptidomimetic Protocols," Humana Press, New Jersey, 1999). Peptidomimetics can be prepared that are Toll-like Receptor 2 antagonists, wherein said peptidomimetics are based on the antibodies of the present invention, and in particular based on the heavy and light chain variable regions. For example, polysaccharides can be prepared that have the same functional groups as peptides. Peptidomimetics can be designed, for example, by establishing the three dimensional structure of a peptide agent in the environment in which it is bound or will bind to a target molecule. The peptidomimetic comprises at least two components, the binding moiety or moieties and the backbone or supporting structure.

The binding moieties are the chemical atoms or groups which will react or form a complex (e.g., through hydrophobic or ionic interactions) with a target molecule, for example, with the amino acid(s) at or near the ligand binding site, such as the Toll-like Receptor 2 epitope comprising the amino acid sequence of SEQ ID NO:3 or SEQ ID NO:4. For example, the binding moieties in a peptidomimetic can be the same as those in a peptide or protein antagonist. The binding moieties can be an atom or chemical group which reacts with Toll-like Receptor 2 in the same or similar manner as the antibodies if the present invention. Examples of binding moieties suitable for use in designing a peptidomimetic for a basic amino acid in a peptide include nitrogen containing groups, such as amines, ammoniums, guanidines and amides or phosphoniums. Examples of binding moieties suitable for use in designing a peptidomimetic for an acidic amino acid include, for example, carboxyl, lower alkyl carboxylic acid ester, sulfonic acid, a lower alkyl sulfonic acid ester or a phosphorous acid or ester thereof.

The supporting structure is the chemical entity that, when bound to the binding moiety or moieties, provides the three dimensional configuration of the peptidomimetic. The supporting structure can be organic or inorganic. Examples of organic supporting structures include polysaccharides, polymers or oligomers of organic synthetic polymers (such as, polyvinyl alcohol or polylactide). It is preferred that the supporting structure possess substantially the same size and dimensions as the peptide backbone or supporting structure. This can be determined by calculating or measuring the size of the atoms and bonds of the peptide and peptidomimetic. In one embodiment, the nitrogen of the peptide bond can be substituted with oxygen or sulphur, for example, forming a polyester backbone. In another embodiment, the carbonyl can be substituted with a sulfonyl group or sulfinyl group, thereby forming a polyamide (e.g., a polysulfonamide). Reverse amides of the peptide can be made (e.g., substituting one or more —CONH-groups for a —NHCO-group). In yet another embodiment, the peptide backbone can be substituted with a polysilane backbone.

These compounds can be manufactured by known methods. For example, a polyester peptidomimetic can be prepared by substituting a hydroxyl group for the corresponding α-amino group on amino acids, thereby preparing a hydroxyacid and sequentially esterifying the hydroxyacids, optionally blocking the basic and acidic side chains to minimize side reactions. Determining an appropriate chemical synthesis route can generally be readily identified upon determining the chemical structure.

Peptidomimetics can be synthesized and assembled into libraries comprising a few to many discrete molecular species. Such libraries can be prepared using well known methods of combinatorial chemistry, and can be screened to determine if the library comprises one or more peptidomimetics which have the desired activity. Such peptidomimetic antagonists can then be isolated by suitable methods.

Accordingly, certain further aspects of the present invention extend to peptidomimetics which are designed based on the paratopes of the Toll-like Receptor 2 binding antibodies of the present invention. In particular, such peptidomimetics are based on the structure of the CDR regions of the antibodies disclosed herein. Techniques for the production of such peptidomimetics will be well known to the person of skill in the art and include the method of Dougall et al. ("Design of pharmacologic agents based on antibody structure", Trends in Biotechnology. 1994. 12. p 372-379). Further, the techniques of Saragovi et al. (Saragovi, et al., "Design and Synthesis of a Mimetic from an Antibody Complementarity-Determining Region", Science 253:792-795 (1991) and Saragovi et al., "Loops and Secondary Structure Mimetics: Development and Applications in Basic Science and Rational Drug Design", Biotechnology 10: 773-778 (1992)). Such peptidomimetics may, in particular be based on the CDR3 of the heavy chain. Williams, et al. (Williams et al., "Design of Bioactive Peptides Based on Antibody Hypervariable Region Structures", J. Biol. Chem. 266: 5182-5160 (1991)), describes the isolation and synthesis of conformationally constrained peptides derived from the complementarity determining regions of the light chain of antibodies. This CDR is particularly important in the binding specificity of an antibody as a consequence of the complex genetic mechanism which influences its structure, which cause it to have medium or long loops which have diverse patterns of interactions. The conformational properties of peptide loops or reverse turns are considered important mediators in the biological activity of polypeptides. Turns provide for suitable orientations of binding groups essential for bioactivity by stabilizing a folded conformation in a small molecule and may be involved in both binding and recognition sites.

The present invention further extends to antibody mimetics, such as Affibodies, domain antibodies, Nanobodies, Uni-Bodies, DARPins, Anticalins, Avimers, Versabodies, and Duocalins which are based on the Toll-like Receptor 2 antibodies of the present invention. A wide variety of antibody mimetic technologies are known to the person skilled in the art. For example, so called, domain antibodies (Domantis, UK) are small functional binding units of antibodies which correspond to the variable regions of either the light or heavy chains of human antibodies. Directions for the production of such domain antibodies can be found in U.S. Pat. No. 6,291,158, U.S. Pat. No. 6,582,915 and U.S. Pat. No. 6,593,081. Nanobodies are antibody-derived therapeutic proteins which contain unique structural and functional properties of naturally occurring heavy chain antibodies found in camelids. Unibodies are a further antibody fragment technology, based upon the removal of the hinge region of IgG4 antibodies. The deletion of the hinge region results in a molecule which is approximately half the size of a traditional IgG4 antibody and which has a univalent binding region. Unibodies preserve the property of IgG4 antibodies of being inert and therefore not inducing immune responses. Hence, like IgG4 antibody based therapeutics, such as the embodiments of the antibodies of the present invention described herein, Unibodies can be used to antagonise specific functions of cells, but cell death will typically not occur as the Unibody, like an IgG4 antibody, will not mediate an immune response against the target to which it is bound. Unibodies are cleared from the body at a similar rate to IgG4 and bind with a similar binding affinity to their target antigens.

Further binding molecules include: affibody molecules (U.S. Pat. No. 5,831,012), DARPins (designed ankyrin repeat proteins) (International PCT Patent Application Publication WO 02/20565) and anticalins (U.S. Pat. No. 7,250,297 and WO 99/16873). Verabodies are a further antibody mimetic technology. Versabodies (Amunix, US Patent Application Publication No. 200710191272) are small proteins, referred to as microproteins, of 3-5 kDa with greater than 15% cysteine residues, which form a high disulphide bond density scaffold which replaces the hydrophobic core which protein typically exhibit Avimers are another type of antibody mimetic. Avimers originate from the recombination of families of human serum proteins. They are single protein chains composed of modular binding domains, each of which is designed to bind to a particular target site. The avimers can bind simultaneously to sites on a single protein target and/or sites on multiple protein targets. Known as multi-point attachment or avidity, this binding mechanism mimics the way cells and molecules interact in the body, supports the generation of antagonists and agonists, and results in drugs with multiple functions and potent activity. Avimers libraries can be produced according to WO 2004/044011 incorporated herein by reference and particularly Example 6 on page 99, and for example US Patent Application (Publication) Nos. US 2005/0053973, US2005/0089932, US2005/0164301. Avimers libraries are also available commercially from Avidia Inc, Mountain View, Calif., USA.

Antibody Production

The antibodies and binding members of the invention may be produced wholly or partly by chemical synthesis. For example, the antibodies and binding members of the invention can be prepared by techniques which are well known to the person skilled in the art, such as standard liquid peptide synthesis, or by solid-phase peptide synthesis methods. Alternatively, the antibodies and binding members may be prepared in solution using liquid phase peptide synthesis techniques, or further by a combination of solid-phase, liquid phase and solution chemistry.

The present invention further extends to the production of the antibodies or binding members of the invention by expression of a nucleic acid which encodes at least one amino acid which comprises an antibody of the invention in a suitable expression system, such that a desired peptide or polypeptide can be encoded.

For example, a nucleic acid encoding the amino acid light chain and a second nucleic acid encoding an amino acid heavy chain can be expressed to provide an antibody of the present invention.

Accordingly, in certain further aspects of the invention, there is provided nucleic acids encoding amino acid sequences which form the antibodies or binding members of the present invention.

Typically, nucleic acids encoding the amino acid sequences which form antibodies or binding members of the present invention can be provided in an isolated or purified form, or provided in a form which is substantially free of material which can be naturally associated with it, with the exception of one or more regulatory sequences. Nucleic acid which expresses an antibody or binding member of the invention may be wholly or partially synthetic and may include, but is not limited to DNA, cDNA and RNA.

Nucleic acid sequences encoding the antibodies or binding members of the invention can be readily prepared by the skilled person using techniques which are well known to those skilled in the art, such as those described in Sambrook et al. "Molecular Cloning", A laboratory manual, cold Spring Harbor Laboratory Press, Volumes 1-3, 2001 (ISBN-0879695773), and Ausubel et al. Short Protocols in Molecular Biology. John Wiley and Sons, 4$^{th}$ Edition, 1999 (ISBN-0471250929). Said techniques include (i) the use of the polymerase chain reaction (PCR) to amplify samples of nucleic acid, (ii) chemical synthesis, or (iii) preparation of cDNA sequences. DNA encoding antibodies or binding members of the invention may be generated and used in any suitable way known to those skilled in the art, including taking encoding DNA, identifying suitable restriction enzyme recognition sites either side of the portion to be expressed, and cutting out said portion from the DNA. The excised portion may then be operably linked to a suitable promoter and expressed in a suitable expression system, such as a commercially available expression system. Alternatively, the relevant portions of DNA can be amplified by using suitable PCR primers. Modifications to the DNA sequences can be made by using site directed mutagenesis.

Nucleic acid sequences encoding the antibodies or binding members of the invention may be provided as constructs in the form of a plasmid, vector, transcription or expression cassette which comprises at least one nucleic acid as described above. The construct may be comprised within a recombinant host cell which comprises one or more constructs as above. Expression may conveniently be achieved by culturing, under appropriate conditions, recombinant host cells containing suitable nucleic acid sequences. Following expression, the antibody or antibody fragments may be isolated and/or purified using any suitable technique, then used as appropriate.

Systems for the cloning and expression of a polypeptide in a variety of different host cells are well known. Suitable host cells include bacteria, mammalian cells, yeast, insect and baculovirus systems. Mammalian cell lines available in the art for expression of a heterologous polypeptide include Chinese hamster ovary (CHO) cells, HeLa cells, baby hamster kidney cells and NS0 mouse myeloma cells. A common, preferred bacterial host is *E. coli*. The expression of antibodies and antibody fragments in prokaryotic cells such as *E. coli* is well established in the art. Expression in eukaryotic cells in culture is also available to those skilled in the art as an option for production of a binding member.

General techniques for the production of antibodies are well known to the person skilled in the field, with such methods being discussed in, for example, Kohler and Milstein (1975) Nature 256: 495-497; U.S. Pat. No. 4,376,110; Harlow and Lane, Antibodies: a Laboratory Manual, (1988) Cold Spring Harbor. Techniques for the preparation of recombinant antibody molecules are described in the above references and also in, for example, European Patent Number 0,368,684.

In certain embodiments of the invention, recombinant nucleic acids comprising an insert coding for a heavy chain variable domain and/or for a light chain variable domain of antibodies or binding members are employed. By definition, such nucleic acids comprise encode single stranded nucleic acids, double stranded nucleic acids consisting of said coding nucleic acids and of complementary nucleic acids thereto, or these complementary (single stranded) nucleic acids themselves.

Furthermore, nucleic acids encoding a heavy chain variable domain and/or a light chain variable domain of antibodies can be enzymatically or chemically synthesised nucleic acids having the authentic sequence coding for a naturally-occurring heavy chain variable domain and/or for the light chain variable domain, or a mutant thereof.

An antibody of the invention may be produced by recombinant means, not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, Ipp, or heat-stable enterotoxin II leaders.

Isolated

The term "isolated", when used in reference to the fully humanised antibodies of the invention, or to binding members derived therefrom, or polypeptides which encode the same, refers to the state in which said antibodies, binding members or nucleic acids (polynucleotides) are provided in an isolated and/or purified form, that is they have been separated, isolated or purified from their natural environment, and are provided in a substantially pure or homogeneous form, or, in the case of nucleic acid, free or substantially free of nucleic acid or genes of origin other than the sequence encoding a polypeptide with the required function. Accordingly, such isolated antibodies, binding members and isolated nucleic acids will be free or substantially free of material with which they are naturally associated, such as other polypeptides or nucleic acids with which they are found in their natural environment, or the environment in which they are prepared (e.g. cell culture) when such preparation is by recombinant DNA technology practised in vitro or in vivo.

Antibodies, binding members and nucleic acids may be formulated with diluents or adjuvants and still, for practical purposes, be considered as being provided in an isolated form. For example the antibodies and binding members can be mixed with gelatin or other carriers if used to coat microtitre plates for use in immunoassays, or will be mixed with pharmaceutically acceptable carriers or diluents when used in diagnosis or therapy. The antibodies or binding members may be glycosylated, either naturally or by systems of heterologous eukaryotic cells (e.g. CHO or NS0 cells, or they may be (for example if produced by expression in a prokaryotic cell) unglycosylated.

Heterogeneous preparations comprising anti-TLR2 humanised antibody molecules also form part of the invention. For example, such preparations may be mixtures of antibodies with full-length heavy chains and heavy chains lacking the C-terminal lysine, with various degrees of glycosylation and/or with derivatized amino acids, such as cyclization of an N-terminal glutamic acid to form a pyroglutamic acid residue.

Administration

The monoclonal antibody or binding member of the present invention may be administered alone but will preferably be administered as a pharmaceutical composition which will generally comprise a suitable pharmaceutically acceptable excipient, diluent or carrier selected depending on the intended route of administration. Examples of suitable pharmaceutical carriers include; water, glycerol, ethanol and the like.

The monoclonal antibody or binding member of the present invention may be administered to a patient in need of treatment via any suitable route. Typically, the composition can be administered parenterally by injection or infusion. Examples of preferred routes for parenteral administration include, but are not limited to; intravenous, intracardial, intraarterial, intraperitoneal, intramuscular, intracavity, subcutaneous, transmucosal, inhalation or transdermal. Routes of administration may further include topical and enteral, for example, mucosal (including pulmonary), oral, nasal, rectal.

In embodiments where the composition is delivered as an injectable composition, for example in intravenous, intradermal or subcutaneous application, the active ingredient can be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection or, Lactated Ringer's injection. Preservatives, stabilisers, buffers, antioxidants and/or other additives may be included, as required.

The composition may also be administered via microspheres, liposomes, other microparticulate delivery systems or sustained release formulations placed in certain tissues including blood.

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition ISBN 0-912734-04-3 and Pharmaceutical Dosage Forms and Drug Delivery Systems; Ansel, H. C. et al. 7th Edition ISBN 0-683305-72-7, the entire disclosures of which is herein incorporated by reference.

The composition of the invention is typically administered to a subject in a "therapeutically effective amount", this being an amount sufficient to show benefit to the subject to whom the composition is administered. The actual dose administered, and rate and time-course of administration, will depend on, and can be determined with due reference to, the nature and severity of the condition which is being treated, as well as factors such as the age, sex and weight of the subject being treated, as well as the route of administration. Further due consideration should be given to the properties of the composition, for example, its binding activity and in-vivo plasma life, the concentration of the antibody or binding member in the formulation, as well as the route, site and rate of delivery.

Dosage regimens can include a single administration of the composition, or multiple administrative doses of the composition. The compositions can further be administered sequentially or separately with other therapeutics and medicaments which are used for the treatment of the condition for which the antibody or binding member of the present invention is being administered to treat.

Examples of dosage regimens which can be administered to a subject can be selected from the group comprising, but not limited to; 1 μg/kg/day through to 20 mg/kg/day, 1 μg/kg/day through to 10 mg/kg/day, 10 μg/kg/day through to 1 mg/kg/day. In certain embodiments, the dosage will be such that a plasma concentration of from 1 μg/ml to 100 μg/ml of the antibody is obtained. However, the actual dose of the composition administered, and rate and time-course of administration, will depend on the nature and severity of the condition being treated. Prescription of treatment, e.g. decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

DEFINITIONS

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

As used herein, terms such as "a", "an" and "the" include singular and plural referents unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like.

The terms "specifically binds", "selectively binds" or "binding specificity" refer to the ability of the fully humanised antibodies or binding compounds of the invention to bind to a target epitope present on Toll-like Receptor with a greater affinity than that which results when bound to a non-target epitope. In certain embodiments, specific binding refers to binding to a target with an affinity that is at least 10, 50, 100, 250, 500, or 1000 times greater than the affinity for a non-target epitope. In certain embodiments, this affinity is determined by an affinity ELISA assay. In certain embodiments, affinity can be determined by a BIAcore assay. In certain embodiments, affinity can be determined by a kinetic method. In certain embodiments, affinity can be determined by an equilibrium/solution method.

As used herein, the term "effective amount" or "therapeutically effective amount" means the amount of an agent, binding compound, small molecule, fusion protein or peptidomimetic of the invention which is required to suppress TLR2-mediated inflammation in the kidney or which reduces the severity of and/or ameliorates a TLR2 mediated renal disease or at least one symptom thereof or a condition associated therewith.

As used herein, the term "prophylactically effective amount" relates to the amount of a composition which is required to prevent the initial onset, progression or recurrence of a TLR2-mediated disease, or inflammatory condition, or at least one symptom thereof in a subject following the administration of the compounds of the present invention.

As used herein, the term "treatment" and associated terms such as "treat" and "treating" means the reduction of the progression, severity and/or duration of a TLR2 mediated condition or at least one symptom thereof, wherein said reduction or amelioration results from the administration of a binding compound which has specificity for the TLR2 binding epitope of the present invention. The term 'treatment' therefore refers to any regimen that can benefit a subject. The treatment may be in respect of an existing condition or may be prophylactic (preventative treatment). Treatment may include curative, alleviative or prophylactic effects. References herein to "therapeutic" and "prophylactic" treatments are to be considered in their broadest context. The term "therapeutic" does not necessarily imply that a subject is treated until total recovery. Similarly, "prophylactic" does not necessarily mean that the subject will not eventually contract a disease condition.

As used herein, the term "subject" refers to an animal, preferably a mammal and in particular a human. In a particular embodiment, the subject is a mammal, in particular a human. The term "subject" is interchangeable with the term "patient" as used herein.

The present invention will now be described with reference to the following examples which are provided for the purpose of illustration and are not intended to be construed as being limiting on the present invention.

EXAMPLES

Example 1

Production of Fully Humanised Monoclonal Antibody

The TLR2 antagonistic antibodies of the present invention are typically fully humanised antibodies. That is, the antibodies are fully human in origin, and therefore do not contain regions or amino acid combinations derived from non-human species, such as mice.

One method of producing the fully humanised antibodies of the invention is through the use of composition human antibody technology (Antitope, UK) as described in International PCT Patent Application No. WO 2006/082406. Such antibodies are composite proteins comprising 2 or more segments of amino acid sequence derived from human antibodies. The segments can be selected such that the presence of T-cell epitopes in the final antibody is avoided, for example by screening the residues, particularly of the light and heavy chain variable regions to ensure that they do not comprise MHC class II binding motifs, or that they that do not comprise residues which anchor the binding of peptides to MHC class II. Furthermore, in-silico methods of analysing the variable regions of the fully humanised antibody of the invention to ensure that no T cell epitopes are present.

In producing a fully humanised antibody using the composite human antibody technique, the final antibody is produced which comprises a composition of many sequence segments, all of which are human in origin, and all of which are derived from different human antibodies. Briefly, the technique involves the steps of; analysing the heavy and light chain variable regions of a starting monoclonal antibody, for example a murine or chimeric antibody which has binding specificity for Toll-like Receptor 2 in order to identify the complementarity determining regions (CDRs). Protein models of the antibody variable regions are then generated using existing antibody structures as templates using Swiss PDB. These structural models are then analysed to identify important "constraining" amino acids in the variable domain regions of the original antibody that are likely to be essential for the binding properties of the antibody. Residues contained within the CDR regions (as defined using both the Kabat and Chothia definitions), together with a number of framework residues are typically important. Structural information from the protein model is used to identify and compare residues which are critical for antibody confirmation and binding with structurally equivalent residues from existing antibody structures and sequence databases. These amino acids may then be candidates for inclusion in one or more variants of the final humanised sequences. In preparing the antibody of the present invention, both the VH and VK sequences of the murine anti-TLR2 antibody on which the fully humanised antibody of the present invention is based (mouse Toll-like Receptor 2 (TLR2) antibody, derived from hybridoma clone T2.5, HyCult Biotechnology b.v., Cell Sciences, Canton, USA: catalogue number 1054) were seen to contain typical framework residues, especially in the VH where the antibody has very common sequence configurations at critical positions e.g. Kabat residues 45-49 (LEWIG) and 92-94 (CAR).

Sequences of the source monoclonal heavy and light chain variable region amino acid sequences are then compared with corresponding segments of human variable region sequences in order to identify potential heavy and light chain human sequences for possible inclusion in the final humanised sequence. Final, fully humanised heavy and light chains are then designed entirely from segments of human variable region sequences.

The fully humanised antibody is designed and produced by firstly synthesising VH and VK region genes using a series of overlapping oligonucleotides that were annealed, ligated and PCR amplified to give full length synthetic V regions. The polynucleotide sequence was then cloned directly into a suitable expression vector, examples of which will be well known to the person skilled in the art, such as an expression vector system which encodes for an antibody, such as IgG. In the case of the expression vector used in the production of the OPN-305 antibody of the present invention, the expression vector system relates to an IgG4 derived sequence comprising a modified hinge region (a S241P substitution) as well as heavy chains and a kappa light chain. The heavy and light chains are thereafter stably transfected into NS0 cells via electroporation and selected using 200 nM methotrexate (Sigma, catalogue number M8407). Metotrexate resistant colonies were tested for IgG expression levels.

Although NS0 cells were used, any suitable cell line which is known to the person skilled in the art could be used. In particular the use of mammalian cells within a mammalian cell culture is preferred as a platform for the production of the antibodies and binding fragments of the invention. The use of mammalian cells are particularly preferred due to the N-glycosylation profile which is applied to the protein, as such glycosylation profiles are similar to those found on human proteins. Cell lines typically employed for mammalian cell culture include CHO, NS0 hybridoma cells, baby hamster kidney (BHK) cells, and PER.C6™ human cells. The most commonly employed mammalian cell line used for mammalian cell culture at production scale volumes are the CHO and NS0 cell lines. These cell types are relatively easy to genetically engineer, have been extensively characterized, are relatively easy to grow at large scale, and can excrete high titers of recombinant proteins in solution. Both CHO and NS0 cell lines can produce high protein expression levels.

In addition to mammalian cell based protein expression platforms, the use of plant based expression systems, or transgenic animal systems may also be employed for the use of the production of the proteins of the invention.

The composite antibodies were then purified from cell culture supernatants on a Protein A sepharose column (GE Healthcare catalogue number 110034-93) and quantified by OD280 nm, using a calculated extinction coefficient where Ec(0.1%)=1.43. The purified antibodies were then tested in a competition ELISA assay to confirm binding to Toll-like Receptor 2. This binding may be compared to the binding of a reference antibody, such as a biotinylated form of a Toll-like Receptor 2 binding antibody upon which design of the fully human antibody was based. In particular, absorbance from the ELISA competition assay can be plotted against sample concentration and straight lines fitted through each of the data sets pertaining to the fully human and original biotinylated antibody. The equations of the lines were used to calculate the concentration required to inhibit biotinylated reference antibody binding to TLR2 by 50% (the so called, IC50 value). The IC50 value can be used to calculate the fold difference in binding efficiency. The determined binding efficiency can be an important determination of the specificity of the fully humanised antibody which is produced. Further comparisons, for example, comparing the fully humanised antibody to a chimeric or murine antibody, which has binding specificity for the same antigen, can also be performed.

Example 2

Determination of Binding Properties of OPN-305 Monoclonal Antibody

The inventor has surprisingly identified that the T2.5 TLR2 antagonistic murine monoclonal antibody requires binding to CD32 in order to fully antagonise Toll-like Receptor 2 function. Experimentation was therefore performed to confirm that this functional limitation associated with the use of the T2.5 antibody was not also associated with the use of the OPN-305 monoclonal antibody in order to mediate its effect of neutralising Toll-like Receptor 2 biological activity.
Materials and Methods:

THP-1 cells are human peripheral blood monocytic cells. In response to Toll-like Receptor ligands, the transcription factor NF-kappaB and other transcription factors are activated in THP1 cells. The THP-1 Blue cell line has been stably transfected with a reported plasmid encoding the secreted embryonic alkaline phosphatase (SEAP) gene under the control of a promoter inducible by several transcription factors, such as NF-kappaB and AP-1. The THP-1 CD14 Blue cell line variant over expresses the cell surface protein CD14 for enhanced sensitivity. The resulting THP-1-CD14 Blue cells are resistant to the selectable markers Zeocin and blasticidin. Upon TLR stimulation, THP-1 Blue cells activate transcription factors and subsequently the secretion of SEAP which is then detectable using the QUANTI-Blue reporter system. QUANTI-Blue is a colorimetric enzymatic assay developed to determine secreted alkaline phosphatase (SEAP) activity in the supernatants of cell cultures. In the presence of SEAP, QUANTI-Blue medium changes to a purple-blue colour that can easily be detected with the naked eye, or quantified by reading the optical density (OD) at 625-655 nm.

THP1 CD14 Blue cells were incubated with the OPN-305 anti-TLR2 monoclonal antibody (1 µg/ml) premixed with anti-CD32a antibody (RnD #AF1875) or the anti-CD32b antibody (RnD #AF1330) or goat IgG in the range 5 µg/ml-0.18 µg/ml) for 5 minutes at 37° C. before stimulation with 20 ng/ml of the TLR1/TLR2 agonist Pam3CSK4. The OPN-305 monoclonal antibody is a fully humanised antibody having the light chain defined herein as SEQ ID NO:2 and a heavy chain as defined herein in SEQ ID NO:5.

Cells were then incubated overnight at 37° C. Supernatants were then removed and heat inactivated before addition of QUANTI-Blue (Invivogen, San Diego, USA). Colorimetric changes representing NF-kB activation were measured at 650 nm using a luminometer.

The results are shown in FIG. 9, these results illustrating that the functional activity of OPN-305 as a Toll-like Receptor 2 antagonist is not blocked by the addition of anti-CD32a/b antibodies. This therefore indicates that the Toll-like Receptor 2 neutralising activity mediated by OPN-305 is not dependent on binding to CD32a or CD32b.

Example 3

Role of CD32 in Toll-Like Receptor 2 Antagonism

The results of Example 2 suggest that antagonism of Toll-like Receptor 2 by the OPN-305 fully humanised antibody of the invention is not dependent upon that antibody binding to CD32 (either CD32a or CD32b)

In order to confirm this, and to provide a comparison to other TLR2 antagonistic antibodies which are known in the field, such as the T2.5 murine TLR2 monoclonal antibody (OPN-301), further experimentation was performed.
Materials and Methods:

THP-1 CD14 Blue cells (Invivogen, San Diego, USA) were preincubated with doses of antibodies which block CD32a or CD32b.

Figure 10A:
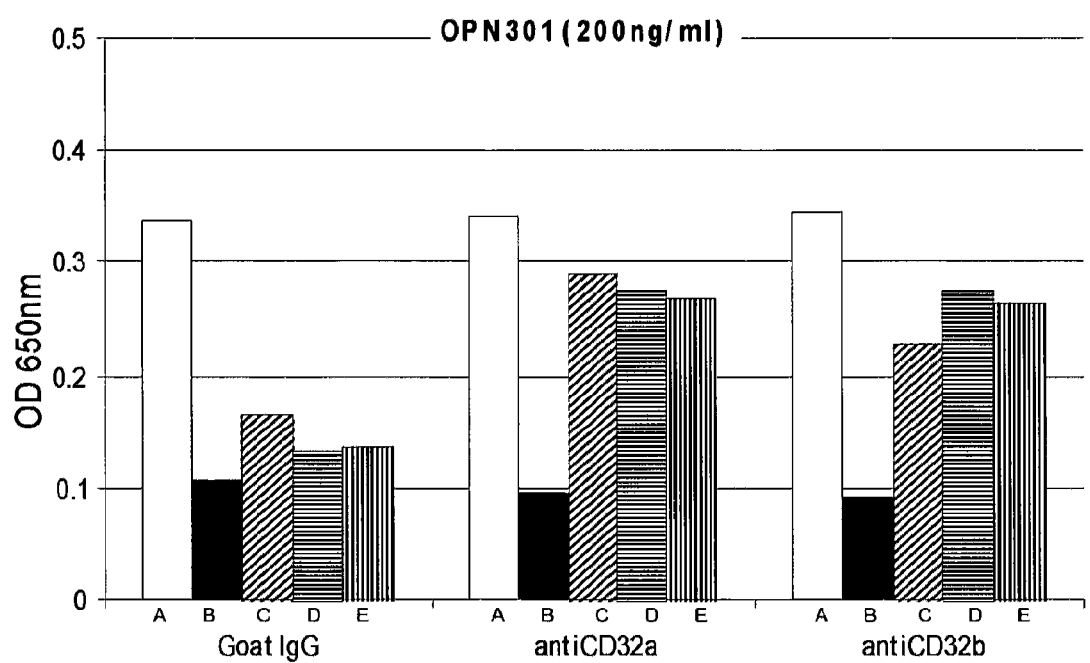
In FIG. 10A, column A relates to cells stimulated with Pam3CSK4 only.
Figure 10B:
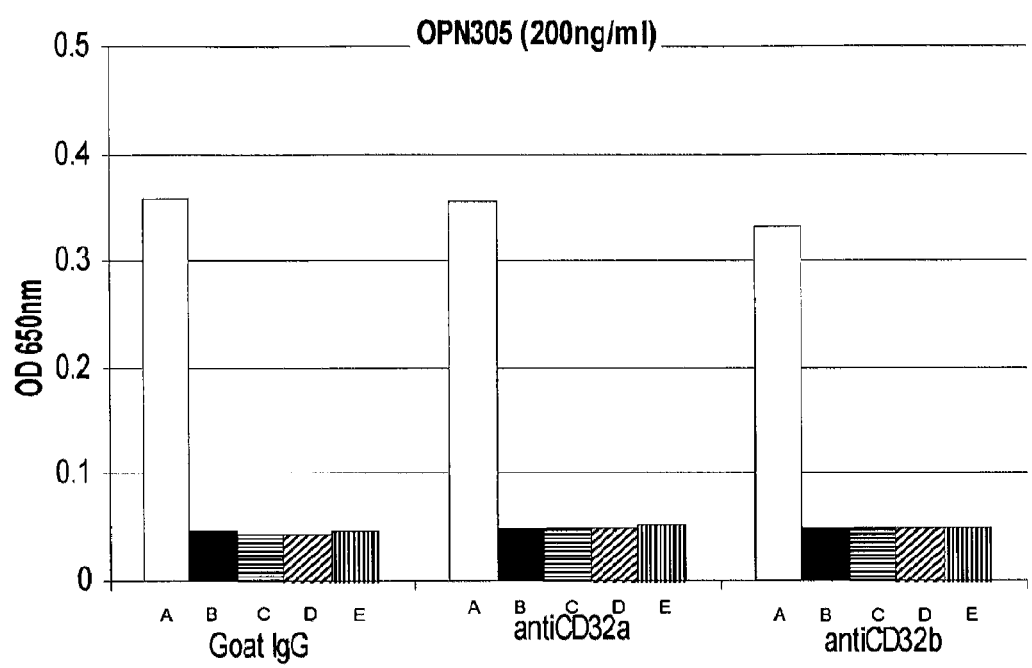
In FIG. 10B, column A relates to cells stimulated with Pam3CSK4 only. Column B relates to cells exposed to the OPN-305 antibody. Column C relates to OPN305 antibody along with 0.4µg/ml anti-CD32a/b or a control goat IgG antibody. Column D relates to OPN305 antibody along with 2 µg/ml anti-CD32a/b antibody or a control goat IgG antibody. Column E relates to OPN305 antibody, plus 10 µg/ml anti-CD32a/b antibody or a control goat IgG antibody.

The pre-incubated THP-1 CD14 Blue cells were incubated with increasing doses of (i) an anti-human FcgammaRIIa (CD32a) antibody (R&D Systems, catalogue number AF1875, as used in the previous example), (ii) an anti-human FcgammaRII (CD32) antibody (R&D Systems, catalogue number AF1330) or (iii) an isotype control antibody (goat IgG (R&D systems, catalogue number AB-108-C). The cells then had either 200 ng/ml of the murine anti-TLR2 antibody T2.5 (OPN-301) or the fully humanised OPN-305 antibody added. The cells were then stimulated with 100 ng/ml of the TLR2 agonist Pam3CSK4 (Invivogen) overnight.
Results NF-kB dependent SEAP production was measured in cell supernatants. FIG. 10A shows the results for cells exposed to the OPN-301 (T2.5 murine anti-TLR2 antibody). FIG. 10B shows the results for cells exposed to the OPN-305 fully humanised TLR2 antagonist antibody. In FIG. 10A, column A relates to cells stimulated with Pam3CSK4 only. Column B relates to cells exposed to the OPN-301 antibody. Column C relates to OPN301 antibody along with 0.4 ug/ml anti-CD32a/b or a control goat IgG antibody. Column D relates to OPN301 antibody along with 2 ug/ml anti-CD32a/b antibody or a control goat IgG antibody. Column E relates to OPN301 antibody, plus 10 ug/ml anti-CD32a/b antibody or a control goat IgG antibody.

In FIG. 10B, column A relates to cells stimulated with Pam3CSK4 only. Column B relates to cells exposed to the OPN-305 antibody. Column C relates to OPN305 antibody along with 0.4 ug/ml anti-CD32a/b or a control goat IgG antibody. Column D relates to OPN305 antibody along with 2 ug/ml anti-CD32a/b antibody or a control goat IgG antibody. Column E relates to OPN305 antibody, plus 10 ug/ml anti-CD32a/b antibody or a control goat IgG antibody.

A comparison of the data shown in the 2 figures clearly shows that TLR2 antagonism which is mediated by OPN-305 is not dependent on the antibody interacting with CD32, as blocking of CD32 with a CD32a or CD32 specific antibody has no effect on the TLR2 neutralising ability of OPN305. In contrast, the murine T2.5 antibody (OPN-301) is shown to be dependent on binding to CD32 in order to mediate complete neutralisation of Toll-like Receptor 2 function activity. Without wishing to be bound by theory, the inventor therefore predicts that, in mediating TLR2 antagonism, the OPN-301 antibody binds to TLR2 and also CD32, this interaction with CD32 being necessary to mediate antagonism of Toll-like Receptor 2. There is therefore a functional difference between the mechanism of action used by the OPN-305 antibody and the OPN-301 antibody in relation to antagonising Toll-like Receptor 2 functional activity. Hence, the TLR2 antagonistic activity of OPN-301 can be blocked by blocking binding to CD32. However, blocking the ability of OPN-305 to bind to CD32, CD32a or CD32b does not affect it's ability to antagonise Toll-like Receptor 2 functional activity.

Example 4

Confirmation of Toll-Like Receptor 2 Binding Specificity of OPN-305

The experiment was designed to confirm that the OPN-305 monoclonal antibody of the invention exhibits binding specificity for Toll-like Receptor 2 and in particular human Toll-like Receptor 2.
Materials and Methods:

HEK 293 (human embryo kidney 293) cells stably transfected with Toll-like Receptor 1 and Toll-like Receptor 2 in order to allow formation of a TLR1/TLR2 heterodimer were incubated with 1.0 µg/ml of a biotinylated form of the murine anti-TLR2 antibody OPN-301 (T2.5) either alone or in the presence of 1.0 µg or 10 µg/ml of the fully humanised anti-TLR2 antibody OPN-305 or of an OPN-305 IgG4 isotype control antibody for 30 minutes on ice.

The OPN-301 monoclonal antibody is a murine IgG1 anti-TLR2 antibody (mouse Toll-like Receptor 2 (TLR2) antibody, clone T2.5, HyCult Biotechnology b.v., Cell Sciences, Canton, USA: catalogue number 1054).

The OPN-305 monoclonal antibody is a fully human antibody having the light chain defined herein as SEQ ID NO:2 and a heavy chain as defined herein as SEQ ID NO:5.

Figure 11:
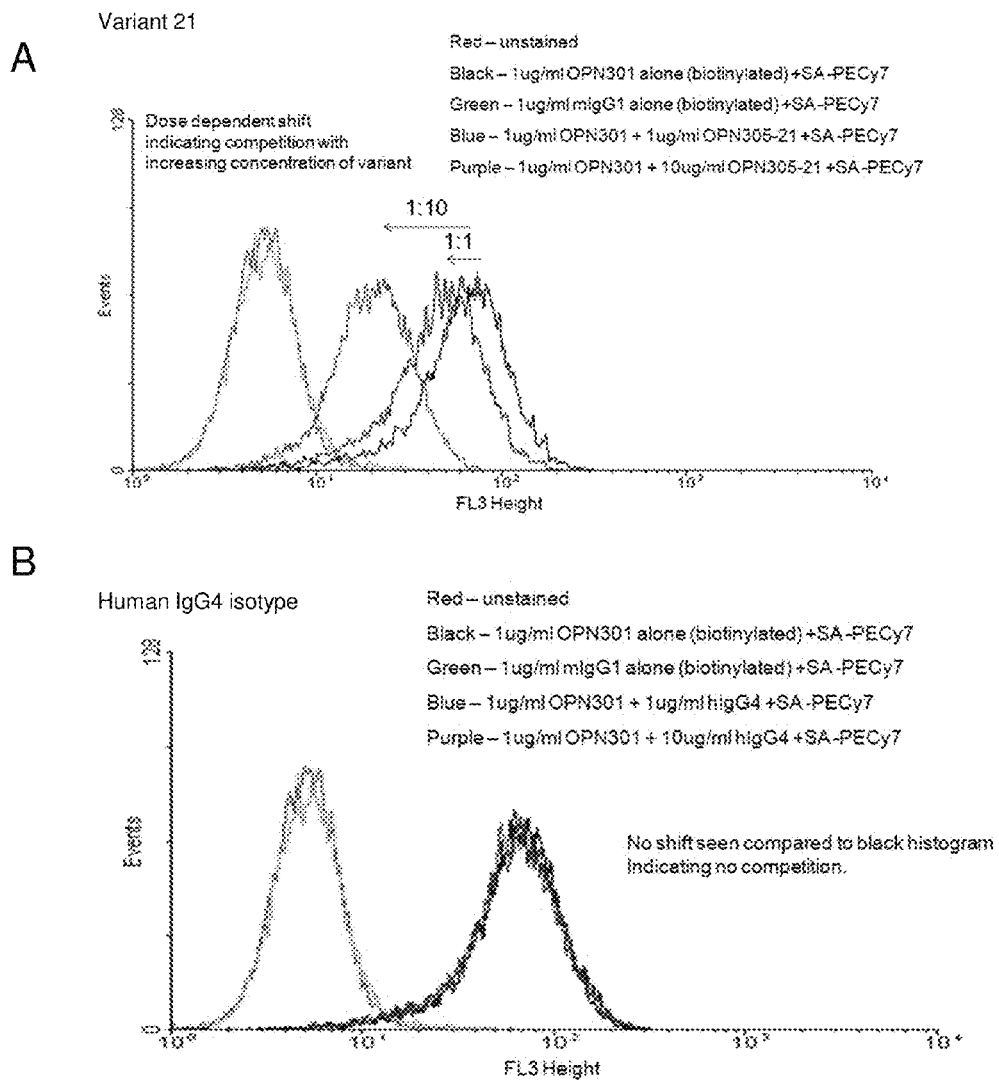
FIG. 11 shows the results of FACS analysis which shown that OPN-305 has binding specificity for human Toll-like Receptor 2 (FIG. 11A), whereas an IgG4 isotype control antibody did not compete with OPN-301 to bind to Toll-like Receptor 2 (FIG. 11B)

Cells were then washed and incubated with streptavidin conjugated to PECy7 for a further 30 minutes. Binding was measured using FACScalibur (Becton Dickinson). The results are shown in FIG. 11.

FIG. 11A relates to the binding of OPN-305 (labelled as variant 21). Moving from left to right, the darkest line of the first peak relates to the red line. The lighter line in the first peak relates to the green line. Moving right, the third, fourth and fifth peaks are the purple, blue and black peaks respectively. Binding of OPN-305 was demonstrated by a shift to the left of the blue and purple histograms (representing OPN-301 and OPN-305) compared to OPN-301 alone (black histograms) which demonstrates than OPN-305 is competing with OPN-301 for binding to human TLR2 on the HEK cells. In conclusion, FIG. 11A shows a dose dependent shift of the peaks, this indicating competition in binding between OPN-301 and OPN-305 for human Toll-like Receptor 2.

FIG. 11B shows the results of binding with the IgG4 isotype control. As the IgG4 isotype control antibody does not have binding specificity for TLR2, it does not compete for binding. There is therefore no shift in the black, purple or blue peaks, which are grouped together and represented as the second peak as shown on the right hand side of FIG. 11B. The peak on the left hand side relates to the red peak (darker line) and the green peak (lighter line). These results therefore confirm that OPN-305 has binding specificity for human Toll-like Receptor 2.

Example 5

Cross Reactivity of OPN-305 to Murine Toll-Like Receptor 2

Having determined in Example 4 that OPN-305 exhibits binding specificity to human Toll-like Receptor 2, this experiment assessed whether the OPN-305 monoclonal antibody exhibited Toll-like Receptor 2 intra-species cross-reactivity, which would allow OPN-305 to bind to other forms of mammalian Toll-like Receptor 2, such as murine Toll-like Receptor 2.

Materials and Methods:

J774 mouse macrophages were cultured at $1\times10^6$/ml in the presence of 5 µg/ml OPN-305 (referred to as OPN-305-21), OPN-301 (T2.5) or the relevant isotype control antibody (murine IgG1 for OPN-301 and human IgG4 for OPN-305) for 6 hours at 37° C. Cells were exposed to the TLR2 agonist HKLM (Invivogen, San Diego, USA, catalogue number tlr-kit2). HKLM is a freeze dried heat-killed preparation of *Listeria Monocytogenes* (LM), a facultative intracellular gram positive bacteria. Supernatants were then removed and murine TNF-α levels were measured by specific ELISA duoset from RnD systems (R&D Systems).

Results

Figure 12:
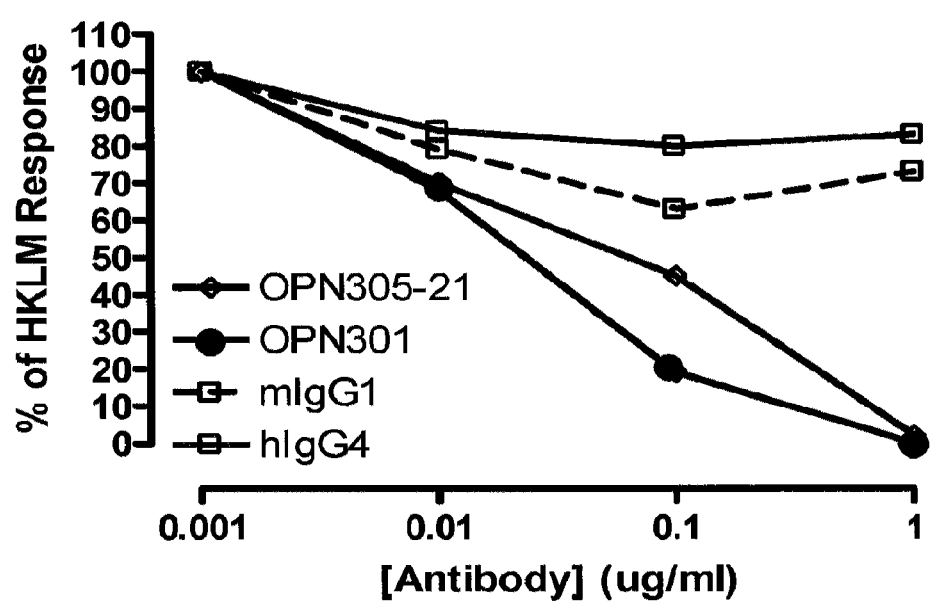
FIG. 12 shows that OPN-305 (OPN-305-21) suppresses murine TLR2 responses in an equivalent manner to the murine OPN-301 antibody.

The results are shown in the graph of FIG. 12. This shows that OPN-305 suppresses murine TLR2 responses in a broadly similar manner to the inhibition of OPN-301. Accordingly, OPN-305 is cross-reactive in that it binds to Toll-like Receptor 2 expressed on the surface or murine cells.

In conclusion, OPN-305 has been shown to suppress TNF-α secretion from murine J774 macrophages which were stimulated with a TLR2 agonist.

Example 6

Cross Reactivity of OPN-305 to Monkey Toll-Like Receptor 2

Further experiments were performed to determine the binding specificity of OPN-305 for Toll-like Receptor 2 expressed on monkey cells. This would identify whether the OPN-305 antibody was cross-reactive to a wider variety of mammalian forms of Toll-like Receptor 2, than just human and murine forms.

Binding of OPN-305 to monkey Toll-like Receptor 2 was determined by both direct antibody and competition binding assay.

(i) Direct Binding

Whole blood cells from cynomologus monkeys were incubated with 1.0 µg/ml of OPN-305 or an IgG4 isotype control antibody for 30 minutes at room temperature, then incubated with PharmLyse (BD Biosciences) to lyse red blood cells, followed by detection with FITC labelled anti-human IgG4.

Figure 13A:
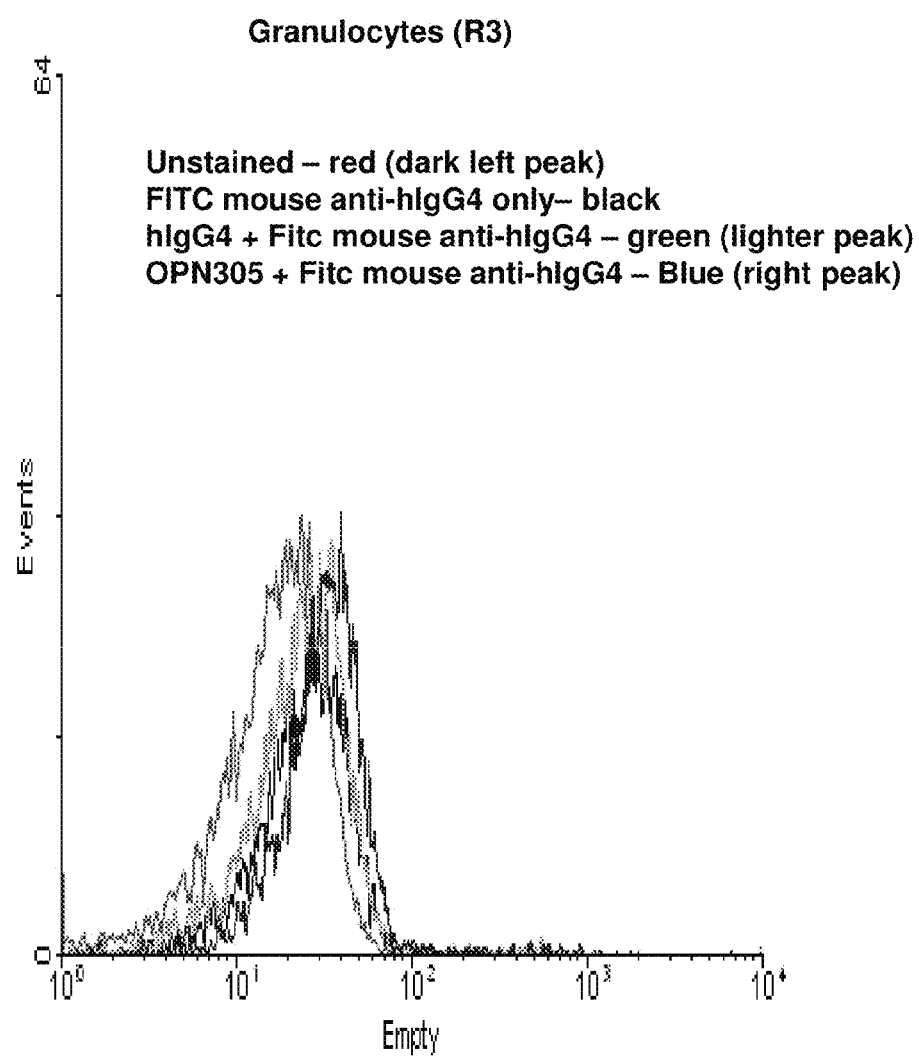
FIG. 13 shows 3 FACS analysis traces that show that OPN-305 binds to monkey TLR2 which is expressed on granulocytes (FIG. 13A) and monocytes (FIG. 13B), but not lymphocytes (FIG. 13C)
Figure 13B:
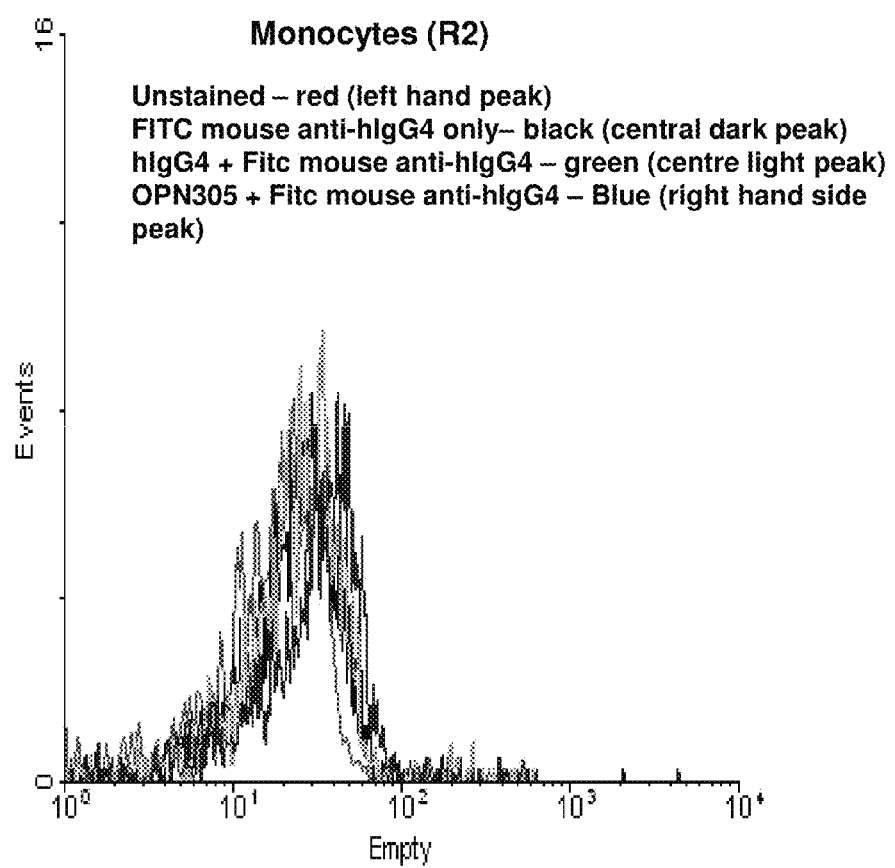
Figure 13C:
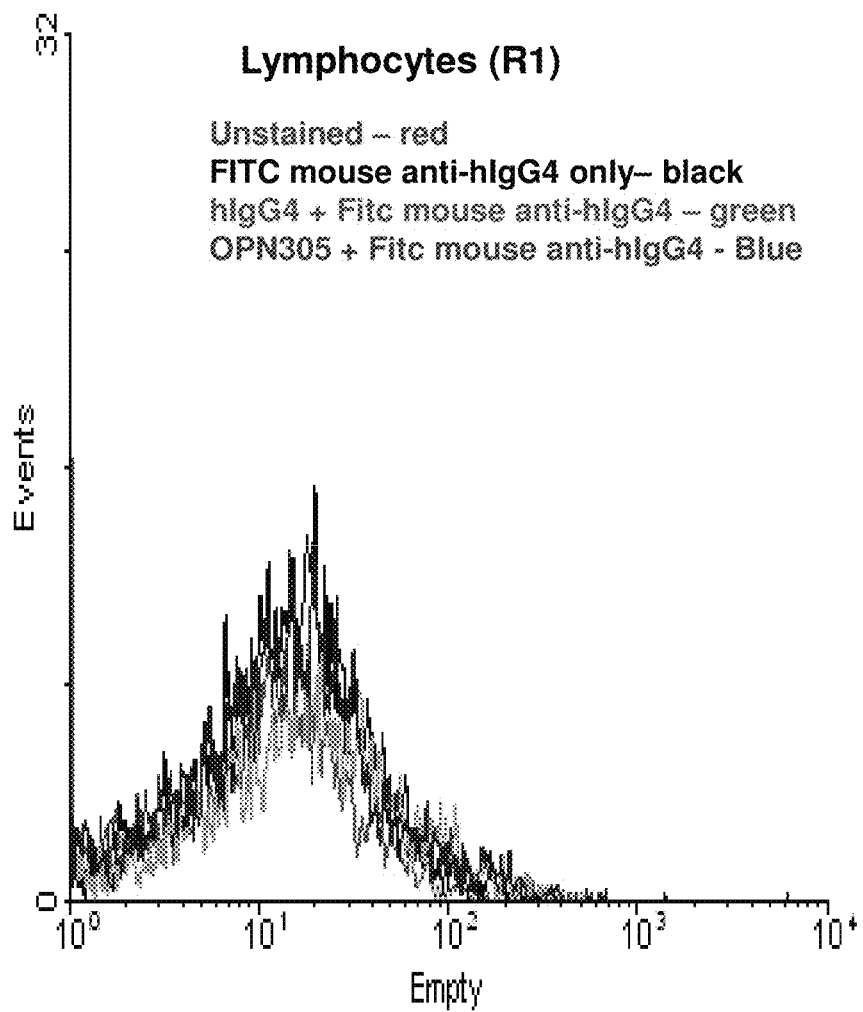

The results are shown in FIGS. 13A, B and C. The different cell types were gated according to their forward and side scatter characteristics. FIG. 13A relates to granulocytes. FIG. 13B relates to monocytes. FIG. 13C relates to lymphocytes. Binding was demonstrated by a histogram shift to the right of cells incubated with OPN-305 (blue histogram—this being the peak at the right hand side of the group of peaks) compared to cells incubated with isotype control antibody (green histogram—this being the second peak, moving from left to right, this peak being in a lighter colour). The results in FIGS. 13A and 13B show that the blue peak has moved further to the right than the green peak. This shows that OPN-305 binds to monkey TLR2 which is expressed on granulocytes and monocytes. OPN-305 therefore exhibits a wide cross-reactivity to Toll-like Receptor 2 expressed on different cell types.

(ii) Competition Assay

Whole blood cells from cynomologus monkeys were incubated with 1.0 µg/ml biotinylated OPN-301 either alone or in the presence of 1.0 µg or 10 µg/ml OPN-305 or an IgG4 isotype control antibody (for OPN305) for 30 minutes at room temperature. Cells were then washed and incubated with streptavidin conjugated to PECy7 for a further 30 minutes.

The OPN-301 monoclonal antibody is a murine IgG1 anti-TLR2 antibody (mouse Toll-like Receptor 2 (TLR2) antibody, clone T2.5, HyCult Biotechnology b.v., Cell Sciences, Canton, USA: catalogue number 1054).

The OPN-305 monoclonal antibody is a fully human antibody having the light chain defined herein as SEQ ID NO:2 and a heavy chain as defined herein in SEQ ID NO:5.

Figure 14A:
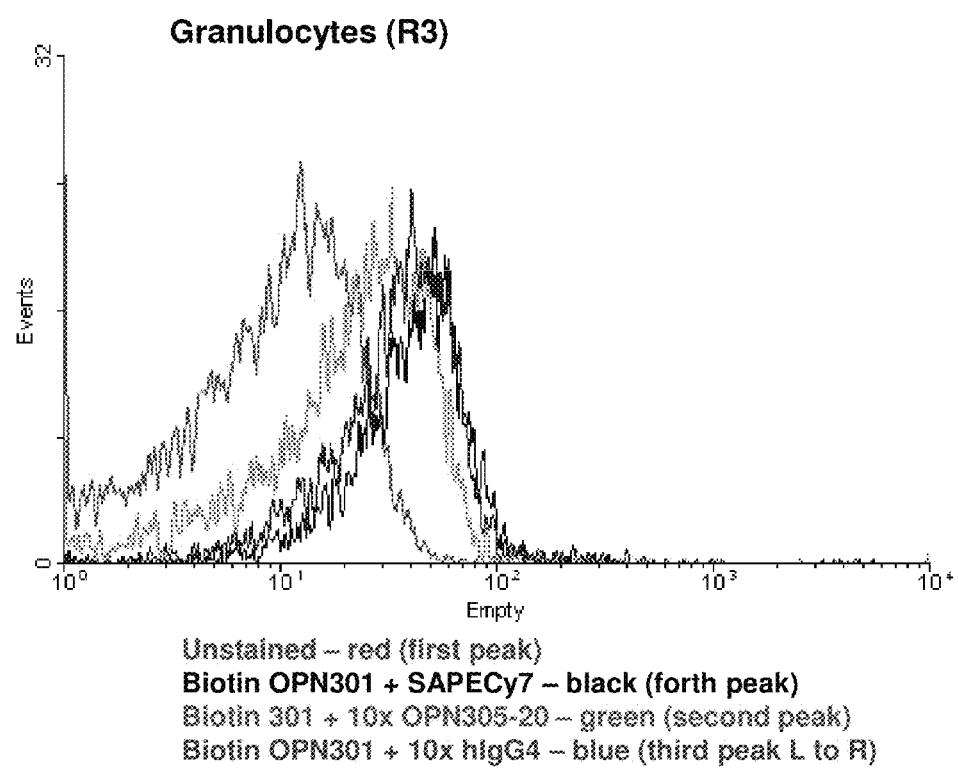
FIG. 14(A) shows the results for granulocytes and FIG. 14(B) shows the results for monocytes, FIGS. 15 (A) and (B) show traces of antibody samples which have been polished by size exclusion chromatography on a 16/60 Sephacryl S200 column.
Figure 14B:
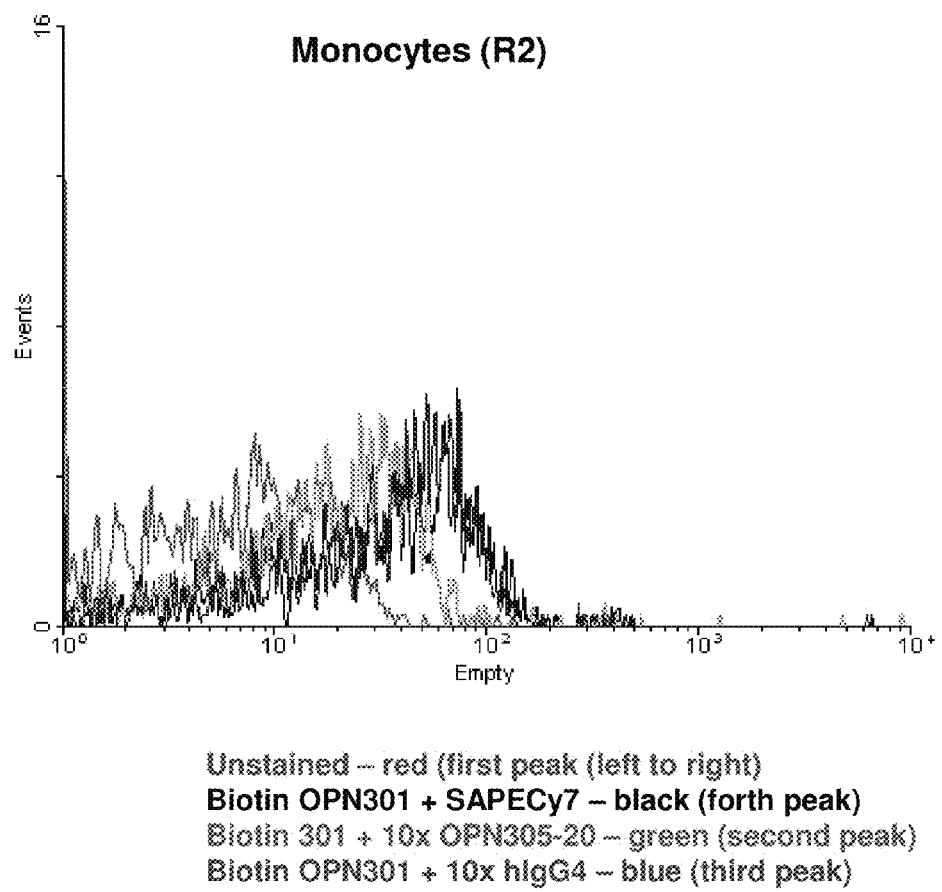

Binding was measured using FACScalibur from Becton Dickinson. The results are shown in FIGS. 14 A, B and C. FIG. 14A relates to granulocytes. FIG. 14B relates to monocytes. FIG. 14C relates to lymphocytes. Binding of OPN-305 is demonstrated by a shift to the left of the green histograms (representing OPN-301+OPN-305) compared to OPN-301 alone (black histograms) which demonstrates than OPN-305 is competing with OPN-301 for binding to monkey TLR2. Accordingly, it can again be seen that OPN305 is competing for monkey Toll-like Receptor 2 binding. This further confirms that OPN-305 is cross-reactive to Toll-like Receptor 2 expressed on human, mouse or monkey cells.

Example 7

Immunogenicity of OPN-305 Monoclonal Antibody

Analysis of the OPN-305 antibody was performed to determine the presence of immunogenic epitopes which may result in an immune response, such as a HAMA response, being raised against the antibody by the subject to whom the antibody is administered. As discussed hereinbefore, the presence of T cell epitopes is highly undesirable as the production of a neutralising antibody response against the antibody would result in that antibody no longer being suitable for administration to that patient for therapeutic purposes. The OPN-305 antibody was therefore screened to ensure that no T cell epitopes were evidently present.

Materials and Methods:
Preparation and Selection of Donor PBMC

Peripheral blood mononuclear cells (PBMC) were isolated from healthy community donor buffy coats (from blood drawn within 24 hours) obtained from the National Blood Transfusion Service (Addenbrooke's Hospital, Cambridge, UK). PBMC were isolated from buffy coats by LYMPHOPREP™ (Axis-Shield, Dundee, UK) density centrifugation and CD8+ T cells were depleted using CD8+ ROSETTE-SEP™ (StemCell Technologies Inc., London, UK). Donors were characterized by identifying HLA-DR haplotypes using a Biotest SSP-PCR based tissue-typing kit (Biotest, Landsteinerstraβe, Denmark) as well as determining T cell responses to a control antigen keyhole limpet haemocyanin (KLH) (Pierce, Rockford, USA). PBMC were then frozen and stored in liquid nitrogen until required.

A cohort of 21 donors was selected to best represent the number and frequency of HLA-DR allotypes expressed in the world population. Analysis of the allotypes expressed in the cohort against those expressed in the world population revealed that coverage of >80% was achieved and that all major HLA-DR alleles (individual allotypes with a frequency >5% expressed in the world population) were well represented.

EpiScreen Time Course T Cell Proliferation Assays

The antibody was subjected to analysis to determine the presence of T cell epitopes as taught by international patent application No WO 2007/099341. PBMCs from each donor were thawed, counted and viability assessed. Cells were revived in room temperature AIMV culture medium (Invitrogen, Paisley, UK) and resuspended in AIMV to $4.6 \times 10^6$ PBMC/ml. For each donor, bulk cultures were established in which a total of 1 ml proliferation cell stock was added to a 24 well plate. A total of 1 ml of each diluted test sample was added to the PBMC to give a final concentration of 50 µg/ml per sample. For each donor, a positive control (cells incubated with 100 µg/ml KLH) and a negative control (cells incubated with culture media only) were also included. For the first 4 donors, an additional control was included to test for modulation of T cell responses by the test samples, where test sample and KLH were both added to the PBMC. Comparison of these samples with KLH alone can be used to assess the effects of the test samples on proliferation. Cultures were incubated for a total of 8 days at 37° C. with 5% $CO_2$. On days 5, 6, 7 and 8, the cells in each well were gently resuspended and 3×100 µl aliquots transferred to individual wells of a round bottomed 96 well plate. The cultures were pulsed with 1 µCi [3H]-Thymidine (Perkin Elmer™, Waltham, Mass., USA) in 100 µl AIMV culture medium and incubated for a further 18 hours before harvesting onto filter mats (Perkin Elmer™, Waltham, Mass., USA) using a TomTec Mach III cell harvester. Counts per minute (cpm) for each well were determined by MELTILEX™ (Perkin Elmer™, Waltham, Mass., USA) scintillation counting on a Microplate Beta Counter in paralux, low background counting mode. In order to assess potential toxicity of the test samples, cell viability counts (using VICELL™ counter and trypan blue dye exclusion) were performed on samples of test cultures and media and KLH controls for the first 10 donors after 7 days incubation.

EpiScreen Data Analysis

For proliferation assays, an empirical threshold of a stimulation index (SI) equal to or greater than 2 (SI≥2) has been previously established whereby samples inducing proliferative responses above this threshold are deemed positive (where included, borderline SIs≥1.95 are highlighted). Extensive assay development and previous studies have shown that this is the minimum signal to noise threshold allowing maximum sensitivity without detecting large numbers of false positive responses. For proliferation data sets (n=3), positive responses were defined by statistical and empirical thresholds:

Significance (p<0.05) of the response by comparing cpm of test wells against medium control wells using unpaired two sample student's t-test.

Stimulation index greater than 2 (SI≥2), where SI=mean of test wells (cpm)/mean medium control wells (cpm).

In addition, intra-assay variation was assessed by calculating the coefficient of variance and standard deviation (SD) of the raw data from replicate cultures.

Results

The anti-TLR2 antibody OPN-305 (VK5/VH4) was purified to homogeneity by Protein A affinity chromatography followed by size exclusion chromatography.

The variant named VK5/VH4 is the OPN-305 fully humanised monoclonal antibody disclosed herein. The OPN-305 monoclonal antibody is a fully humanised antibody having a light chain amino acid sequence defined herein as SEQ ID NO:2 and a heavy chain amino acid sequence defined herein in SEQ ID NO:5.

Figure 15:
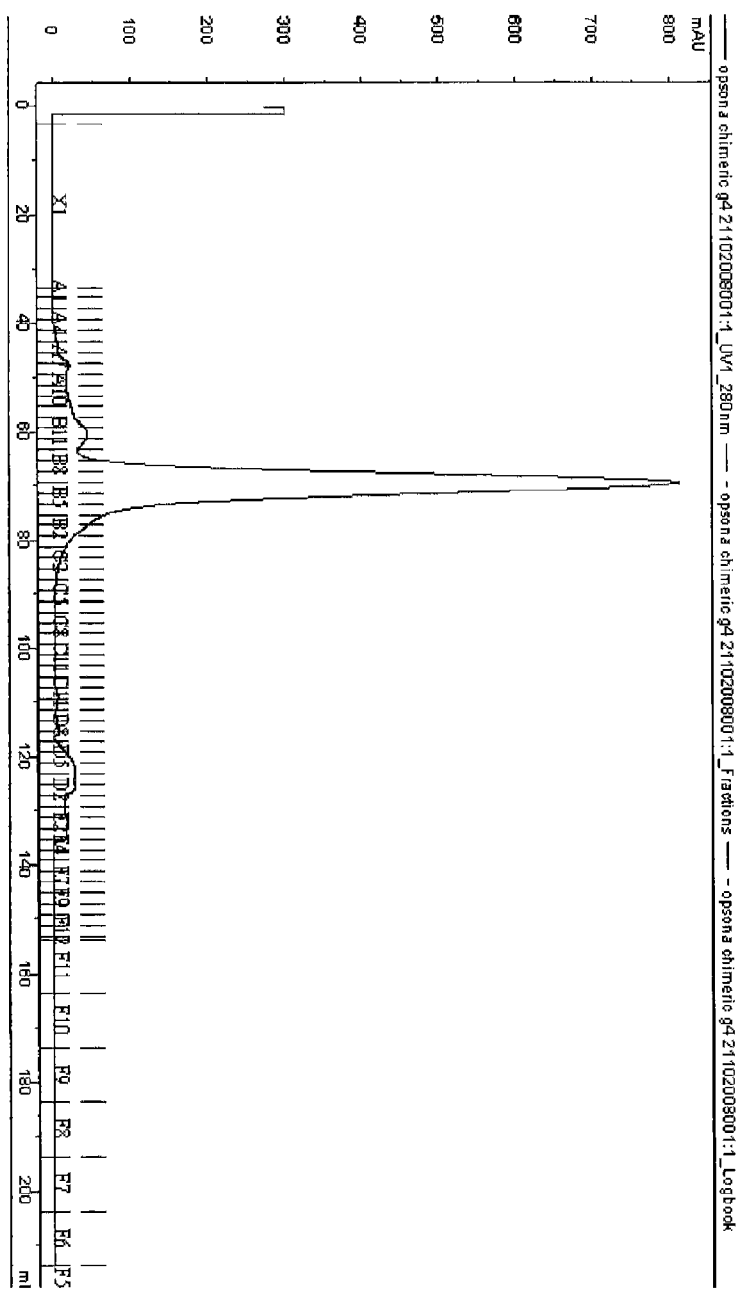
FIG. 15(A) showing an anti-TLR2 chimeric antibody, FIG. 15(B) showing the OPN305 antibody (VK5/VH4). In each case the monomer peak spanning fractions B8 to B4 was collected.
Figure 15:
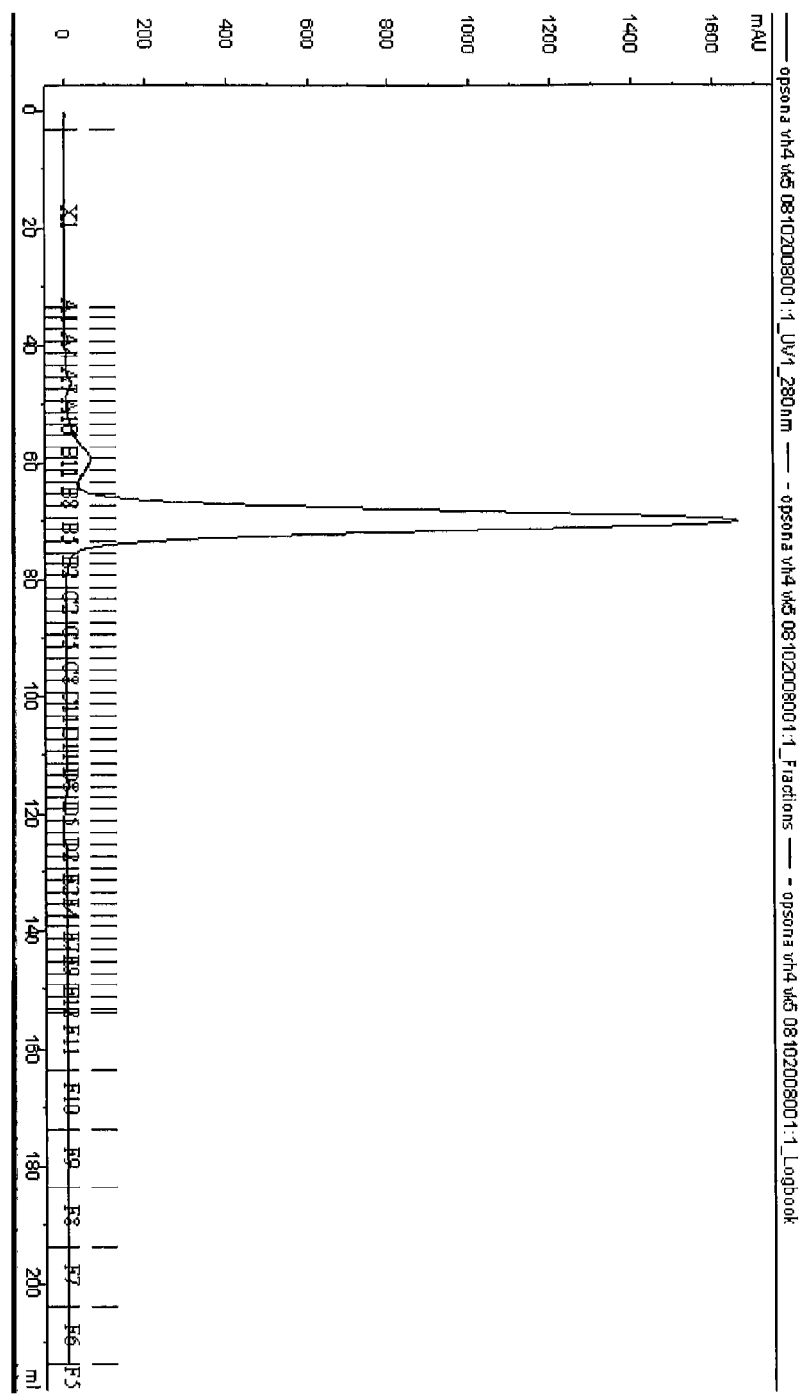

All preparations were derived from single peaks representing monomeric, non-aggregated antibody (FIGS. 15 A and B) and were found to contain endotoxin at <5 EU/mg.

The three test samples were tested against a cohort of 21 healthy donors using EpiScreen™ (Antitope, UK) time course T cell assays in order to determine the relative risk of immunogenicity. The samples were tested at a final concentration of 50 µg/ml as this amount provided a saturating concentration which was sufficient to stimulate detectable protein-specific T cell responses.

Figure 16:
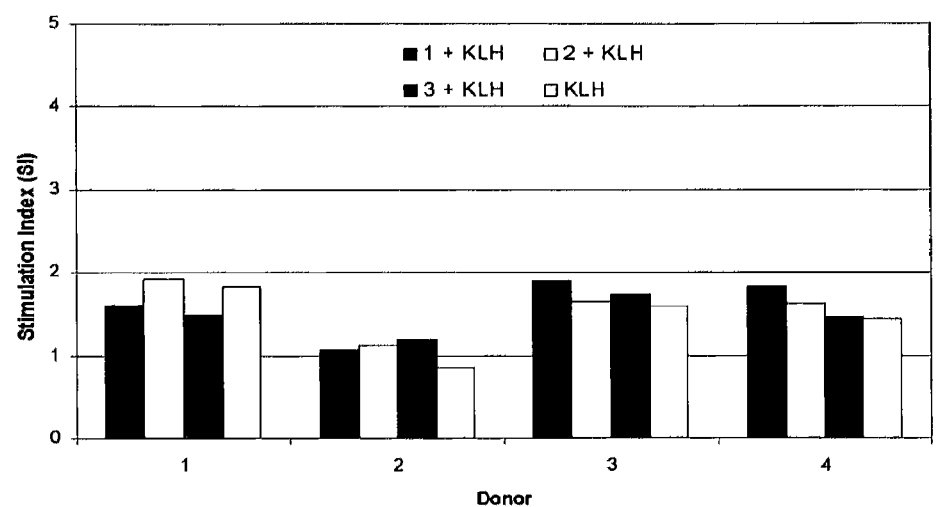
FIG. 16 shows the pre-screen of test samples for cytotoxicity and T cell modulation activity tested in 4 donor samples. Sample 1 (first column of each group (black bar)) is a chimeric anti-TLR2 antibody, sample 2 (second column of each group of results (white coloured bar) is VK5/VH4 (OPN305), sample 3 (third bar (dark grey) is a comparative antibody designated VK5/VH5 along with KLH, while sample 4 (fourth bar on right hand side of each group (light grey)) is a KLH only control. The results show viable cell counts on day 7. The S.I.s of samples incubated in the presence of KLH were compared those of KLH alone. S.I.s were averaged over the four day sampling period. The cut-off for determining positive responses with an SI 2.

The results of the T cell modulation and cell toxicity studies were analysed. The cell viabilities in the cultures after seven days range from 65% to 95% and are similar between all test samples, media control and KLH control. The test samples were therefore not considered to have a toxic effect on the cells used in the assay. In addition, FIG. 16 shows that there are no significant differences (Student's t-test p<0.05) between the SIs induced by KLH either alone or in the presence of the test samples. This suggests that the test samples do not directly modulate CD4+ T cell activation in response to KLH (control antigen). FIG. 16 shows the results of a pre-screen of test samples for cytotoxicity and T cell modulation activity. Sample 1 is chimeric anti-TLR2 (the F'ab fragment derived from the T2.5 murine antibody conjugated to the Fc region of human IgG4), sample 2 is the anti-TLR2 antibody OPN-305 (VK5/VH4, OPN305), sample 3 is variant anti-TLR2 antibody designated VK5/VH5.

Figure 17A:
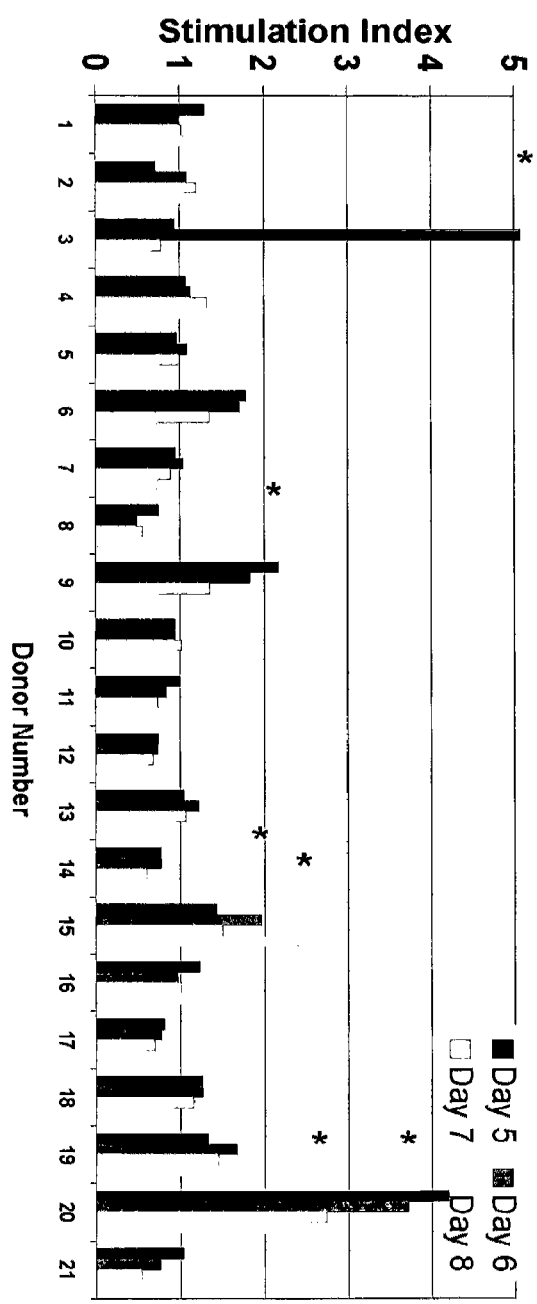
FIGS. 17 (A), (B) and (C) show 3 bar charts showing the results of episcreen testing. Chimeric anti-TLR2, VK5/VH4 and VK5/VH5 antibodies were tested in EpiScreen™ time course T cell assays using PBMC from 21 donors. Bulk cultures of PBMC incubated with test antibodies were sampled on days 5, 6, 7 and 8, and pulsed with $^3$H-Thymidine. Cells were harvested and incorporation of radioactivity measured by scintillation counting. Results for each triplicate sample were averaged and normalized by conversion to Stimulation Index (SI). The SI for each time point with each donor is shown above for (a) the chimeric antibody, (b) the OPN-305 anti-TLR2 antibody (designated VK5/VH4), (c) a comparative anti-TLR2 antibody designated VK5/VH5. The cut-off for determining positive responses with an SI≥2 is highlighted by the thick black horizontal line and significant responses ($p<0.05$ in a student's t-test) are indicated (*).
Figure 17B:
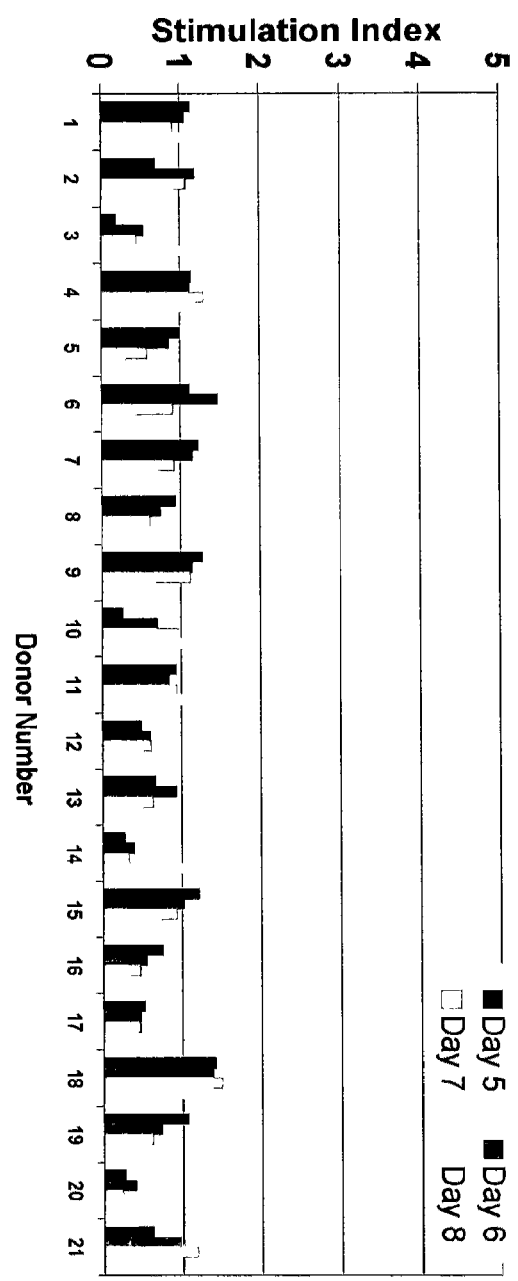
Figure 17C:
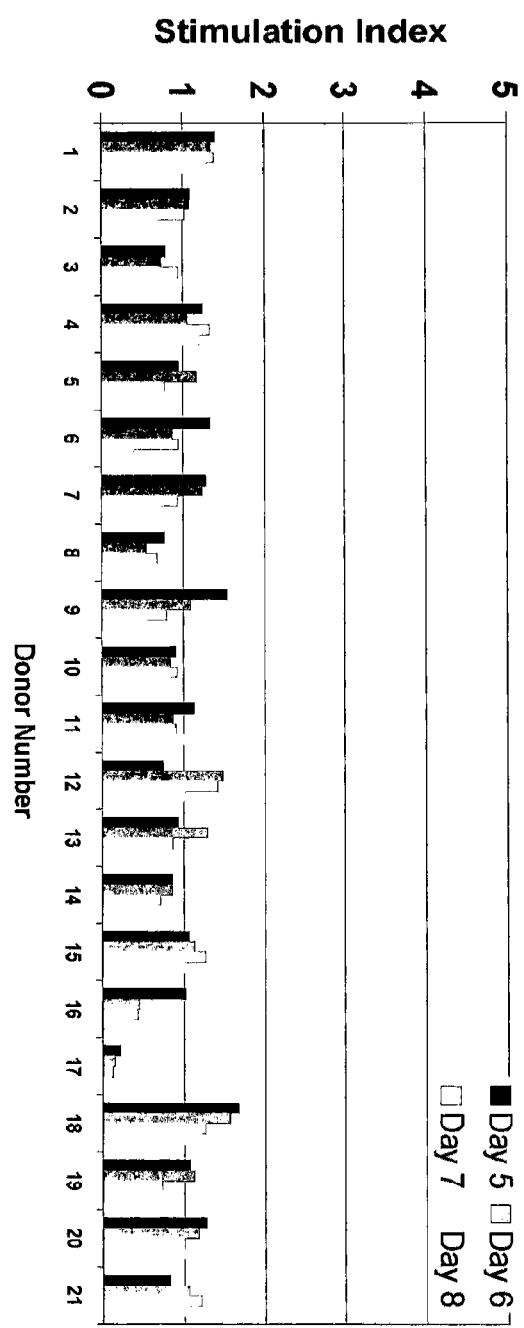

The results from the EpiScreen™ time course proliferation assay performed with the OPN-305 (VK5/VH4, OPN-305) and VK5/VH5 comparative anti-Toll-like Receptor 2 antibodies as well as the anti-TLR2 chimeric antibodies were analysed (FIGS. 17 A, B and C). The chimeric anti-TLR2 antibody stimulated responses in 4 of the 21 donors (18% of the study cohort) where the SI≥2 and significance was achieved in the Student's t-test (p<0.05). Donor 20 gave a particularly vigorous response with high SIs throughout the test period and a strong response (SI=6.99) was also observed with donor 3 on day 6. In contrast none of the donors in the study cohort responded positively to OPN-305. The OPN-305 (VK5/VH4) antibody did not therefore produce any significant T cell responses in the donors that responded positively to the chimeric antibody.

Conclusions

The positive CD4+ T cell proliferation responses observed in the EpiScreen™ time course T cell assay against the chimeric antibody was in the expected range of 15-40%. Importantly, frequent and potent T cell responses were observed against the control antigen, KLH, that indicate that the assay functioned as expected. The results also show that the fully humanized antibody OPN-305 (VK5/VH4) failed to induce any positive immune responses in any donors and this antibody is therefore considered to have a low risk of immunogenicity in the clinic.

Figure 18:
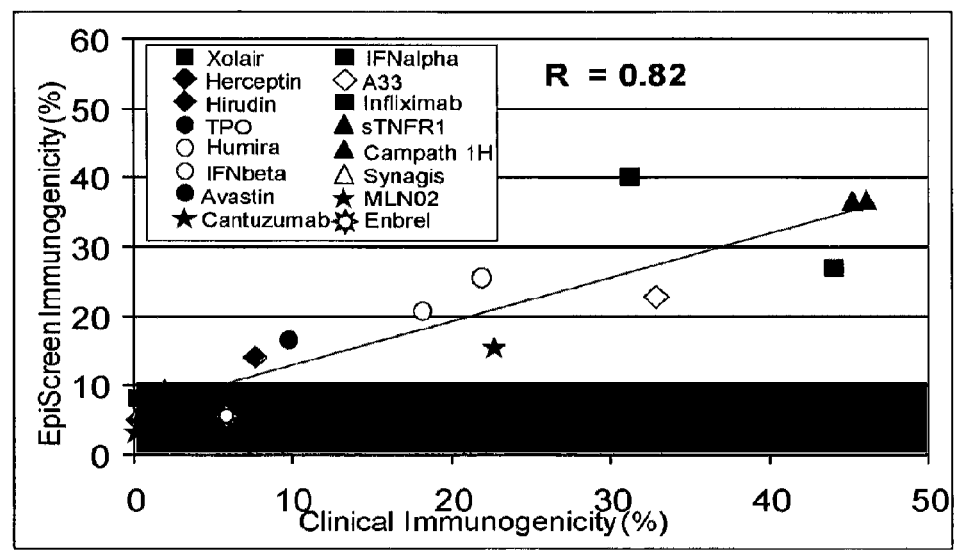
FIG. 18 shows a comparison of immunogenicity predicted using EPISCREEN™ Technology and immunogenicity observed in a clinical setting. 16 therapeutic proteins were tested for their relative risk of immunogenicity using EPISCREEN™ technology. Results were plotted against the frequency of immunogenicity (anti-therapeutic antibody responses) observed for each protein when used in the clinic (data sourced from PubMed). The line of regression and the correlation coefficient is shown.

FIG. 18 shows a clear correlation between the level of immunogenicity observed using the EpiScreen™ assay and the level of immunogenicity (anti-protein therapeutic antibody responses) that has been actually observed in the clinic against a large panel of therapeutic proteins (Baker and Jones, 2007). High levels of immunogenicity were observed in both the clinical data and EpiScreen™ assays for proteins such as Infliximab and Campath, whereas relatively low levels of immunogenicity were observed for proteins such as Xolair, Herceptin, and Avastin. Importantly, the OPN-305 antibody induced responses in <10% of the study cohort, which, based on previous experience is associated with biotherapeutics with a low risk of immunogenicity.

Example 8

Determination and Comparison of Binding Affinity of OPN-305 Monoclonal Antibody

Immunological biosensors, for example BIACORE™ surface plasmon resonance (SPR) instruments that measure the binding and dissociation of antigen-antibody complexes in real time, allow the elucidation of binding kinetics. The rate of dissociation of a compound and its subsequent optimisation is especially important for biopharmaceutical antibody development. BIACORE uses surface Plasmon resonance (SPR) to monitor the interaction between a surface bound molecule ligand and its binding partner in solution 'analyte', in real time. SPR is an electron charge-density wave phenomenon, which arises at the surface of a metallic layer when light is reflected at the layer under conditions of total internal reflectance. The surface plasmons that are generated are sensitive to any changes in the refractive index of the medium on the opposite side of the metallic layer from the reflected light. Protein-protein interactions occurring at the surface affect the refractive index of the medium and can therefore be detected. Binding of molecules to the ligand modified sensor surface generates a response, which is proportional to the bound mass allowing small changes in the amount of bound analyte to be detected (down to low picogram levels). The technique can be used to measure affinity constants (KD) over the range $10^{-6}$ to $10^{-12}$ M, association rate constants (ka) between 103 and 107 M-1 s-1 and dissociation rate constants (kd) between $10^{-1}$ and $10^{-6}$ s$^{-1}$ (1-3).

The aim of this study was to use the BIACORE T100 surface plasmon (Biacore, Inc.) resonance instrument for the high resolution kinetic characterisation of the interaction between two related receptors and three mAbs. The two receptors under investigation were recombinant rhTLR-2 (recombinant human TLR-2) and rmTLR2/Fc (recombinant murine TLR-2).

Materials and Methods

Instrument Preparation

Before running any samples a system check (Biacore Preventative Maintenance Kit 2) was performed. All the systems tested passed (Reagent pump, Refractometer, Injections, Noise, Mixing and Buffer Selector) indicating that the instrument was performing to criteria set by the manufacturer. Following the system check the Desorb/Sanitize (Biacore Preventative Maintenance Kit 2) program was run to clean the instrument.

Assay Development

System Preparation

Upon insertion of the CM5 chip the system was primed and then normalised with BIAnormalising solution (Biacore Preventative Maintenance Kit 2). All samples were run at 25° C. with a sample rack incubated at 25° C. unless stated. The chip was added to the system with HBS-EP used as the running buffer. The chip surface was primed with two 30 second injections of 50 mM NaOH then left until a stable baseline was obtained in all the Flow cells (Fcs).

Sample Preparation

Two antibodies were analysed, the OPN-305 anti-Toll-like Receptor 2 antibody, as described herein, and the T2.5 murine anti-Toll-like Receptor 2 antibody (derived from hybridoma clone T2.5, HyCult Biotechnology b.v., Cell Sciences, Canton, USA: catalogue number 1054). Both monoclonal antibodies were stored as supplied and diluted to 1 μg.ml-1 for all immobilization runs. The receptors rhTLR-2 and rmTLR2/Fc were reconstituted from the dry powder using HBS-EP to a final concentration of 1000 nM and stored at 4° C. No carrier protein was added to this solution.

Immobilisation Conditions and Activity

A direct assay was chosen for this study based on the results of a previous study where this set up was shown to be optimal. For kinetic experiments the amount of immobilised ligand needs to be limited to avoid mass transfer effects at the surface of the chip.

Using an average MW of 77.5 kDa for the glycosylated human receptor analyte (rhTLR-2), 150 kDa for the ligand (mAb) and the stoichiometry (Sm) as 2, an ideal target amount of ligand to immobilise would be 145 RUs. This level of immobilization was also suitable for the murine receptor even though it had a MW of 98 kDa.

All antibodies were immobilised using standard amine coupling chemistry. Immobilisation was carried out at a protein concentration of around 1 μg.ml-1 in 10 mM Acetate buffer pH5.5 to a target response level of 150 RUs on three CM5 Series S sensor chips. Kinetic data was obtained at a flow rate of 40 μl·min-1 to minimise any potential mass transfer effects. The blank (no receptor) and a single concentration of the analytes (100 nM) was repeated at the start of the kinetic runs in order to check the stability of both the surface and two receptors over the kinetic analyses. Two repeats of the kinetic analysis were carried out and the results compared.

In order to observe a sufficient signal decrease (3-10%) during the dissociation phase of the kinetic cycles, dissociation was measured for 2000 seconds.

Results

The results are shown in Table 1. Association rates ($K_{on}$) and dissociation rates ($K_{off}$) were calculated using a bivalent binding model (BIAcore Evaluation Software version 3.2). The equilibrium dissociation constant (Ko) was calculated as the ratio $k_o n/k_{on}$.

TABLE 1

| | Murine TLR2 | | | Human TLR2 | | |
|---|---|---|---|---|---|---|
| Antibody | ON Kd (1/Ms) | OFF Kd (1/s) | Kd (M) | ON Kd (1/Ms) | OFF Kd (1/s) | Kd (M) |
| T2.5 | 9703 | 0.000141 | $1.56 \times 10^{-8}$ | 4819 | 0.000230 | $4.82 \times 10^{-8}$ |
| OPN-305 | 6772 | 0.000082 | $1.19 \times 10^{-8}$ | 3098 | 0.0000895 | $2.89 \times 10^{-8}$ |

The results indicate that OPN-305 binds to both human Toll-like Receptor 2 and murine Toll-like Receptor 2 with a higher binding affinity than the T2.5 monoclonal antibody. FIG. 19 shows an alignment showing the sequence identify between the amino acid sequences of the OPN-305 fully humanised anti-TLR2 antibody and the T.5 murine anti-TLR2 antibody. A sequence identity divergence of over 10% can be seen. Further, FIG. 20 shows an alignment of the heavy chain variable domain amino acid sequences of the OPN-305 fully humanised anti-TLR2 antibody and the T.5 murine anti-TLR2 antibody. Again, a sequence identity divergence of over 10% is present. Without wishing to be bound by theory, the inventor predicts that the variations in the amino acid sequence of the light and heavy chain of the OPN-305 antibody, over the T2.5 murine antibody, confer improved binding specificity and affinity to the OPN-305 antibody for Toll-like Receptor 2.

Example 9

TLR2 Receptor Occupancy Studies

This experiment was designed to identify the minimal occupancy levels required for inhibition of biological activity of the OPN-305 monoclonal antibody when binding to TLR2. Binding versus function was examined using a THP-1 reporter cell line. In particular the bioactivity of OPN-305 was assessed in Pam3CSK4 induced THP1-CD14 cells.
Materials and Methods
THP1-CD14 cells were seeded at a density of $1 \times 10^6$ cells per well in a 12 well dish. OPN-305 was added to the wells at various concentrations (ranging from 0.000488 µg/ml to 2 µg/ml) prior to the addition of Pam3Csk4 (200 ng/ml). Cells were incubated overnight at 37° C. NF-kB driven SEAP activity was measured by incubating the heat inactivated conditioned media with 160 µl of Quantiblue (Invivogen) reagent for 90 minutes at 37° C. and absorbance was read at 650 nm.

To determine receptor occupancy of OPN305 in THP1-CD14 cells, the THP1-CD14 Blue cells were placed in FACS tubes ($1 \times 10^6$/tube) and FcR were blocked with anti-CD32 blocking reagent (Mitenyl Biotec) for 15 minutes. Cells were labelled with OPN-305 at the various concentrations (ranging from 0.000488 µg/ml to 2 µg/ml) for 15 minutes at room temperature. After washing, cells were incubated with RPE conjugated anti-human IgG4 for 15 minutes at room temperature. After a final wash step, cells were fixed with 2% formol saline in 1% BSA/PBS prior to acquisition. Percentage specific binding was calculated using the formula:

$$\% \text{ specific binding} = \left[ \frac{MFI\ OPN305 - MFI\ \text{isotype} * 100}{\text{Max}\ MFI(OPN305) - MFI\ \text{isotype}} \right]$$

Figure 21C:
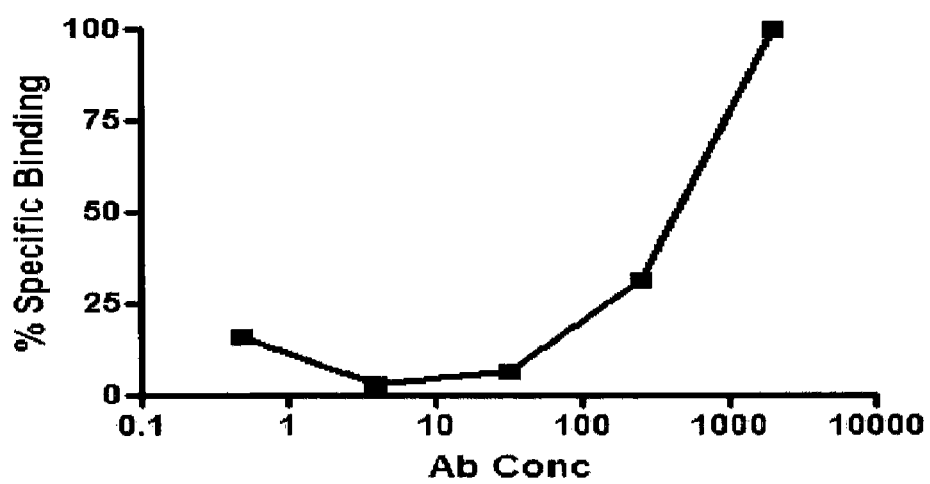
FIG. 21 shows that complete inhibition of TLR2 dependent signalling is achieved with less than maximal receptor binding of OPN-305. Inhibition of NF-kB activity is observed in a dose dependent manner following treatment with Pam3Csk4 (FIGS. 21A and B). OPN305 almost completely inhibits NF-kB activity at concentrations of 2 ug/ml (FIG. 21C).

Results
The results are shown in FIGS. 21A, B and C. These results show that inhibition of NF-kB activity is observed in a dose dependent manner following treatment with Pam3Csk4 (FIGS. 21A and B). OPN-305 almost completely inhibits NF-kB activity at concentrations of 2 ug/ml (FIG. 21C). Percentage of specific binding of OPN-305 in THP1-CD14 cells was calculated using the formula described above.

Saturation binding experiments with THP-1 cells have been related back to inhibition of biological activity in the same populations of cells. Complete inhibition of TLR2 dependent signalling can be achieved with less than maximal receptor binding. This is a complex system and it seems likely that levels of TLR2 are significantly higher than in the heterodimeric partners TLR1 and TLR6. The receptor occupancy looks at saturation binding of TLR2 as a monomer or heterodimer. It seems likely that neutralisation of enough TLR2 to reduce probability of free TLR2 finding a partner to form a functional signalling complex may be an explanation for the apparent loss of biological activity at less than 100% receptor occupancy.

Example 10

Determination of Whether the OPN-305 Antibody Acts as a Competitive or Non-Competitive Inhibitor of TLR2 Dependent Signalling Materials and Methods
THP1 CD14 Blue cells were seeded at 100,000 cells per well in a 96 well plate. Cells were briefly pre-incubated with 0, 1, 10 and 100 ng/ml of OPN-305 before being stimulated with varying doses of Pam3Csk4 overnight at 37° C. 40 ul of supernatant was removed and heat inactivated at 65° C. for 10 minutes. NF-kB driven SEAP activity was measured by incubating the heat inactivated conditioned media with 160 ul of Quantiblue (Invivogen) reagent for 90 minutes at 37° C. followed by reading at 650 nm. Assuming the receptor in the cell based assay behaves similarly to an enzyme, V (NF-kB activity) versus S [Pam3CSK4] was plotted as well as double reciprocal lineweaver-burk plots (1/v vs 1/s).
Results
The results are shown in FIG. 22, where FIG. 22A depicts NF-kB dependent SEAP activity versus [Pam3CSK4], while FIG. 22B depicts a Lineweaver Burk plot of 1/V versus 1/S.

These results show that as ligand concentration is increased, a classic rightward shift of the dose response curve is seen (FIG. 22A). Analysis of the Lineweaver Burk plots (FIG. 22B) suggests a competitive mechanism at low ligand concentration but that the kinetics change as the ligand exceeds a certain threshold. Establishing the nature of the inhibitory effect is challenging in cells as the readout is biological activity and this is dependent not only on TLR2/ligand interaction but also the recruitment of TLR1 or TLR6 to generate a competent dimeric signalling complex. Expression profiling analysis using publicly available databases suggests that TLR2 is present in significant excess to TLR1 or TLR6 which may explain the potential for a bi-phasic response as an effect of titration of partner molecules.

Example 11

Determination of Whether OPN-305 Ligation to TLR2 Alters the Response to Other TLR2 Ligands This experiment considered whether inhibition of TLR2 by OPN-305 affects the response of other TLRs to their respective ligands.

Materials and Methods

THP1 CD14 Blue cells were seeded at 25,000 cells per well in a 384 well plate. Cells were pre-incubated for 120 minutes with 0, 1, 10 and 100 ng/ml of OPN-305 or a human IgG4 isotype control antibody before being stimulated with varying doses of different Toll-like Receptor ligand agonists. NF-kB driven SEAP activity was measured directly in the conditioned media following overnight incubation using HEK blue detection media.

Flagellin was used as a TLR5 ligand, ultra pure LPS as a TLR4 ligand and Pam3CSK and FSL-1 as TLR2 ligands.

Results

Figure 23:
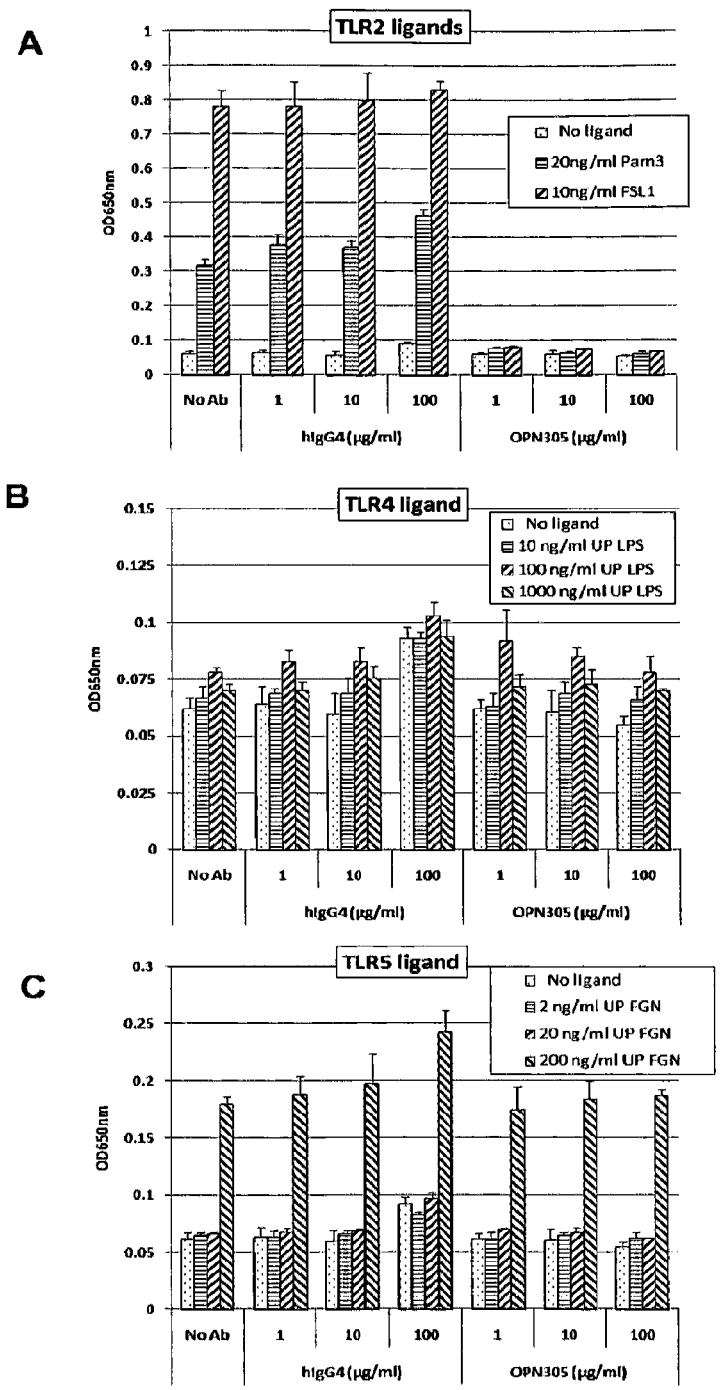
FIG. 23 shows 3 charts A, B and C, depicting that the Toll-like Receptor mediated responses to flagellin (TLR5, FIG. 23C) and LPS (TLR4, FIG. 23B) were unaltered when compared to control cells not exposed to OPN-305. As expected, Toll-like Receptor 2 mediated responses to Pam3CSK and FSL-1 were blocked by OPN-305 (FIG. 23A). This suggests that OPN-305 is not bringing about any unexpected increase or decrease in TLR4 or TLR5 responsiveness to ligands.

The results are shown in FIGS. 23A, B and C. Responses to flagellin (FIG. 23C) and LPS (FIG. 23B) were unaltered when compared to control cells not exposed to OPN-305. As expected Pam3CSK and FSL-1 mediated TLR2 activation responses were blocked by OPN-305 (FIG. 23A). Responses to flagellin and LPS were unaltered when compared to control cells not exposed to OPN-305. As expected Pam3CSK and FSL-1 responses were blocked by OPN-305. This suggests that OPN-305 is not bringing about any unexpected increase or decrease in TLR4 or TLR5 responsiveness to ligands.

Example 12

Use of OPN-305 in the Treatment of Sepsis

Materials and Methods:

Groups of female BALB/c mice (n=4) were treated with the OPN-305 monoclonal antibody at the doses of 10 mg/Kg, 2 mg/Kg and 0.4 mg/Kg 30 minutes prior to treatment with 100 ug of Pam3Csk4. All treatments were administered intraperitoneally. Four hours later, mice were sacrificed by lethal anaesthesia and blood was taken. Serum was derived and cytokine concentrations were determined by ELISA. Serum was diluted 1/10 for KC and IL-12p40 and 1/5 for IL-6 ELISAs.

Figure 24:
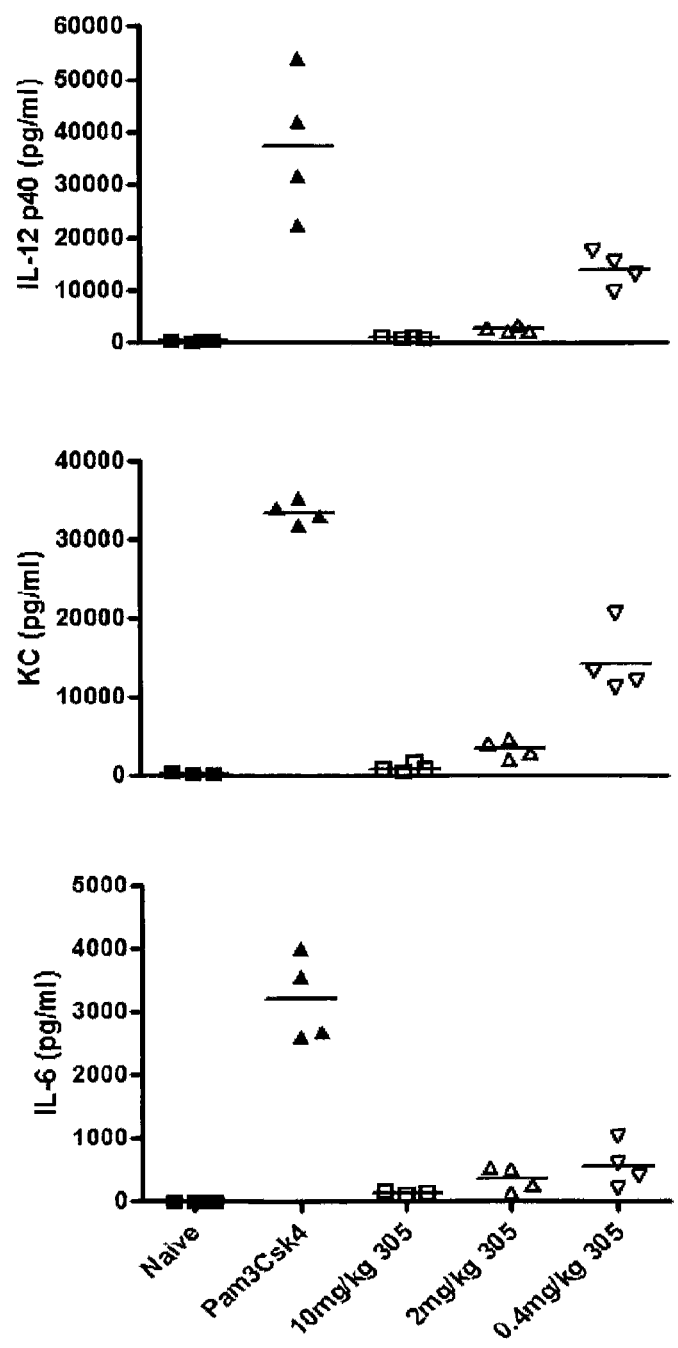
FIG. 24 shows that the OPN-305 monoclonal antibody inhibits Pam3Csk4 induced sepsis. Groups of female BALB/c mice (n=4) were treated with OPN-305 at the doses indicated 30 minutes prior to treatment with 100 ug of Pam3Csk4.

Results:

The results are shown in FIGS. 24A, B and C. OPN305 is shown to inhibit Pam3Csk4 induced sepsis. Low dose (0.4 mg/kg) administration of the anti-TLR2 OPN305 can significantly inhibit Pam3Csk4 induced cytokines in mice.

This experiment was also repeated with OPN-305 only using i.v. (intravenous) administration of the OPN305 antibody followed by i.p. (intraperitoneal) injection of the TLR2 agonist Pam3CSK to ensure the positive effects were not a consequence of antibody and agonist being delivered to the same compartment.

Figure 25:
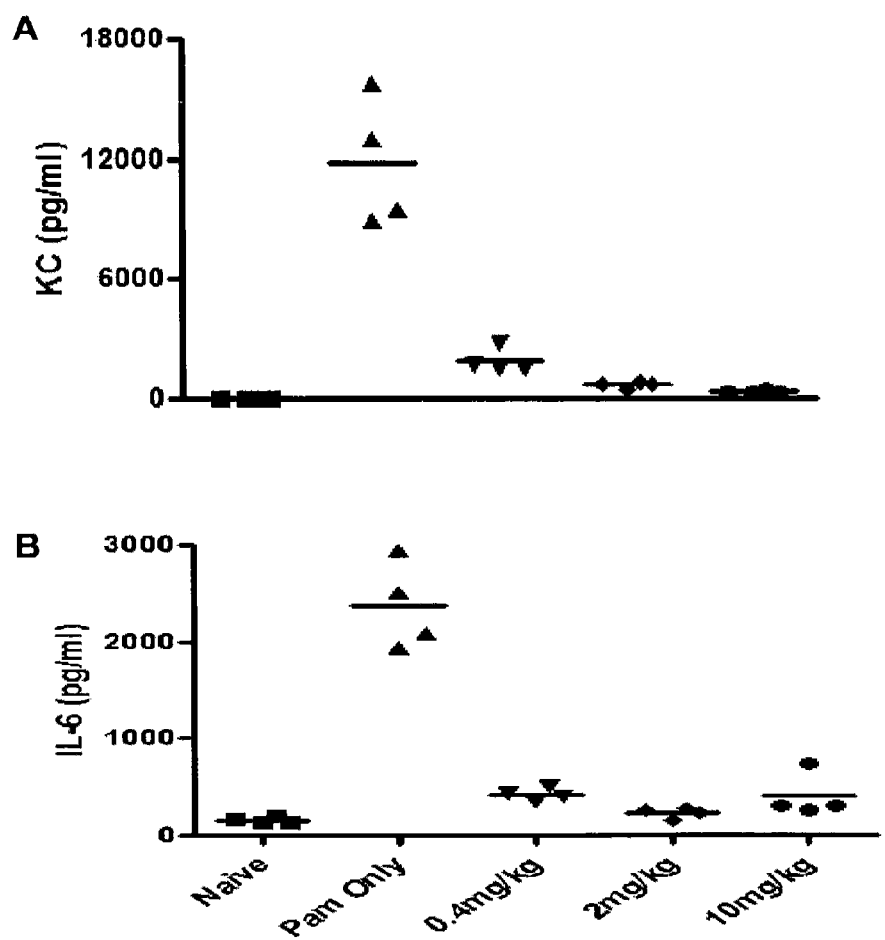
FIG. 25 shows that OPN305 inhibits Pam3Csk4 induced sepsis. In this experiment, OPN305 was administered intravenously 30 minutes prior to intraperitoneal administration of 100 ug of Pam3Csk4. Four hours later, mice were sacrificed by lethal anaesthesia and blood was taken. Serum was derived and cytokine concentrations were determined by ELISA. Sera was diluted at 1/10 for KC (FIG. 25A) and 1/5 for IL-6 (FIG. 25B) ELISAs.

The results of that experiment are shown in FIGS. 25A and B. The results show that the OPN-305 monoclonal antibody inhibits Pam3Csk4 induced sepsis. This result is equivalent to the previous experiment, this demonstrating that OPN-305 delivered systemically can inhibit serum cytokine production in response to i.p (intraperitoneal) administration of Pam3CSK.

Example 13

Binding of OPN-305 Monoclonal Antibody to TLR2 Expressed on Rat Cells

Materials and Methods

NR8383 cells were purchased from ATCC and grown in FK12 media as instructed by ATCC. Cells were blocked with rat specific anti-CD32 (mouse IgG1) for 10 minutes at room temperature. Cells were treated with OPN305 (or isotype) for 15 minutes, washed, detected with RPE anti-human IgG4 and fixed with 2% formol saline prior to acquisition. NR8383 cells were also stained with a polyclonal rabbit anti-rat TLR2 antibody, and detected with Alexa-Fluor 488 anti-rabbit IgG.

Figure 26:
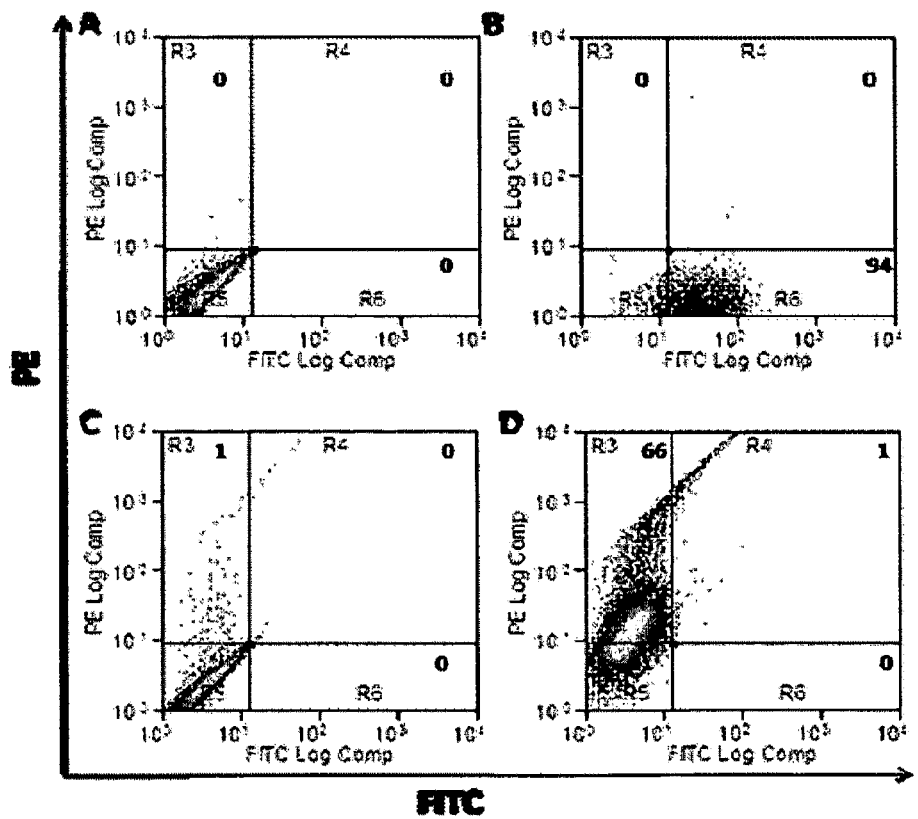
FIG. 26 shows TLR2 is expressed on rat alveolar macrophages (NR8383), and is detected using OPN305. (A) Unstained cells, (B) positive control; polyclonal rabbit anti-rat TLR2 primary antibody, secondary antibody was anti-rabbit Alexa-Fluor 488; (C) Cells treated with polyclonal human IgG4, secondary antibody was human anti-IgG4 PE; (D) OPN305 stained cells, secondary antibody anti-human IgG4 PE.

Results:

The results are shown in FIG. 26 which shows that TLR2 is expressed on rat alveolar macrophages (NR8383), and is detected using OPN305. (A) Unstained cells, (B) positive control; polyclonal rabbit anti-rat TLR2 primary antibody, secondary antibody was anti-rabbit Alexa-Fluor 488; (C) Cells treated with polyclonal human IgG4, secondary antibody was human anti-IgG4 PE; (D) OPN305 stained cells, secondary antibody anti-human IgG4 PE.

Example 14

Binding of OPN-305 Monoclonal Antibody to TLR2 Expressed on Porcine Cells

Materials and Methods

Pig PBMCs were purified from blood using Ficoll. Cells were counted and $1 \times 10^6$ cells were placed per tube. In the absence of a specific CD32 blocking reagent for pigs, cells were blocked using human anti-CD32 in a matrix of 50% FCS/BSA in PBS for 10 minutes. Cells were incubated with OPN305 (or isotype control) for 15 minutes at room temperature. 1H11 (mouse anti-pig TLR2, gift from Javier Dominguez) was used as a positive control. After washing, cells were incubated with RPE conjugated anti-human IgG4 for 15 minutes at room temperature. After a final wash step, cells were fixed, acquired and analysed.

Results

Figure 27:
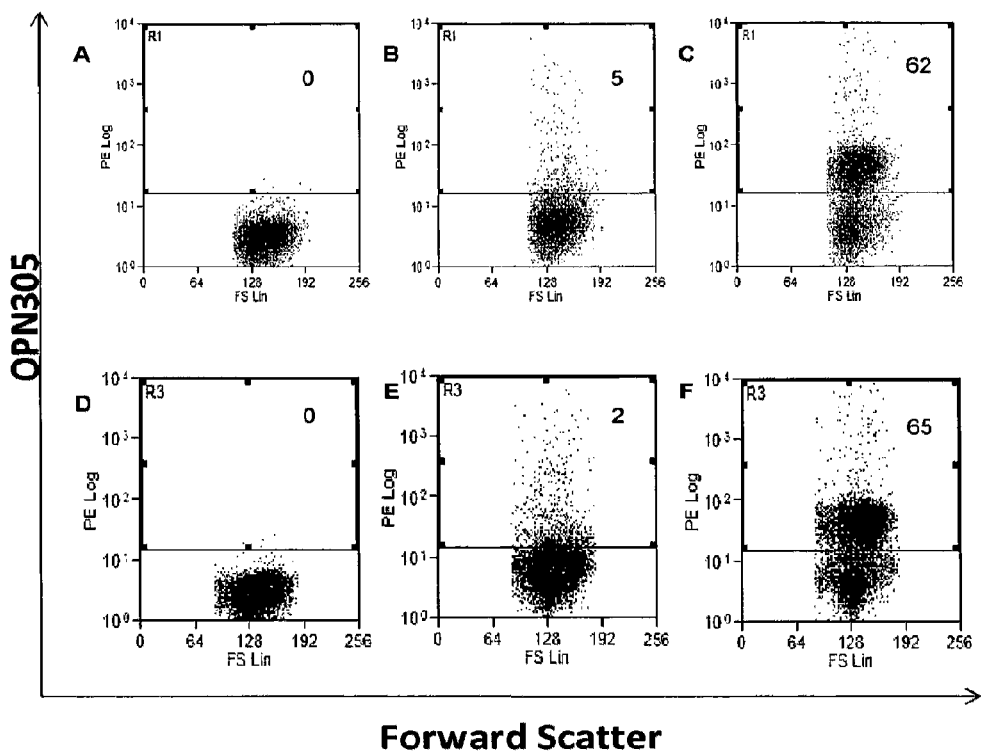
FIG. 27 shows TLR2 is expressed on porcine PBMCs and is stained by OPN305. PBMCs were purified by separation using Ficoll. A-C represent PBMCs from Pig 666 and D-F is from Pig 488. A, D is unstained; B, E is labelled with polyclonal human IgG4, followed by secondary staining with PE labelled anti-human IgG4; C, F is labelled with OPN305, followed by PE labelled anti-human IgG4.

The results are shown in FIG. 27. TLR2 is expressed on porcine PBMCs and is stained by OPN305. PBMCs were purified by separation using Ficoll. A-C represents PBMCs from Pig 666 and D-F is from Pig 488. A, D is unstained; B, E is labelled with control polyclonal human IgG4, followed by secondary staining with PE labelled anti-human IgG4; C, F is labelled with OPN305, followed by PE labelled anti-human IgG4.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A neutralising antibody or an antigen binding portion thereof comprising a light chain variable domain comprising the amino acid sequence of SEQ ID NO: 1 or a sequence which has at least 90% amino acid sequence identity with SEQ ID NO: 1 and a heavy chain variable domain comprising the amino acid sequence of SEQ ID NO:4 or a sequence which has at least 90% amino acid sequence identity with SEQ ID NO:4, wherein the antibody or antigen binding portion specifically binds to Toll-like Receptor 2 (TLR2) and wherein the antibody or antigen binding portion antagonises TLR2 independently of binding of the antibody or antigen binding portion to CD32, and wherein the light chain variable domain comprises CDR1, CDR2 and CDR3 of SEQ ID NO:7, SEQ ID NO:8 and SEQ ID NO:9, respectively, and the heavy chain variable domain comprises CDR1, CDR2 and CDR3 of SEQ ID NO: 10, SEQ ID NO: 11 and SEQ ID NO: 12, respectively.

2. The Toll-like Receptor 2 neutralising antibody or antigen binding portion as claimed in claim 1 wherein the variable domain of the light chain is joined to a Kappa constant domain.

3. The Toll-like Receptor 2 neutralising antibody or antigen binding portion as claimed in claim 1 wherein the variable domain of the heavy chain is joined to at least one constant domain derived from an antibody of the subclass immunoglobulin G, isotype 4 (IgG4).

4. The Toll-like Receptor 2 neutralising antibody or antigen binding portion as claimed in claim 3 wherein amino acid residue 241 of a hinge region of the heavy chain is substituted from a serine residue to a proline residue (S241P).

5. The Toll-like Receptor 2 neutralising antibody or antigen binding portion as claimed in claim 1 wherein the light chain comprises the amino acid sequence of SEQ ID NO:2.

6. The Toll-like Receptor 2 neutralising antibody or antigen binding portion as claimed in claim 5 wherein the heavy chain comprises the amino acid sequence of SEQ ID NO:5.

7. The Toll-like Receptor 2 neutralising antibody or antigen binding portion as claimed in claim 1 wherein the heavy chain comprises the amino acid sequence of SEQ ID NO:5.

8. The Toll-like Receptor 2 neutralising antibody or antigen binding portion as claimed in claim 1, wherein the antibody is a fully humanised antibody or an antigen binding portion thereof.

9. The Toll-like Receptor 2 neutralising antibody or antigen binding portion as claimed in claim 1, wherein the antibody is an isolated antibody or an antigen binding portion thereof.

10. The Toll-like Receptor 2 neutralising antibody or antigen binding portion as claimed in claim 1 wherein the antibody or antigen binding portion binds to human Toll-like Receptor 2 with a $K_D$ of $3 \times 10^{-8}$ M or less.

11. An isolated nucleic acid molecule encoding the antibody or antigen binding portion thereof of claim 1.

12. An expression vector comprising the nucleic acid molecule of claim 11.

13. An isolated host cell comprising the expression vector of claim 12.

14. A method of producing a neutralising Toll-like Receptor 2 antibody or antigen binding portion thereof comprising culturing the host cell of claim 13 under appropriate conditions such that the antibody or antigen binding portion thereof is expressed and isolating the antibody or antigen binding portion thereof from the host cell or from cell culture supernatant.

15. A hybridoma cell line producing the antibody or antigen binding portion as claimed in claim 1.

16. The Toll-like Receptor 2 neutralising antibody or antigen binding portion as claimed in claim 1 wherein the antibody or antigen binding portion has binding specificity to human Toll-like Receptor 2, mouse Toll-like Receptor 2 and monkey Toll-like Receptor 2.

17. The Toll-like Receptor 2 neutralising antibody or antigen binding portion as claimed in claim 1 wherein the light chain variable domain has the amino acid sequence of SEQ ID NO:1 and the heavy chain variable domain has the amino acid sequence of SEQ ID NO:4.

18. The neutralising antibody or antigen binding portion thereof as claimed in claim 1 wherein the light chain variable domain has the amino acid sequence of SEQ ID NO:1 or a sequence which has at least 95% amino acid sequence identity with SEQ ID NO:1 and the heavy chain variable domain has the amino acid sequence of SEQ ID NO:4 or a sequence which has at least 95% amino acid sequence identity with SEQ ID NO:4.

19. A method for treating an inflammatory, respiratory or autoimmune condition or disease which is mediated by Toll-like Receptor 2 activation, comprising administering in-vivo or ex-vivo, a therapeutically effective amount of the antibody or an antigen binding portion thereof according to claim 1 to a subject in need of such treatment.

20. The method as claimed in claim 19 wherein the inflammatory, respiratory or autoimmune condition or disease is selected from the group consisting of rheumatoid arthritis, asthma, chronic obstructive pulmonary disease, allergic response, psoriasis, dermatitis, multiple sclerosis, atherosclerosis, ischemia reperfusion injury, ischemia reperfusion resulting from organ transplantation, ocular disease, uveitis, age-related macular degeneration, renal inflammation and diabetes.

21. A method for treating or preventing sepsis, comprising administering a therapeutically effective amount of the antibody or antigen binding portion according to claim 1 to a subject in need of such treatment.

22. An isolated monoclonal antibody, or antigen binding portion thereof, which binds an epitope on human Toll-like Receptor 2 with a $K_D$ of $3\times10^{-8}$ M or less and which mediates Toll-like Receptor 2 antagonism independently of binding of the antibody or antigen binding portion to CD32 (Fc gamma receptor II), wherein the epitope is recognised by a reference antibody, wherein the reference antibody comprises a heavy chain variable region comprising the amino acid sequence of SEQ ID NO:4 and a light chain variable region comprising the amino acid sequence of SEQ ID NO:1.

23. The isolated monoclonal antibody or antigen binding portion thereof as claimed in claim 22 wherein the reference antibody comprises the heavy chain of SEQ ID NO:5 and the light chain of SEQ ID NO:2.

24. The isolated monoclonal antibody; or antigen binding portion thereof as claimed in claim 22 wherein the antibody or antigen binding portion has binding specificity to human Toll-like Receptor 2, mouse Toll-like Receptor 2 and monkey Toll-like Receptor 2.

* * * * *

UNITED STATES PATENT AND TRADEMARK OFFICE
CERTIFICATE OF CORRECTION

| | |
|---|---|
| PATENT NO. | : 8,734,794 B2 |
| APPLICATION NO. | : 13/382044 |
| DATED | : May 27, 2014 |
| INVENTOR(S) | : Dellacasagrande |

It is certified that error appears in the above-identified patent and that said Letters Patent is hereby corrected as shown below:

In the Claims:

At Column 80, line 12, Claim 12, "antibody;" should be -- antibody --.

Signed and Sealed this
Twenty-fourth Day of November, 2015

Michelle K. Lee
*Director of the United States Patent and Trademark Office*

SEQUENCE LISTING

<160> NUMBER OF SEQ ID NOS: 24

<210> SEQ ID NO 1
<211> LENGTH: 111
<212> TYPE: PRT
<213> ORGANISM: Homo sapiens

<400> SEQUENCE: 1

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Phe Gly Ala Ser Asn Val Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Met Tyr Phe Cys Gln Gln Ser Arg
                85                  90                  95

Lys Leu Pro Trp Thr Phe Gly Gly Gly Thr Lys Val Glu Ile Lys
            100                 105                 110

<210> SEQ ID NO 2
<211> LENGTH: 218
<212> TYPE: PRT
<213> ORGANISM: Homo sapiens

<400> SEQUENCE: 2

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Phe Gly Ala Ser Asn Val Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Met Tyr Phe Cys Gln Gln Ser Arg
                85                  90                  95

Lys Leu Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

```
Val Thr Lys Ser Phe Asn Arg Gly Glu Cys
    210                 215
```

```
<210> SEQ ID NO 3
<211> LENGTH: 1033
<212> TYPE: DNA
<213> ORGANISM: Homo sapiens

<400> SEQUENCE: 3
gacattgtgc tcacccaatc tccagctact ttgtctctgt ctccagggga gagagccacc      60
ctctcctgca gagccagtga aagtgttgaa tactatggca caagtttaat gcagtggtac     120
caacagaaac caggacagcc acccaaactc ctcatctttg gtgcatccaa cgtagaatct     180
ggggtccctg acaggttcag tggcagtggg tctgggacag acttcaccct caagatcagc     240
cggdtggagg ccgaggatgt tggaatgtat ttctgtcagc aaagtaggaa acttccgtgg     300
acgttcggtg gaggcaccaa ggtggaaatc aaacgtgagt agaatttaaa ctttgcttcc     360
tcagttggat cccgcaattc taaactctga ggggtcggga tgacgtggcc attcttgcc      420 taaagcattg agtttactgc aaggtcagaa aagcatgcaa agccctcaga atggctgcaa     480
agagctccaa caaacaatt tagaactta ttaaggaata gggggaagct aggaagaaac       540
tcaaaacatc aagattttaa atacgcttct tggtctcctt gctataatta tctgggataa     600
gcatgctgtt ttctgtctgt ccctaacatg ccctgtgatt atccgcaaac aacacaccca     660
agggcagaac tttgttactt aaacaccatc ctgtttgctt cttcctcag gaactgtggc      720 tgcaccatct gtcttcatct tcccgccatc tgatgagcag ttgaaatctg gaactgcctc     780
tgttgtgtgc ctgctgaata acttctatcc cagagaggcc aaagtacagt ggaaggtgga     840
taacgccctc caatcgggta actcccagga gagtgtcaca gagcaggaca gcaaggacag     900
cacctacagc ctcagcagca ccctgacgct gagcaaagca gactacgaga aacacaaagt     960
ctacgcctgc gaagtcaccc atcagggcct gagctcgccc gtcacaaaga gcttcaacag    1020
gggagagtgt tag                                                        1033

<210> SEQ ID NO 4
<211> LENGTH: 118
<212> TYPE: PRT
<213> ORGANISM: Homo sapiens

<400> SEQUENCE: 4

Gln Val Gln Leu Val Gln Ser Gly Ser Glu Leu Lys Lys Pro Gly Ala
1               5                   10                  15

Ser Val Lys Leu Ser Cys Lys Ala Ser Gly Phe Thr Phe Thr Thr Tyr
            20                  25                  30

Gly Ile Asn Trp Val Arg Gln Ala Pro Gly Gln Gly Leu Glu Trp Ile
        35                  40                  45

Gly Trp Ile Tyr Pro Arg Asp Gly Ser Thr Asn Phe Asn Glu Asn Phe
    50                  55                  60

Lys Asp Arg Ala Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Leu Thr Gly Gly Thr Phe Leu Asp Tyr Trp Gly Gln Gly Thr
            100                 105                 110

Thr Val Thr Val Ser Ser
        115
```

```
<210> SEQ ID NO 5
<211> LENGTH: 445
<212> TYPE: PRT
<213> ORGANISM: Homo sapiens

<400> SEQUENCE: 5

Gln Val Gln Leu Val Gln Ser Gly Ser Glu Leu Lys Lys Pro Gly Ala
1               5                   10                  15

Ser Val Lys Leu Ser Cys Lys Ala Ser Gly Phe Thr Phe Thr Thr Tyr
            20                  25                  30

Gly Ile Asn Trp Val Arg Gln Ala Pro Gly Gln Gly Leu Glu Trp Ile
        35                  40                  45

Gly Trp Ile Tyr Pro Arg Asp Gly Ser Thr Asn Phe Asn Glu Asn Phe
    50                  55                  60

Lys Asp Arg Ala Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Leu Thr Gly Gly Thr Phe Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
```

|  |  |  |  | 385 |  |  |  | 390 |  |  |  | 395 |  |  |  | 400 |
|---|---|---|---|---|---|---|---|---|---|---|---|---|---|---|---|---|
| Ser | Phe | Phe | Leu | Tyr | Ser | Arg | Leu | Thr | Val | Asp | Lys | Ser | Arg | Trp | Gln |
|  |  |  |  | 405 |  |  |  |  |  | 410 |  |  |  |  | 415 |
| Glu | Gly | Asn | Val | Phe | Ser | Cys | Ser | Val | Met | His | Glu | Ala | Leu | His | Asn |
|  |  |  |  | 420 |  |  |  |  |  | 425 |  |  |  |  | 430 |
| His | Tyr | Thr | Gln | Lys | Ser | Leu | Ser | Leu | Ser | Leu | Gly | Lys |
|  |  |  |  | 435 |  |  |  |  |  | 440 |  |  |  |  | 445 |

<210> SEQ ID NO 6
<211> LENGTH: 2163
<212> TYPE: DNA
<213> ORGANISM: Homo sapiens

<400> SEQUENCE: 6

| caggttcagc tggtgcagtc tggatctgag ctgaagaagc ctggggcgtc agtgaagttg | 60 |
| tcctgcaagg cttctggctt caccttcaca acctacggta taaactgggt gaggcaggcc | 120 |
| cctggacagg gacttgagtg gattggatgg atttatccta gagatggtag tactaacttc | 180 |
| aatgagaatt tcaaggacag ggccacaatc actgtagaca catccgccag cacagcgtac | 240 |
| atggaactct ccagcctgag atctgaagac actgcggtct atttctgtgc aagactgact | 300 |
| ggtgggacat tccttgacta ttggggccag ggcaccactg tcacagtctc ctcaggtaag | 360 |
| ctttctgggg caggccgggc tgactttgg ctggggcag ggaggggct aaggtgacgc | 420 |
| aggtggcgcc agccaggtgc acacccaatg cccatgagcc cagacactgg accctgcatg | 480 |
| gaccatcgcg gatagacaag aaccgagggg cctctgcgcc ctgggccag ctctgtccca | 540 |
| caccgcggtc acatggcacc acctctcttg cagcttccac caagggccca tccgtcttcc | 600 |
| ccctggcgcc ctgctccagg agcacctccg agagcacagc cgccctgggc tgcctggtca | 660 |
| aggactactt ccccgaaccg gtgacggtgt cgtggaactc aggcgccctg accagcggcg | 720 |
| tgcacacctt cccggctgtc ctacagtcct caggactcta ctccctcagc agcgtggtga | 780 |
| ccgtgccctc cagcagcttg ggcacgaaga cctacacctg caatgtagat cacaagccca | 840 |
| gcaacaccaa ggtggacaag agagttggtg agaggccagc acaggaggg agggtgtctg | 900 |
| ctggaagcca ggctcagccc tcctgcctgg acgcaccccg gctgtgcagc cccagcccag | 960 |
| ggcagcaagg caggccccat ctgtctcctc acctggaggc ctctgaccac ccactcatg | 1020 |
| ctcagggaga gggtcttctg gatttttcca ccaggctccg gcagccaca ggctggatgc | 1080 |
| ccctacccca ggccctgcgc atacaggggc aggtgctgcg ctcagacctg ccaagagcca | 1140 |
| tatccgggag gaccctgccc ctgacctaag cccacccca aggccaaact ctccactccc | 1200 |
| tcagctcaga caccttctct cctcccagat ctgagtaact cccaatcttc tctctgcaga | 1260 |
| gtccaaatat ggtcccccat gcccaccatg cccaggtaag ccaacccagg cctcgccctc | 1320 |
| cagctcaagg cgggacaggt gccctagagt agcctgcatc cagggacagg ccccagccgg | 1380 |
| gtgctgacgc atccacctcc atctcttcct cagcacctga gttcctgggg ggaccatcag | 1440 |
| tcttcctgtt ccccccaaaa cccaaggaca ctctcatgat ctcccggacc cctgaggtca | 1500 |
| cgtgcgtggt ggtggacgtg agccaggaag accccgaggt ccagttcaac tggtacgtgg | 1560 |
| atggcgtgga ggtgcataat gccaagacaa agccgcggga ggagcagttc aacagcacgt | 1620 |
| accgtgtggt cagcgtcctc accgtcctgc accaggactg gctgaacggc aaggagtaca | 1680 |
| agtgcaaggt ctccaacaaa ggcctcccgt cctccatcga gaaaaccatc tccaaagcca | 1740 |
| aaggtgggac ccacggggtg cgagggccac atggacagag gtcagctcgg cccaccctct | 1800 |
| gccctgggag tgaccgctgt gccaacctct gtccctacag ggcagccccg agagccacag | 1860 |

```
gtgtacaccc tgcccccatc ccaggaggag atgaccaaga accaggtcag cctgacctgc    1920
ctggtcaaag gcttctaccc cagcgacatc gccgtggagt gggagagcaa tgggcagccg    1980
gagaacaact acaagaccac gcctcccgtg ctggactccg acggctcctt cttcctctac    2040
agcaggctaa ccgtggacaa gagcaggtgg caggagggga atgtcttctc atgctccgtg    2100
atgcatgagg ctctgcacaa ccactacaca cagaagagcc tctccctgtc tctgggtaaa    2160
tga                                                                 2163
```

<210> SEQ ID NO 7
<211> LENGTH: 15
<212> TYPE: PRT
<213> ORGANISM: Homo sapiens
<400> SEQUENCE: 7

Arg Ala Ser Glu Ser Val Glu Tyr Tyr Gly Thr Ser Leu Met Gln
1               5                   10                  15

<210> SEQ ID NO 8
<211> LENGTH: 7
<212> TYPE: PRT
<213> ORGANISM: Homo sapiens
<400> SEQUENCE: 8

Gly Ala Ser Asn Val Glu Ser
1               5

<210> SEQ ID NO 9
<211> LENGTH: 9
<212> TYPE: PRT
<213> ORGANISM: Homo sapiens
<400> SEQUENCE: 9

Gln Gln Ser Arg Lys Leu Pro Trp Thr
1               5

<210> SEQ ID NO 10
<211> LENGTH: 5
<212> TYPE: PRT
<213> ORGANISM: Homo sapiens
<400> SEQUENCE: 10

Thr Tyr Gly Ile Asn
1               5

<210> SEQ ID NO 11
<211> LENGTH: 17
<212> TYPE: PRT
<213> ORGANISM: Homo sapiens
<400> SEQUENCE: 11

Trp Ile Tyr Pro Arg Asp Gly Ser Thr Asn Phe Asn Glu Asn Phe Lys
1               5                   10                  15

Asp

<210> SEQ ID NO 12
<211> LENGTH: 9
<212> TYPE: PRT
<213> ORGANISM: Homo sapiens
<400> SEQUENCE: 12

Leu Thr Gly Gly Thr Phe Leu Asp Tyr
1               5

```
<210> SEQ ID NO 13
<211> LENGTH: 21
<212> TYPE: PRT
<213> ORGANISM: Homo sapiens

<400> SEQUENCE: 13

Lys Glu Glu Ser Ser Asn Gln Ala Ser Leu Ser Cys Asp Arg Asn Gly
1               5                   10                  15

Ile Cys Lys Gly Ser
            20

<210> SEQ ID NO 14
<211> LENGTH: 13
<212> TYPE: PRT
<213> ORGANISM: Homo sapiens

<400> SEQUENCE: 14

Cys Ser Cys Glu Phe Leu Ser Phe Thr Gln Glu Gln Gln
1               5                   10

<210> SEQ ID NO 15
<211> LENGTH: 784
<212> TYPE: PRT
<213> ORGANISM: Homo sapiens

<400> SEQUENCE: 15

Met Pro His Thr Leu Trp Met Val Trp Val Leu Gly Val Ile Ile Ser
1               5                   10                  15

Leu Ser Lys Glu Glu Ser Ser Asn Gln Ala Ser Leu Ser Cys Asp Arg
                20                  25                  30

Asn Gly Ile Cys Lys Gly Ser Gly Ser Leu Asn Ser Ile Pro Ser
            35                  40                  45

Gly Leu Thr Glu Ala Val Lys Ser Leu Asp Leu Ser Asn Asn Arg Ile
        50                  55                  60

Thr Tyr Ile Ser Asn Ser Asp Leu Gln Arg Cys Val Asn Leu Gln Ala
65                  70                  75                  80

Leu Val Leu Thr Ser Asn Gly Ile Asn Thr Ile Glu Glu Asp Ser Phe
                85                  90                  95

Ser Ser Leu Gly Ser Leu Glu His Leu Asp Leu Ser Tyr Asn Tyr Leu
                100                 105                 110

Ser Asn Leu Ser Ser Ser Trp Phe Lys Pro Leu Ser Ser Leu Thr Phe
            115                 120                 125

Leu Asn Leu Leu Gly Asn Pro Tyr Lys Thr Leu Gly Glu Thr Ser Leu
        130                 135                 140

Phe Ser His Leu Thr Lys Leu Gln Ile Leu Arg Val Gly Asn Met Asp
145                 150                 155                 160

Thr Phe Thr Lys Ile Gln Arg Lys Asp Phe Ala Gly Leu Thr Phe Leu
                165                 170                 175

Glu Glu Leu Glu Ile Asp Ala Ser Asp Leu Gln Ser Tyr Glu Pro Lys
            180                 185                 190

Ser Leu Lys Ser Ile Gln Asn Val Ser His Leu Ile Leu His Met Lys
        195                 200                 205

Gln His Ile Leu Leu Leu Glu Ile Phe Val Asp Val Thr Ser Ser Val
    210                 215                 220

Glu Cys Leu Glu Leu Arg Asp Thr Asp Leu Asp Thr Phe His Phe Ser
225                 230                 235                 240

Glu Leu Ser Thr Gly Glu Thr Asn Ser Leu Ile Lys Lys Phe Thr Phe
```

```
                        245                 250                 255
Arg Asn Val Lys Ile Thr Asp Glu Ser Leu Phe Gln Val Met Lys Leu
                260                 265                 270

Leu Asn Gln Ile Ser Gly Leu Leu Glu Leu Glu Phe Asp Asp Cys Thr
            275                 280                 285

Leu Asn Gly Val Gly Asn Phe Arg Ala Ser Asp Asn Asp Arg Val Ile
        290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
                325                 330                 335

Arg Val Lys Arg Ile Thr Val Glu Asn Ser Lys Val Phe Leu Val Pro
            340                 345                 350

Cys Leu Leu Ser Gln His Leu Lys Ser Leu Glu Tyr Leu Asp Leu Ser
        355                 360                 365

Glu Asn Leu Met Val Glu Tyr Leu Lys Asn Ser Ala Cys Glu Asp
370                 375                 380

Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
                405                 410                 415

Asn Ile Asp Ile Ser Lys Asn Ser Phe His Ser Met Pro Glu Thr Cys
            420                 425                 430

Gln Trp Pro Glu Lys Met Lys Tyr Leu Asn Leu Ser Ser Thr Arg Ile
        435                 440                 445

His Ser Val Thr Gly Cys Ile Pro Lys Thr Leu Glu Ile Leu Asp Val
    450                 455                 460

Ser Asn Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
                485                 490                 495

Leu Leu Pro Met Leu Leu Val Leu Lys Ile Ser Arg Asn Ala Ile Thr
            500                 505                 510

Thr Phe Ser Lys Glu Gln Leu Asp Ser Phe His Thr Leu Lys Thr Leu
        515                 520                 525

Glu Ala Gly Gly Asn Asn Phe Ile Cys Ser Cys Glu Phe Leu Ser Phe
    530                 535                 540

Thr Gln Glu Gln Gln Ala Leu Ala Lys Val Leu Ile Asp Trp Pro Ala
545                 550                 555                 560

Asn Tyr Leu Cys Asp Ser Pro Ser His Val Arg Gly Gln Gln Val Gln
                565                 570                 575

Asp Val Arg Leu Ser Val Ser Glu Cys His Arg Thr Ala Leu Val Ser
            580                 585                 590

Gly Met Cys Cys Ala Leu Phe Leu Leu Ile Leu Leu Thr Gly Val Leu
        595                 600                 605

Cys His Arg Phe His Gly Leu Trp Tyr Met Lys Met Met Trp Ala Trp
    610                 615                 620

Leu Gln Ala Lys Arg Lys Pro Arg Lys Ala Pro Ser Arg Asn Ile Cys
625                 630                 635                 640

Tyr Asp Ala Phe Val Ser Tyr Ser Glu Arg Asp Ala Tyr Trp Val Glu
                645                 650                 655

Asn Leu Met Val Gln Glu Leu Glu Asn Phe Asn Pro Pro Phe Lys Leu
            660                 665                 670
```

```
Cys Leu His Lys Arg Asp Phe Ile Pro Gly Lys Trp Ile Ile Asp Asn
            675                 680                 685

Ile Ile Asp Ser Ile Glu Lys Ser His Lys Thr Val Phe Val Leu Ser
690                 695                 700

Glu Asn Phe Val Lys Ser Glu Trp Cys Lys Tyr Glu Leu Asp Phe Ser
705                 710                 715                 720

His Phe Arg Leu Phe Glu Glu Asn Asn Asp Ala Ala Ile Leu Ile Leu
                725                 730                 735

Leu Glu Pro Ile Glu Lys Lys Ala Ile Pro Gln Arg Phe Cys Lys Leu
            740                 745                 750

Arg Lys Ile Met Asn Thr Lys Thr Tyr Leu Glu Trp Pro Met Asp Glu
            755                 760                 765

Ala Gln Arg Glu Gly Phe Trp Val Asn Leu Arg Ala Ala Ile Lys Ser
770                 775                 780
```

<210> SEQ ID NO 16
<211> LENGTH: 784
<212> TYPE: PRT
<213> ORGANISM: Mus musculus
<400> SEQUENCE: 16

```
Met Leu Arg Ala Leu Trp Leu Phe Trp Ile Leu Val Ala Ile Thr Val
1               5                   10                  15

Leu Phe Ser Lys Arg Cys Ser Ala Gln Glu Ser Leu Ser Cys Asp Ala
            20                  25                  30

Ser Gly Val Cys Asp Gly Arg Ser Arg Ser Phe Thr Ser Ile Pro Ser
        35                  40                  45

Gly Leu Thr Ala Ala Met Lys Ser Leu Asp Leu Ser Phe Asn Lys Ile
50                  55                  60

Thr Tyr Ile Gly His Gly Asp Leu Arg Ala Cys Ala Asn Leu Gln Val
65                  70                  75                  80

Leu Met Leu Lys Ser Ser Arg Ile Asn Thr Ile Glu Gly Asp Ala Phe
                85                  90                  95

Tyr Ser Leu Gly Ser Leu Glu His Leu Asp Leu Ser Asp Asn His Leu
            100                 105                 110

Ser Ser Leu Ser Ser Ser Trp Phe Gly Pro Leu Ser Ser Leu Lys Tyr
        115                 120                 125

Leu Asn Leu Met Gly Asn Pro Tyr Gln Thr Leu Gly Val Thr Ser Leu
130                 135                 140

Phe Pro Asn Leu Thr Asn Leu Gln Thr Leu Arg Ile Gly Asn Val Glu
145                 150                 155                 160

Thr Phe Ser Glu Ile Arg Arg Ile Asp Phe Ala Gly Leu Thr Ser Leu
                165                 170                 175

Asn Glu Leu Glu Ile Lys Ala Leu Ser Leu Arg Asn Tyr Gln Ser Gln
            180                 185                 190

Ser Leu Lys Ser Ile Arg Asp Ile His His Leu Thr Leu His Leu Ser
        195                 200                 205

Glu Ser Ala Phe Leu Leu Glu Ile Phe Ala Asp Ile Leu Ser Ser Val
210                 215                 220

Arg Tyr Leu Glu Leu Arg Asp Thr Asn Leu Ala Arg Phe Gln Phe Ser
225                 230                 235                 240

Pro Leu Pro Val Asp Glu Val Ser Ser Pro Met Lys Lys Leu Ala Phe
                245                 250                 255

Arg Gly Ser Val Leu Thr Asp Glu Ser Phe Asn Glu Leu Leu Lys Leu
            260                 265                 270
```

-continued

```
Leu Arg Tyr Ile Leu Glu Leu Ser Glu Val Glu Phe Asp Asp Cys Thr
            275                 280                 285

Leu Asn Gly Leu Gly Asp Phe Asn Pro Ser Glu Ser Asp Val Val Ser
        290                 295                 300

Glu Leu Gly Lys Val Glu Thr Val Thr Ile Arg Arg Leu His Ile Pro
305                 310                 315                 320

Gln Phe Tyr Leu Phe Tyr Asp Leu Ser Thr Val Tyr Ser Leu Leu Glu
                325                 330                 335

Lys Val Lys Arg Ile Thr Val Glu Asn Ser Lys Val Phe Leu Val Pro
            340                 345                 350

Cys Ser Phe Ser Gln His Leu Lys Ser Leu Glu Phe Leu Asp Leu Ser
        355                 360                 365

Glu Asn Leu Met Val Glu Glu Tyr Leu Lys Asn Ser Ala Cys Lys Gly
370                 375                 380

Ala Trp Pro Ser Leu Gln Thr Leu Val Leu Ser Gln Asn His Leu Arg
385                 390                 395                 400

Ser Met Gln Lys Thr Gly Glu Ile Leu Leu Thr Leu Lys Asn Leu Thr
                405                 410                 415

Ser Leu Asp Ile Ser Arg Asn Thr Phe His Pro Met Pro Asp Ser Cys
            420                 425                 430

Gln Trp Pro Glu Lys Met Arg Phe Leu Asn Leu Ser Ser Thr Gly Ile
        435                 440                 445

Arg Val Val Lys Thr Cys Ile Pro Gln Thr Leu Glu Val Leu Asp Val
450                 455                 460

Ser Asn Asn Asn Leu Asp Ser Phe Ser Leu Phe Leu Pro Arg Leu Gln
465                 470                 475                 480

Glu Leu Tyr Ile Ser Arg Asn Lys Leu Lys Thr Leu Pro Asp Ala Ser
                485                 490                 495

Leu Phe Pro Val Leu Leu Val Met Lys Ile Arg Glu Asn Ala Val Ser
            500                 505                 510

Thr Phe Ser Lys Asp Gln Leu Gly Ser Phe Pro Lys Leu Glu Thr Leu
        515                 520                 525

Glu Ala Gly Asp Asn His Phe Val Cys Ser Cys Glu Leu Leu Ser Phe
530                 535                 540

Thr Met Glu Thr Pro Ala Leu Ala Gln Ile Leu Val Asp Trp Pro Asp
545                 550                 555                 560

Ser Tyr Leu Cys Asp Ser Pro Pro Arg Leu His Gly His Arg Leu Gln
                565                 570                 575

Asp Ala Arg Pro Ser Val Leu Glu Cys His Gln Ala Ala Leu Val Ser
            580                 585                 590

Gly Val Cys Cys Ala Leu Leu Leu Ile Leu Leu Val Gly Ala Leu
        595                 600                 605

Cys His His Phe His Gly Leu Trp Tyr Leu Arg Met Met Trp Ala Trp
610                 615                 620

Leu Gln Ala Lys Arg Lys Pro Lys Lys Ala Pro Cys Arg Asp Val Cys
625                 630                 635                 640

Tyr Asp Ala Phe Val Ser Tyr Ser Glu Gln Asp Ser His Trp Val Glu
                645                 650                 655

Asn Leu Met Val Gln Gln Leu Glu Asn Ser Asp Pro Pro Phe Lys Leu
            660                 665                 670

Cys Leu His Lys Arg Asp Phe Val Pro Gly Lys Trp Ile Ile Asp Asn
        675                 680                 685

Ile Ile Asp Ser Ile Glu Lys Ser His Lys Thr Val Phe Val Leu Ser
690                 695                 700
```

```
Glu Asn Phe Val Arg Ser Glu Trp Cys Lys Tyr Glu Leu Asp Phe Ser
705                 710                 715                 720

His Phe Arg Leu Phe Asp Glu Asn Asn Asp Ala Ala Ile Leu Val Leu
            725                 730                 735

Leu Glu Pro Ile Glu Arg Lys Ala Ile Pro Gln Arg Phe Cys Lys Leu
        740                 745                 750

Arg Lys Ile Met Asn Thr Lys Thr Tyr Leu Glu Trp Pro Leu Asp Glu
            755                 760                 765

Gly Gln Gln Glu Val Phe Trp Val Asn Leu Arg Thr Ala Ile Lys Ser
        770                 775                 780

<210> SEQ ID NO 17
<211> LENGTH: 333
<212> TYPE: DNA
<213> ORGANISM: Homo sapiens
<220> FEATURE:
<221> NAME/KEY: CDS
<222> LOCATION: (1)..(333)

<400> SEQUENCE: 17 gac att gtg ctc acc caa tct cca gct act ttg tct ctg tct cca ggg    48
Asp Ile Val Leu Thr Gln Ser Pro Ala Thr Leu Ser Leu Ser Pro Gly
1               5                   10                  15 gag aga gcc acc ctc tcc tgc aga gcc agt gaa agt gtt gaa tac tat    96
Glu Arg Ala Thr Leu Ser Cys Arg Ala Ser Glu Ser Val Glu Tyr Tyr
            20                  25                  30 ggc aca agt tta atg cag tgg tac caa cag aaa cca gga cag cca ccc   144
Gly Thr Ser Leu Met Gln Trp Tyr Gln Gln Lys Pro Gly Gln Pro Pro
        35                  40                  45 aaa ctc ctc atc ttt ggt gca tcc aac gta gaa tct ggg gtc cct gac   192
Lys Leu Leu Ile Phe Gly Ala Ser Asn Val Glu Ser Gly Val Pro Asp
    50                  55                  60 agg ttc agt ggc agt ggg tct ggg aca gac ttc acc ctc aag atc agc   240
Arg Phe Ser Gly Ser Gly Ser Gly Thr Asp Phe Thr Leu Lys Ile Ser
65                  70                  75                  80 cgg gtg gag gcc gag gat gtt gga atg tat ttc tgt cag caa agt agg   288
Arg Val Glu Ala Glu Asp Val Gly Met Tyr Phe Cys Gln Gln Ser Arg
                85                  90                  95 aaa ctt ccg tgg acg ttc ggt gga ggc acc aag gtg gaa atc aaa       333
Lys Leu Pro Trp Thr Phe Gly Gly Gly Thr Lys Val Glu Ile Lys
            100                 105                 110

<210> SEQ ID NO 18
<211> LENGTH: 111
<212> TYPE: PRT
<213> ORGANISM: Homo sapiens

<400> SEQUENCE: 18

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Phe Gly Ala Ser Asn Val Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Met Tyr Phe Cys Gln Gln Ser Arg
                85                  90                  95
```

```
Lys Leu Pro Trp Thr Phe Gly Gly Gly Thr Lys Val Glu Ile Lys
            100                 105                 110

<210> SEQ ID NO 19
<211> LENGTH: 354
<212> TYPE: DNA
<213> ORGANISM: Homo sapiens
<220> FEATURE:
<221> NAME/KEY: CDS
<222> LOCATION: (1)..(354)

<400> SEQUENCE: 19 cag gtt cag ctg gtg cag tct gga tct gag ctg aag aag cct ggg gcg        48
Gln Val Gln Leu Val Gln Ser Gly Ser Glu Leu Lys Lys Pro Gly Ala
1               5                   10                  15 tca gtg aag ttg tcc tgc aag gct tct ggc ttc acc ttc aca acc tac        96
Ser Val Lys Leu Ser Cys Lys Ala Ser Gly Phe Thr Phe Thr Thr Tyr
            20                  25                  30 ggt ata aac tgg gtg agg cag gcc cct gga cag gga ctt gag tgg att       144
Gly Ile Asn Trp Val Arg Gln Ala Pro Gly Gln Gly Leu Glu Trp Ile
        35                  40                  45 gga tgg att tat cct aga gat ggt agt act aac ttc aat gag aat ttc       192
Gly Trp Ile Tyr Pro Arg Asp Gly Ser Thr Asn Phe Asn Glu Asn Phe
    50                  55                  60 aag gac agg gcc aca atc act gta gac aca tcc gcc agc aca gcg tac       240
Lys Asp Arg Ala Thr Ile Thr Val Asp Thr Ser Ala Ser Thr Ala Tyr
65                  70                  75                  80 atg gaa ctc tcc agc ctg aga tct gaa gac act gcg gtc tat ttc tgt       288
Met Glu Leu Ser Ser Leu Arg Ser Glu Asp Thr Ala Val Tyr Phe Cys
                85                  90                  95 gca aga ctg act ggt ggg aca ttc ctt gac tat tgg ggc cag ggc acc       336
Ala Arg Leu Thr Gly Gly Thr Phe Leu Asp Tyr Trp Gly Gln Gly Thr
            100                 105                 110 act gtc aca gtc tcc tca                                               354
Thr Val Thr Val Ser Ser
        115

<210> SEQ ID NO 20
<211> LENGTH: 118
<212> TYPE: PRT
<213> ORGANISM: Homo sapiens

<400> SEQUENCE: 20

Gln Val Gln Leu Val Gln Ser Gly Ser Glu Leu Lys Lys Pro Gly Ala
1               5                   10                  15

Ser Val Lys Leu Ser Cys Lys Ala Ser Gly Phe Thr Phe Thr Thr Tyr
            20                  25                  30

Gly Ile Asn Trp Val Arg Gln Ala Pro Gly Gln Gly Leu Glu Trp Ile
        35                  40                  45

Gly Trp Ile Tyr Pro Arg Asp Gly Ser Thr Asn Phe Asn Glu Asn Phe
    50                  55                  60

Lys Asp Arg Ala Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Leu Thr Gly Gly Thr Phe Leu Asp Tyr Trp Gly Gln Gly Thr
            100                 105                 110

Thr Val Thr Val Ser Ser
        115
```

```
<210> SEQ ID NO 21
<211> LENGTH: 111
<212> TYPE: PRT
<213> ORGANISM: Mus musculus

<400> SEQUENCE: 21

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Phe Gly Ala Ser Asn Val Glu Ser Gly Val Pro Val
    50                  55                  60

Arg Phe Ser Gly Ser Gly Ser Gly Thr Asp Phe Ser Leu Asn Ile His
65                  70                  75                  80

Pro Val Glu Glu Asp Asp Ile Val Met Tyr Phe Cys Gln Gln Ser Arg
                85                  90                  95

Lys Leu Pro Trp Thr Phe Gly Gly Gly Thr Lys Leu Glu Ile Lys
            100                 105                 110

<210> SEQ ID NO 22
<211> LENGTH: 111
<212> TYPE: PRT
<213> ORGANISM: Homo sapiens

<400> SEQUENCE: 22

Asp Ile Val Leu Thr Gln Ser Pro Ala Ser Leu Ala Leu Ser Leu Gly
1               5                   10                  15

Glu Arg Ala Thr Leu Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Phe Gly Ala Ser Asn Val Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Glu Glu Asp Val Gly Met Tyr Phe Cys Gln Gln Ser Arg
                85                  90                  95

Lys Leu Pro Trp Thr Phe Gly Gly Gly Thr Lys Val Glu Ile Lys
            100                 105                 110

<210> SEQ ID NO 23
<211> LENGTH: 118
<212> TYPE: PRT
<213> ORGANISM: Mus musculus

<400> SEQUENCE: 23

Gln Val Gln Leu Gln Gln Ser Gly Pro Glu Leu Val Asn Pro Gly Ala
1               5                   10                  15

Ser Val Lys Leu Ser Cys Lys Ala Ser Gly Phe Thr Phe Thr Thr Tyr
            20                  25                  30

Gly Ile Asn Trp Val Lys Gln Gly Pro Gly Gln Gly Leu Glu Trp Ile
        35                  40                  45

Gly Trp Ile Tyr Pro Arg Asp Gly Ser Thr Asn Phe Asn Glu Asn Phe
    50                  55                  60

Lys Asp Lys Ala Ala Leu Thr Val Asp Thr Ser Ser Ser Thr Ala Tyr
65                  70                  75                  80
```

```
Met Glu Leu His Ser Leu Thr Ser Glu Asp Ser Ala Val Tyr Phe Cys
                85                  90                  95

Ala Arg Leu Thr Gly Gly Thr Phe Leu Asp Tyr Trp Gly Gln Gly Thr
            100                 105                 110

Thr Leu Thr Val Ser Ser
            115

<210> SEQ ID NO 24
<211> LENGTH: 118
<212> TYPE: PRT
<213> ORGANISM: Homo sapiens

<400> SEQUENCE: 24

Gln Val Gln Leu Val Gln Ser Gly Ser Glu Leu Lys Lys Pro Gly Ala
1               5                   10                  15

Ser Val Lys Leu Ser Cys Lys Ala Ser Gly Phe Thr Phe Thr Thr Tyr
            20                  25                  30

Gly Ile Asn Trp Val Arg Gln Ala Pro Gly Gln Gly Leu Glu Trp Ile
            35                  40                  45

Gly Trp Ile Tyr Pro Arg Asp Gly Ser Thr Asn Phe Asn Glu Asn Phe
        50                  55                  60

Lys Asp Arg Ala Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Leu Thr Gly Gly Thr Phe Leu Asp Tyr Trp Gly Gln Gly Thr
            100                 105                 110

Thr Val Thr Val Ser Ser
            115
```